United States Patent
Doxey et al.

(10) Patent No.: US 11,166,980 B2
(45) Date of Patent: Nov. 9, 2021

(54) COMPOSITIONS, SYSTEMS, KITS, AND METHODS FOR TREATING AN INFECTION

(71) Applicant: Novan, Inc., Morrisville, NC (US)

(72) Inventors: Ryan Doxey, Raleigh, NC (US); Nathan Stasko, Chapel Hill, NC (US); Megan Martin, Cary, NC (US)

(73) Assignee: Novan, Inc., Morrisville, NC (US)

( * ) Notice: Subject to any disclaimer, the term of this patent is extended or adjusted under 35 U.S.C. 154(b) by 0 days.

(21) Appl. No.: 16/091,167

(22) PCT Filed: Apr. 13, 2017

(86) PCT No.: PCT/US2017/027333
§ 371 (c)(1),
(2) Date: Oct. 4, 2018

(87) PCT Pub. No.: WO2017/180822
PCT Pub. Date: Oct. 19, 2017

(65) Prior Publication Data
US 2019/0290681 A1   Sep. 26, 2019

Related U.S. Application Data

(60) Provisional application No. 62/484,252, filed on Apr. 11, 2017, provisional application No. 62/356,891, filed on Jun. 30, 2016, provisional application No. 62/322,064, filed on Apr. 13, 2016.

(51) Int. Cl.
| | |
|---|---|
| *A61K 33/00* | (2006.01) |
| *A61K 47/69* | (2017.01) |
| *A61K 9/00* | (2006.01) |
| *A61K 9/06* | (2006.01) |
| *A61K 47/10* | (2017.01) |
| *A61K 47/34* | (2017.01) |
| *A61K 31/80* | (2006.01) |

(52) U.S. Cl.
CPC ............ *A61K 33/00* (2013.01); *A61K 9/0014* (2013.01); *A61K 9/06* (2013.01); *A61K 31/80* (2013.01); *A61K 47/10* (2013.01); *A61K 47/34* (2013.01); *A61K 47/6903* (2017.08); *A61K 47/6923* (2017.08)

(58) Field of Classification Search
CPC ...... A61K 33/00; A61K 31/80; A61K 9/0014; A61K 9/06; A61K 47/6903; A61K 47/6923; A61K 47/10; A61K 47/34
See application file for complete search history.

(56) References Cited

U.S. PATENT DOCUMENTS

| | | |
|---|---|---|
| 3,754,368 A | 8/1973 | Moore et al. |
| 4,182,827 A | 1/1980 | Jones et al. |
| 4,822,604 A | 4/1989 | Knoll et al. |
| 4,829,092 A | 5/1989 | Nelson et al. |
| 4,917,886 A | 4/1990 | Asche et al. |
| 5,405,919 A | 4/1995 | Keefer |
| 5,519,020 A | 5/1996 | Smith et al. |
| 5,691,423 A | 11/1997 | Smith et al. |
| 5,770,645 A | 6/1998 | Stamler et al. |
| 5,814,656 A | 9/1998 | Saavedra et al. |
| 5,814,666 A | 9/1998 | Green et al. |
| 5,840,759 A | 11/1998 | Mitchell et al. |
| 5,910,316 A | 6/1999 | Keefer et al. |
| 5,912,008 A | 6/1999 | Horstmann et al. |
| 5,958,427 A | 9/1999 | Salzman et al. |
| 5,968,001 A | 10/1999 | Freeman |
| 5,968,528 A | 10/1999 | Deckner et al. |
| 6,017,521 A | 1/2000 | Robinson et al. |
| 6,103,266 A | 8/2000 | Tapolsky et al. |
| 6,103,275 A | 8/2000 | Seitz et al. |
| 6,110,453 A | 8/2000 | Keefer et al. |
| 6,303,141 B1 | 10/2001 | Fischer et al. |
| 6,319,913 B1 | 11/2001 | Mak et al. |
| 6,382,526 B1 | 5/2002 | Reneker et al. |
| 6,465,445 B1 | 10/2002 | Labrie |
| 6,479,058 B1 | 11/2002 | McCadden |
| 6,520,425 B1 | 2/2003 | Reneker |
| 6,565,445 B1 | 5/2003 | Miller |
| 6,695,992 B2 | 2/2004 | Reneker |
| 6,719,997 B2 | 4/2004 | Hsu et al. |
| 6,737,447 B1 | 5/2004 | Smith et al. |
| 6,818,018 B1 | 11/2004 | Sawhney |
| 6,861,064 B1 | 3/2005 | Laakso et al. |
| 7,048,951 B1 | 5/2006 | Seitz et al. |
| 7,704,518 B2 | 4/2010 | Tamarkin et al. |
| 8,241,650 B2 | 8/2012 | Peters |

(Continued)

FOREIGN PATENT DOCUMENTS

| | | |
|---|---|---|
| CA | 2 594 407 A1 | 8/2006 |
| EP | 1 300 424 A1 | 4/2003 |

(Continued)

OTHER PUBLICATIONS

International Search Report and the Written Opinion of the International Searching Authority corresponding to International Patent Application No. PCT/US2017/027333 (11 pages) (dated Jun. 28, 2017).
U.S. Appl. No. 14/133,973, Kougoulos et al., Dec. 19, 2013.
U.S. Appl. No. 14/191,958, Doxey et al., Feb. 27, 2014.
Ahmadi et al. "Sustained Nitric Oxide-Releasing Nanoparticles Induce Cell Death in *Candida albicans* Yeast and Hyphal Cells, Preventing Biofilm Formation In Vitro and in a Rodent Central Venous Catheter Model" *Antimicrobial Agents and Chemotherapy* 60(4):2185-2194 (2016).
Al-Sa'Doni et al. "S-Nitrosothiols: a class of nitric oxide-donor drugs" *Clinical Science* 98:507-520 (2000).

(Continued)

*Primary Examiner* — Ali Soroush
(74) *Attorney, Agent, or Firm* — Myers Bigel, P.A.

(57) ABSTRACT

Provided herein are compositions, systems, kits, and methods for treating a viral, bacterial, protozoan, and/or fungal (e.g., onychomycosis and/or *Tinea pedis*) infection.

16 Claims, 6 Drawing Sheets

(56) References Cited

U.S. PATENT DOCUMENTS

| | | | |
|---|---|---|---|
| 8,343,945 B2 | 1/2013 | Tamarkin et al. | |
| 8,362,091 B2 | 1/2013 | Tamarkin et al. | |
| 8,399,005 B2 | 3/2013 | Schoenfisch et al. | |
| 8,486,374 B2 | 7/2013 | Tamarkin et al. | |
| 8,486,451 B2 | 7/2013 | Morris et al. | |
| 8,591,876 B2 | 11/2013 | Bauman et al. | |
| 8,617,100 B2 | 12/2013 | Eini et al. | |
| 8,636,982 B2 | 1/2014 | Tamarkin et al. | |
| 8,722,103 B2 | 5/2014 | Morris et al. | |
| 8,795,635 B2 | 8/2014 | Tamarkin et al. | |
| 8,795,693 B2 | 8/2014 | Tamarkin et al. | |
| 8,900,553 B2 | 12/2014 | Tamarkin et al. | |
| 9,101,662 B2 | 8/2015 | Tamarkin et al. | |
| 9,161,916 B2 | 10/2015 | Tamarkin et al. | |
| 9,265,725 B2 | 2/2016 | Tamarkin et al. | |
| 9,320,705 B2 | 4/2016 | Tamarkin et al. | |
| 2002/0012816 A1 | 1/2002 | Shimizu et al. | |
| 2002/0013304 A1 | 1/2002 | Wilson et al. | |
| 2002/0028223 A1 | 3/2002 | Vatter et al. | |
| 2002/0082221 A1 | 6/2002 | Herrmann et al. | |
| 2002/0094985 A1 | 7/2002 | Herrmann et al. | |
| 2002/0122771 A1 | 9/2002 | Holland et al. | |
| 2002/0136750 A1 | 9/2002 | Benjamin et al. | |
| 2002/0155174 A1 | 10/2002 | Benjamin et al. | |
| 2003/0044374 A1* | 3/2003 | Roszell | A61K 8/8129 424/70.13 |
| 2003/0077243 A1 | 4/2003 | Fitzhugh | |
| 2003/0159702 A1 | 8/2003 | Lindell et al. | |
| 2003/0175328 A1 | 9/2003 | Shefer et al. | |
| 2003/0205234 A1 | 11/2003 | Bardach et al. | |
| 2003/0219854 A1 | 11/2003 | Guarna et al. | |
| 2003/0235605 A1 | 12/2003 | Lelah et al. | |
| 2004/0009238 A1 | 1/2004 | Miller et al. | |
| 2004/0043068 A1 | 3/2004 | Tedeschi et al. | |
| 2004/0067595 A1 | 4/2004 | Davies et al. | |
| 2004/0068005 A1 | 4/2004 | Szilvassy et al. | |
| 2004/0171589 A1 | 9/2004 | Herrmann et al. | |
| 2004/0202684 A1 | 10/2004 | Djerassi | |
| 2004/0220260 A1 | 11/2004 | Cals-Grierson | |
| 2004/0265244 A1 | 12/2004 | Rosen | |
| 2005/0038473 A1 | 2/2005 | Tamarkin et al. | |
| 2005/0232869 A1 | 10/2005 | Tamarkin et al. | |
| 2005/0271596 A1 | 12/2005 | Friedman et al. | |
| 2006/0159734 A1 | 7/2006 | Shudo | |
| 2006/0160897 A1 | 7/2006 | Pelicci et al. | |
| 2006/0173076 A1 | 8/2006 | Vishnupad et al. | |
| 2006/0269620 A1 | 11/2006 | Morris et al. | |
| 2006/0275218 A1 | 12/2006 | Tamarkin et al. | |
| 2007/0166255 A1 | 7/2007 | Gupta | |
| 2007/0243224 A1 | 10/2007 | Ludwig et al. | |
| 2007/0292359 A1 | 12/2007 | Friedman et al. | |
| 2007/0292461 A1 | 12/2007 | Tamarkin et al. | |
| 2008/0031907 A1 | 2/2008 | Tamarkin et al. | |
| 2008/0044444 A1 | 2/2008 | Tamarkin et al. | |
| 2008/0063607 A1 | 3/2008 | Tamarkin et al. | |
| 2008/0069779 A1 | 3/2008 | Tamarkin et al. | |
| 2008/0071206 A1 | 3/2008 | Peters | |
| 2008/0138296 A1 | 6/2008 | Tamarkin et al. | |
| 2008/0152596 A1 | 6/2008 | Friedman et al. | |
| 2008/0166303 A1 | 7/2008 | Tamarkin et al. | |
| 2008/0206155 A1 | 8/2008 | Tamarkin et al. | |
| 2008/0206159 A1 | 8/2008 | Tamarkin et al. | |
| 2008/0206161 A1 | 8/2008 | Tamarkin et al. | |
| 2008/0253973 A1 | 10/2008 | Tamarkin et al. | |
| 2008/0260655 A1 | 10/2008 | Tamarkin et al. | |
| 2008/0292560 A1 | 11/2008 | Tamarkin et al. | |
| 2008/0299220 A1 | 12/2008 | Tamarkin et al. | |
| 2008/0311163 A1 | 12/2008 | Peters | |
| 2008/0317679 A1 | 12/2008 | Tamarkin et al. | |
| 2009/0041680 A1 | 2/2009 | Tamarkin et al. | |
| 2009/0068118 A1 | 3/2009 | Eini et al. | |
| 2009/0068248 A1 | 3/2009 | Waterhouse et al. | |
| 2009/0130029 A1 | 5/2009 | Tamarkin et al. | |
| 2009/0170989 A1 | 7/2009 | Steele et al. | |
| 2009/0175799 A1 | 7/2009 | Tamarkin et al. | |
| 2009/0214618 A1 | 8/2009 | Schoenfisch et al. | |
| 2009/0226380 A1 | 9/2009 | Clark et al. | |
| 2009/0297634 A1 | 12/2009 | Friedman et al. | |
| 2010/0098733 A1 | 4/2010 | Stasko | |
| 2010/0215775 A1 | 8/2010 | Schmaus et al. | |
| 2010/0221195 A1 | 9/2010 | Tamarkin et al. | |
| 2010/0266510 A1 | 10/2010 | Tamarkin et al. | |
| 2010/0286285 A1 | 11/2010 | Barthez et al. | |
| 2010/0310476 A1 | 12/2010 | Tamarkin et al. | |
| 2010/0331968 A1 | 12/2010 | Morris et al. | |
| 2011/0027369 A1 | 2/2011 | Franke | |
| 2011/0045037 A1 | 2/2011 | Tamarkin et al. | |
| 2011/0052650 A1 | 3/2011 | Morris et al. | |
| 2011/0082167 A1 | 4/2011 | Pisak et al. | |
| 2011/0086234 A1 | 4/2011 | Stasko et al. | |
| 2011/0097279 A1 | 4/2011 | Tamarkin et al. | |
| 2011/0212033 A1 | 9/2011 | Tamarkin et al. | |
| 2011/0263526 A1 | 10/2011 | Satyam | |
| 2012/0021055 A1 | 1/2012 | Schoenfisch et al. | |
| 2012/0114547 A1 | 5/2012 | Smith | |
| 2012/0134951 A1* | 5/2012 | Stasko | A61K 31/655 424/78.06 |
| 2012/0136323 A1 | 5/2012 | Stasko et al. | |
| 2012/0141384 A1 | 6/2012 | Tamarkin et al. | |
| 2012/0156163 A1 | 6/2012 | Bauman et al. | |
| 2012/0230921 A1 | 9/2012 | Stasko | |
| 2012/0237453 A1 | 9/2012 | Tamarkin et al. | |
| 2013/0059017 A1 | 3/2013 | Perricone et al. | |
| 2013/0089629 A1 | 4/2013 | Beijer et al. | |
| 2013/0109756 A1 | 5/2013 | Huber et al. | |
| 2013/0164225 A1 | 6/2013 | Tamarkin et al. | |
| 2013/0189191 A1 | 7/2013 | Tamarkin et al. | |
| 2013/0189193 A1 | 7/2013 | Tamarkin et al. | |
| 2013/0189195 A1 | 7/2013 | Tamarkin et al. | |
| 2013/0310533 A1 | 11/2013 | Bao et al. | |
| 2013/0344334 A1 | 12/2013 | Schoenfisch et al. | |
| 2014/0017121 A1 | 1/2014 | Schoenfisch et al. | |
| 2014/0057001 A1 | 2/2014 | Bauman et al. | |
| 2014/0058124 A1 | 2/2014 | Schoenfisch et al. | |
| 2014/0065200 A1 | 3/2014 | Schoenfisch et al. | |
| 2014/0107071 A1 | 4/2014 | Kougoulos et al. | |
| 2014/0134321 A1 | 5/2014 | Stasko et al. | |
| 2014/0171395 A1 | 6/2014 | Schoenfisch et al. | |
| 2014/0193502 A1 | 7/2014 | Tamarkin et al. | |
| 2014/0242023 A1 | 8/2014 | Doxey et al. | |
| 2014/0248219 A1 | 9/2014 | Tamarkin et al. | |
| 2014/0255318 A1 | 9/2014 | Stasko et al. | |
| 2014/0271494 A1 | 9/2014 | Tamarkin et al. | |
| 2014/0369949 A1 | 12/2014 | Peters | |
| 2015/0017103 A1 | 1/2015 | Tamarkin et al. | |
| 2015/0024052 A1 | 1/2015 | Doxey | |
| 2015/0025060 A1 | 1/2015 | Tamarkin et al. | |
| 2015/0111973 A1 | 4/2015 | Bauman et al. | |
| 2015/0118164 A1 | 4/2015 | Tamarkin et al. | |
| 2015/0141606 A1 | 5/2015 | Bao et al. | |
| 2015/0182543 A1 | 7/2015 | Schoenfisch et al. | |
| 2015/0225488 A1 | 8/2015 | Schoenfisch et al. | |

FOREIGN PATENT DOCUMENTS

| | | | |
|---|---|---|---|
| EP | 1704876 A1 | 9/2006 | |
| EP | 1 707 224 A1 | 10/2006 | |
| EP | 1 861 130 B1 | 9/2008 | |
| EP | 1 871 433 B1 | 4/2009 | |
| EP | 1 846 058 B1 | 7/2009 | |
| EP | 2 119 459 A1 | 11/2009 | |
| EP | 2 142 179 A1 | 1/2010 | |
| EP | 2 142 181 A1 | 1/2010 | |
| EP | 1 917 005 B1 | 9/2010 | |
| GB | 2 354 441 | 3/2001 | |
| JP | H07-039748 | 2/1995 | |
| JP | 2002-531526 | 9/2002 | |
| JP | 2003-286153 | 10/2003 | |
| JP | 2008529626 A | 8/2008 | |
| JP | 2012-197300 | 10/2012 | |
| JP | 2014518282 A | 7/2014 | |
| WO | WO-9102538 A1 * | 3/1991 | A61K 8/65 |
| WO | WO 93/10754 A1 | 6/1993 | |
| WO | WO 96/13164 A1 | 5/1996 | |

(56) References Cited

FOREIGN PATENT DOCUMENTS

| WO | WO 96/15797 A1 | 5/1996 | |
|---|---|---|---|
| WO | WO 98/05689 A1 | 2/1998 | |
| WO | WO 00/002593 A2 | 1/2000 | |
| WO | WO 00/33877 A1 | 6/2000 | |
| WO | WO 00/49993 A2 | 8/2000 | |
| WO | WO 01/21148 A1 | 3/2001 | |
| WO | WO 01/26702 A2 | 4/2001 | |
| WO | WO 01/85013 A2 | 11/2001 | |
| WO | WO 02/020026 A2 | 3/2002 | |
| WO | WO 02/41902 A1 | 5/2002 | |
| WO | WO 02/056864 A2 | 7/2002 | |
| WO | WO 03/013489 A1 | 2/2003 | |
| WO | WO 03/072039 A2 | 9/2003 | |
| WO | WO 03/078437 A1 | 9/2003 | |
| WO | WO 03/086282 A2 | 10/2003 | |
| WO | WO 03/092763 A1 | 11/2003 | |
| WO | WO 2004/012659 A2 | 2/2004 | |
| WO | WO 2004/012874 A1 | 2/2004 | |
| WO | WO 2004/098538 A2 | 11/2004 | |
| WO | WO 2005/003032 A1 | 1/2005 | |
| WO | WO 2005/004984 A1 | 1/2005 | |
| WO | WO 2005/011575 A2 | 2/2005 | |
| WO | WO 2005/037339 A1 | 4/2005 | |
| WO | WO 2005/046661 A2 | 5/2005 | |
| WO | WO 2006/084910 A2 | 8/2006 | |
| WO | WO 2006/084912 A1 | 8/2006 | |
| WO | WO 2006/100154 A1 | 9/2006 | |
| WO | WO 2006/128121 A2 | 11/2006 | |
| WO | WO 2006/138035 A1 | 12/2006 | |
| WO | WO 2007/007208 A2 | 1/2007 | |
| WO | WO 2007/023005 A1 | 3/2007 | |
| WO | WO 2007/023396 A2 | 3/2007 | |
| WO | WO 2007/054818 A2 | 5/2007 | |
| WO | WO 2007/085254 A1 | 8/2007 | |
| WO | WO 2008/032212 A2 | 3/2008 | |
| WO | WO 2008/038140 A2 | 4/2008 | |
| WO | WO 2008/038147 A2 | 4/2008 | |
| WO | WO 2008/110872 A2 | 9/2008 | |
| WO | WO 2008/116497 A1 | 10/2008 | |
| WO | WO 2008/116925 A1 | 10/2008 | |
| WO | WO 2008/152444 A2 | 12/2008 | |
| WO | WO 2009/007785 A2 | 1/2009 | |
| WO | WO 2009/049208 A1 | 4/2009 | |
| WO | WO 2009/056991 A2 | 5/2009 | |
| WO | WO 2009/067095 A1 | 5/2009 | |
| WO | WO 2009/072007 A2 | 6/2009 | |
| WO | WO 2009/087578 A2 | 7/2009 | |
| WO | WO 2009/090495 A2 | 7/2009 | |
| WO | WO 2009/098595 A2 | 8/2009 | |
| WO | WO 2009/131931 A1 | 10/2009 | |
| WO | WO 2011/005846 A1 | 1/2011 | |
| WO | WO 2011/022652 A1 | 2/2011 | |
| WO | WO 2011/022680 A2 | 2/2011 | |
| WO | WO 2011/061519 A2 | 5/2011 | |
| WO | WO 2011/073998 A1 | 6/2011 | |
| WO | 2012078649 | 6/2012 | |
| WO | WO 2012/100174 A1 | 7/2012 | |
| WO | WO 2012/153331 A2 | 11/2012 | |
| WO | WO 2013/006608 A1 | 1/2013 | |
| WO | WO 2013/006613 A1 | 1/2013 | |
| WO | WO-2013006613 A1 * | 1/2013 | .......... A61K 9/0014 |
| WO | WO 2013/029009 A1 | 2/2013 | |
| WO | WO 2013/138073 A1 | 9/2013 | |
| WO | WO 2013/138075 A1 | 9/2013 | |
| WO | 2014134502 | 9/2014 | |
| WO | 2015021382 | 2/2015 | |
| WO | WO-2015021382 A2 * | 2/2015 | ............ A61K 8/345 |
| WO | WO 2016/007834 A1 | 1/2016 | |
| WO | WO 2016/010988 A1 | 1/2016 | |
| WO | WO 2016/022170 A1 | 2/2016 | |
| WO | WO 2016/160089 A1 | 10/2016 | |
| WO | WO 2017/019614 A1 | 2/2017 | |
| WO | WO 2018/236803 A1 | 12/2018 | |
| WO | WO 2018/236806 A1 | 12/2018 | |

OTHER PUBLICATIONS

Amadeu et al. "Nitric Oxide Donor Improves Healing if Applied on Inflammatory and Proliferative Phase" *Journal of Surgical Research* 149:84-93 (2008).

Blos et al. "Organ-specific and stage-dependent control of *Leishmania* major infection by inducible nitric oxide synthase and phagocyte NADPH oxidase" *European Journal of Immunology* 33:1224-1234 (2003).

Bohl-Masters et al. "Effects of nitric oxide releasing poly(vinyl alcohol) hydrogel dressings on dermal wound healing in diabetic mice" *Wound Repair and Regeneration* 10(5):286-294 (2002).

Boykin et al. "HBO Mediates Increased Nitric Oxide Production Associated With Wound Healing" *Wound Repaid and Regeneration* 12(2):A15 (Abstract 054) (2004).

Brunet, L. R. "Nitric oxide in parasitic infections" *International Immunopharmacology* 1(8):1457-1467 (2001) (Abstract only).

Butsch et al. "Topical treatment with a two-component gel releasing nitric oxide cures C57BL/6 mice from cutaneous leishmaniasis caused by *Leishmania major*" Experimental Dermatology 25(11):914-916 (2016).

Costa et al. "S-nitrosoglutathione (GSNO) is cytotoxic to intracellular amastigotes and promotes healing of topically treated *Leishmania major* or *Leishmania braziliensis* skin lesions" *Journal of Antimicrobial Chemotherapy* 68:2561-2568 (2013).

Das et al. "Modulation of the Arginase Pathway in the Context of Microbial Pathogenesis: A Metabolic Enzyme Moonlighting as an Immune Modulator" *PloS Pathogens* 6(6):e1000899 (2010).

De Groote et al. "No Inhibitions: Antimicrobial Properties of Nitric Oxide" *Clinical Infectious Diseases* 21(Supplement 2):S162-S165 (1995).

Del Rosso, James Q. "The Role of Topical Antifungal Therapy for Onychomycosis and the Emergence of Newer Agents" *The Journal of Clinical Aesthetic Dermatology* 7(7):10-18 (2014).

Deppisch et al. "Gaseous nitric oxide to treat antibiotic resistant bacterial and fungal lung infections in patients with cystic fibrosis: a phase I clinical study" *Infection* 44:513-520 (2016).

Elewski et al. "Onychomycosis caused by *Scytalidium dimidiatum*" *Journal of the American Academy of Dermatology* 35(2), Part 2:336-338 (1996).

Elewski et al. "Efficacy and safety of tavaborole topical solution, 5%, a novel boron-based antifungal agent, for the treatment of toenail onychomycosis: Results from 2 randomized phase-III studies" *Journal of the American Academy of Dermatology* 73(1):62-69 (2015).

Fang, Ferric C. "Mechanisms of Nitric Oxide-related Antimicrobial Activity" *Journal of Clinical Investigation* 99(12):2818-2825 (1997).

Fang, Ferric C. "Antimicrobial reactive oxygen and nitrogen species: concepts and controversies" *Nature Reviews Microbiology* 2(10):820-832 (2004) (Abstract only).

Feelisch, M. "The Biochemical Pathways of Nitric Oxide Formation from Nitrovasodilators: Appropriate Choice of Exogenous NO Donors and Aspects of Preparation and Handling of Aqueous NO Solutions" *Journal of Cardiovascular Pharmacology* 17(Suppl. 3):S25-S33 (1991).

Finnen et al. "Topical application of acidified nitrite to the nail renders it antifungal and causes nitrosation of cysteine groups in the nail plate" *The British Journal of Dermatology* 157(3):494-500 (2007) (Abstract only).

Foster et al. "Epidemiologic surveillance of cutaneous fungal infection in the United States from 1999 to 2002" *Journal of the American Academy of Dermatology* 50(5):748-752 (2004) (Abstract only).

Ghaffari et al. "Potential application of gaseous nitric oxide as a topical antimicrobial agent" *Nitric Oxide* 14:21-29 (2006).

Ghannoum et al. "Antifungal Agents: Mode of Action, Mechanisms of Resistance, and Correlation of These Mechanisms with Bacterial Resistance" *Clinical Microbiology Reviews* 12(4):501-517 (1999).

Gupta et al. "Oral antifungal agents for onychomycosis" *The Lancet* 351(9102):p. 541-542 (1998) (Abstract only).

Gupta et al. "Recurrences of Dermatophyte Toenail Onychomycosis during Long-Term Follow-up after Successful Treatments with

(56) References Cited

OTHER PUBLICATIONS

Mono- and Combined Therapy of Terbinafine and Itraconazole" *Journal of Cutaneous Medicine and Surgery* 17(3):201-206 (2013).
Gupta et al. "The efficacy and safety of efinaconazole 10% solution for treatment of mild to moderate onychomycosis: a pooled analysis of two phase 3 randomized trials" *Journal of Drugs in Dermatology* 13(7):815-820 (2014) (Abstract only).
Hetrick et al. "Anti-biofilm efficacy of nitric oxide-releasing silica nanoparticles" *Biomaterials* 30:2782-2789 (2009).
Hrabie et al. "Chemistry of the Nitric Oxide-Releasing Diazeniumdiolate ("Nitrosohydroxylamine") Functional Group and Its Oxygen-Substituted Derivatives" *Chemical Reviews* 102:1135-1154 (2002).
Hui et al. "In vitro penetration of a novel oxaborole antifungal (AN2690) into the human nail plate" *Journal of Pharmaceutical Sciences* 96(10):2622-2631 (2007) (Abstract only).
International Preliminary Report on Patentability corresponding to International Patent Application No. PCT/US2017/027333 (8 pages) (dated Oct. 25, 2018).
Kandavilli et al. "Polymers in Transdermal Drug Delivery Systems" *Pharmaceutical Technology* pp. 62-80 (2002).
Kelly, Brendan P. "Superficial Fungal Infections" *Pediatrics in Review* 33(4):e22-e37 (2012) (Abstract only).
Lacroix et al. "In vitro activity of amphotericin B, itraconazole, voriconazole, posaconazole, caspofungin and terbinafine against *Scytalidium dimidiatum* and *Scytalidium hyalinum* clinical isolates" *Journal of Antimicrobial Chemotherapy* 61:835-837 (2008).
Liew et al. "Cytokines and nitric oxide as effector molecules against parasitic infections" *Philosophical Transactions of the Royal Society of London, Series B, Biological Sciences* 352(1359):1311-1315 (1997).
Lipner et al. "Management of Onychomycosis and Co-Existing Tinea Pedis" *Journal of Drugs in Dermatology* 14(5):492-494 (2015) (Abstract only).
Markinson et al. "Efinaconazole Topical Solution, 10% Efficacy in Patients with Onychomycosis and Coexisting Tinea Pedis" *Journal of the American Podiatric Medical Association* 105(5):407-411 (2015) (Abstract only).
McHale et al. "In Vitro Nail Penetration of Nitric Oxide-releasing Formulations for the Topical Treatment of Onychomycosis" *Microbe Poster*—www.novantherapeutics.com (1 page) (2016).
Miller et al. "Gaseous nitric oxide bactericidal activity retained during intermittent high-dose short duration exposure" *Nitric Oxide* 20(1):16-23 (2009) (Abstract only).
Nathan et al. "Reactive oxygen and nitrogen intermediates in the relationship between mammalian hosts and microbial pathogens" *Proceedings of the National Academy of Sciences USA* 97(16):8841-8848 (2000).
Netea et al. "An integrated model of the recognition of *Candida albicans* by the innate immune system" *Nature Reviews Microbiology* 6:67-78 (2008).
Novan, Inc. Press Release "Novan Announces First Patient Dosed in Phase 2 Anti-Fungal Program" http://investors.novan.com/node/6616/pdf (2 pages) (Jul. 21, 2016).
Novan, Inc. Press Release "Novan Reports Positive Topline Results with SB208 in Phase 2 Trial" http://investors.novan.com/node/6706/pdf (2 pages) (Apr. 12, 2017).
Novan, Inc. Press Release "Novan to Present Positive Phase 2 Results for SB208 Antifungal Program at Winter Clinical Dermatology Conference" http://investors.novan.com/node/6791/pdf (2 pages) (Jan. 11, 2018).
Novan, Inc. Press Release "SB208 Increases Daily Nail Growth Rate over Four Weeks of Treatment" http://investors.novan.com/node/6831/pdf (2 pages) (May 17, 2018).
Opländer et al. "Dermal Nitrite Application: An Update" *Journal of Investigative Dermatology* 131:1763-1765 (2011).
Opländer et al. "Dermal application of nitric oxide in vivo: kinetics, biological responses, and therapeutic potential in humans" *Clinical Pharmacology and Therapeutics* 91(6):1074-1082 (2012) (Abstract only).
Ormerod et al. "An observational prospective study of topical acidified nitrite for killing methicillin-resistant *Staphylococcus aureus*(MRSA) in contaminated wounds" *BMC Research Notes* 4(458):1-7 (2011).
Pacher et al. "Nitric Oxide and Peroxynitrite in Health and Disease" *Physiological Reviews* 87(1):315-424 (2007).
Peyrot et al. English Machine Translation of International Patent Application Publication No. WO 2000/002593 *Espacenet*(6 pages) (Retrieved on Sep. 27, 2016).
Privett et al. "Examination of Bacterial Resistance to Exogenous Nitric Oxide" *Nitric Oxide* 26(3):169-173 (2012).
Pulfer et al. "Incorporation of nitric oxide-releasing crosslinked polyethyleneimine microspheres into vascular grafts" *Journal of Biomedical Materials Research* 37:182-189 (1997).
Regev-Shoshani et al. "A nitric oxide-releasing solution as a potential treatment for fungi associated with tinea pedis" *Journal of Applied Microbiology* 114(2):536-544 (2013).
Reiner et al. "The Regulation of Immunity to *Leishmania major*" *Annual Review of Immunology* 13:151-177 (1995).
Sangster, James "Octanol-Water Partition Coefficients of Simple Organic Compounds" *Journal of Physical and Chemical Reference Data* 18(3):1111-1227 (1989).
Scher, Richard K. "Onychomycosis: therapeutic update" *Journal of the American Academy of Dermatology* 40(6 suppl.):S21-S26 (1999) (Abstract only).
Scher et al. "Onychomycosis in clinical practice: factors contributing to recurrence" *The British Journal of Dermatology* 149(Suppl. 65):5-9 (2003) (Abstract only).
Shin et al. "Synthesis of Nitric Oxide-releasing Silica Nanoparticles" *Journal of the American Chemical Society* 129:4612-4619 (2007).
Singh et al. "Film Formers Gels (FIFOGE): A Novel Approach" *Guru Drone Journal of Pharmacy& Research* 1(1):22-28 (2013).
Smith et al. "Transdermal delivery of nitric oxide from diazeniumdiolates" *Journal of Controlled Release* 51:153-159 (1998).
Stasko et al. "Nitric Oxide-Releasing Macromolecule Exhibits Broad-Spectrum Antifungal Activity and Utility as a Topical Treatment for Superficial Fungal Infections" *Antimicrobial Agents and Chemotherapy* 62(7):e01026-17 (2018).
Stevens et al. "Nitric Oxide-Releasing Silica Nanoparticle Inhibition of Ovarian Cancer Cell Growth" *Molecular Pharmaceutics* 7(3):775-785 (2010).
Stricker-Krongrad et al. "The importance of minipigs in dermal safety assessment: an overview" *Cutaneous and Ocular Toxicology* 36(2):105-113 (2017).
Traynor et al. "Effect of a novel penetration enhancer on the ungual permeation of two antifungal agents" *The Journal of Pharmacy and Pharmacology* 62(6):730-737 (2010) (Abstract only).
Tucker et al. "Effect of nitric-oxide-generating system on microcirculatory blood flow in skin of patients with severe Raynaud's syndrome: a randomised trial" *The Lancet* 354(9191):1670-1675 (1999) (Abstract only).
Van Assche et al. "Leishmania-macrophage interactions: insights into the redox biology" *Free Radical Biology and Medicine* 51(2):337-351 (2011) (Abstract only).
Wang et al. "Nitric Oxide Donors: Chemical Activities and Biological Applications" *Chemical Reviews* 102:1091-1134 (2002).
Weller et al. "Antimicrobial effect of acidified nitrite on dermatophyte fungi, *Candida* and bacterial skin pathogens" *Journal of Applied Microbiology* 90(4):648-652 (2001).
Extended European Search Report corresponding to European Patent Application No. 17783103.9 (10 pages) (dated Oct. 7, 2019).
English translation of Notice of Reasons of Refusal corresponding to Japanese Patent Application No. 2018-554075 (5 pages) (dated Feb. 2, 2021).

* cited by examiner

COMPOSITIONS, SYSTEMS, KITS, AND METHODS FOR TREATING AN INFECTION

RELATED APPLICATION INFORMATION

This application is a 35 U.S.C. § 371 national stage application of International Application No. PCT/US2017/027333, filed Apr. 13, 2017, which claims the benefit of U.S. Provisional Patent Application Ser. Nos. 62/322,064, filed Apr. 13, 2016, 62/356,891, filed Jun. 30, 2016, and 62/484,252, filed Apr. 11, 2017, the disclosure of each of which is incorporated herein by reference in its entirety.

FIELD

The present invention relates generally to compositions, systems, kits, and methods for treating an infection, such as, for example, a viral, bacterial, protozoan, and/or fungal (e.g., onychomycosis and/or *Tinea pedis*) infection.

BACKGROUND

Fungi can be difficult to kill. Accordingly, fungal infections of the skin and/or nail can be difficult to treat and reoccurrence can be a common problem. In addition, fungal infections can often infect both the skin and the nail, which may result in the need for two different medications and/or treatment regimens. This can reduce patient compliance and can thereby reduce the likelihood of a positive clinical outcome.

SUMMARY

A first aspect of the present invention is directed to a method of treating and/or preventing a viral, bacterial, protozoan, and/or fungal infection in and/or on a subject, the method comprising administering a composition comprising a nitric oxide (NO)-releasing macromolecule to the subject, wherein the composition delivers a total amount of NO of at least about 50 or 100 nmol of NO/mg of the composition at about 1, 2, 3, 4, 5, 6, 7, 8, 9, or 10 minutes after an initial time point as measured by in vitro release, thereby treating and/or preventing the viral, bacterial, protozoan, and/or fungal infection in and/or on the subject. In some embodiments, the composition delivers a total amount of NO of about 50 or 100 to about 1000 nmol of NO/mg of the composition at about 1, 3, 5, 10, 20, 30, 40, or 50 minute(s) or 1, 2, 3, 4, 5, 6, 7, or 8 hour(s) as measured by in vitro release. In some embodiments, the composition has a half life of nitric oxide release of about 2 minutes to about 10 minutes or about 30 minutes to about 1 hour.

A further aspect of the present invention is directed to a composition including a viscosity increasing agent present in an amount of about 0.1% to about 10% by weight of the composition, an emollient present in an amount of about 1% to about 30% by weight of the composition, a humectant present in an amount of about 1% to about 30% by weight of the composition, a solvent present in an amount of about 1% to about 20% by weight of the composition, and a co-solvent present in an amount of about 1% to about 50% by weight of the composition. In some embodiments, the composition may have a shelf life of at least 3 months or more e.g., 6, 9, 12, 18, or 24 months or more).

A further aspect of the present invention is directed to a composition including a thickening agent present in an amount of about 0.1% to about 25% by weight of the composition, water present in an amount of about 50% to about 99% by weight of the composition, and a cosolvent present in an amount of about 0.1% to about 15% by weight of the composition.

Another aspect of the present invention is directed to an admixture including a first composition of the present invention (e.g., a hydrogel); and a second composition of the present invention (e.g., an anhydrous gel). In some embodiments, the admixture may be film-forming. The admixture may be applied to the nail and/or skin of a subject and/or may be suitable and/or configured for application to the nail and/or skin of a subject. In some embodiments, the admixture may have a shelf life of at least 3 months or more (e.g., 6, 9, 12, 18, or 24 months or more).

A further aspect of the present invention is directed to a kit including a first composition of the present invention (e.g., a hydrogel); and a second composition of the present invention an anhydrous gel). In some embodiments, the kit may form an admixture upon dispensing the first composition and second composition. In some embodiments, the kit may have a shelf life of at least 3 months or more (e.g., 6, 9, 12, 18, or 24 months or more).

Another aspect of the present invention is directed to a packaged composition including a first composition of the present invention (e.g., a hydrogel); and a second composition of the present invention (e.g., an anhydrous gel). In some embodiments, the packaged composition may have a shelf life of at least 3 months or more (e.g., 6, 9, 12, 18, or 24 months or more).

A further aspect of the present invention is directed to a method of treating and/or preventing a viral, bacterial, protozoan, and/or fungal (e.g., onychomycosis and/or *Tinea pedis*) infection in a subject, the method including administering a composition of the present invention to the subject, thereby treating and/or preventing the viral, bacterial, protozoan, and/or fungal (e.g., onychomycosis and/or *Tinea pedis*) infection in the subject. In some embodiments, the composition may be administered to the nail and/or skin of a subject and/or may be suitable and/or configured for application to the nail and/or skin of a subject. In some embodiments, the composition may be suitable to treat and/or prevent a fungal infection of the nail and skin of the subject, such as, for example, the composition may treat and/or prevent onychomycosis and *Tinea pedis*.

Another aspect of the present invention is directed to a method of increasing the release of nitric oxide from an anhydrous topical gel comprising a diazeniumdiolate modified macromolecule, the method including contacting the anhydrous topical gel with a hydrogel of the present invention to provide an admixture; and applying the admixture to the skin of a subject. In some embodiments, the admixture may be administered to the nail and/or skin of a subject and/or may be suitable and/or configured for application to the nail and/or skin of a subject. In some embodiments, the admixture may be suitable to treat and/or prevent a fungal infection of the nail and skin of the subject, such as, for example, the admixture may treat and/or prevent onychomycosis and *Tinea pedis*.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION

Figure 1:
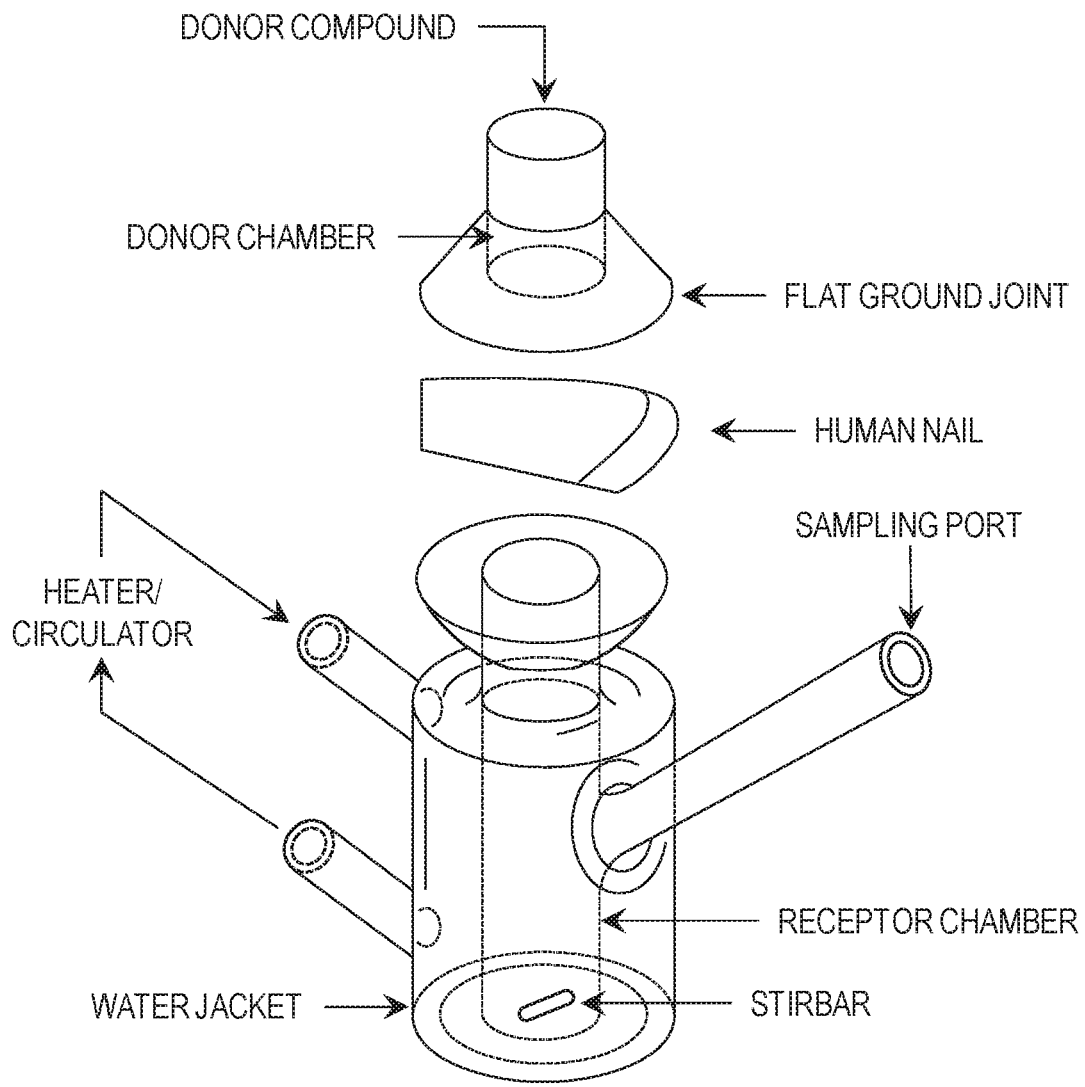
FIG. 1 is a diagram of a standard vertical diffusion cell.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re *Herz*, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value, such as an amount or concentration and the like, is meant to refer to variations of up to ±20% of the specified value, such as, but not limited to, ±10%, ±5%, ±1%, ±0.5%, or even ±0.1% of the specified value, as well as the specified value. For example, "about X" where X is the measurable value, is meant to include X as well as variations of ±20%, ±10%, ±5%, ±1%, ±0.5%, or even ±0.1% of X. A range provided herein for a measureable value may include any other range and/or individual value therein.

Provided herein are compositions, systems, kits, and/or methods for treating and/or preventing a viral, bacterial, protozoan, and/or fungal infection in and/or on a subject. In some embodiments, a composition, system, kit, and/or method of the present invention may treat and/or prevent a topical viral, bacterial, protozoan, and/or fungal infection in and/or on a subject. In some embodiments, a composition, system, kit, and/or method of the present invention may treat and/or prevent onychomycosis and/or *Tinea pedis*. In some embodiments, a composition of the present invention may be antimicrobial (e.g., antiviral, antibacterial, and/or antifungal). In some embodiments, a composition, system, kit, and/or method of the present invention may treat and/or prevent a microbial infection in and/or on the skin and/or nail of a subject.

In some embodiments, a method of the present invention comprises administering a composition comprising a NO-releasing compound (e.g., a NO-releasing macromolecule, such as, e.g., a co-condensed silica particle prepared from diazeniumdiolated methylaminopropyl trimethoxysilane (MAP3) and tetra methyl orthosilicate (TMOS)). The composition may provide a particular release pattern for nitric oxide. All releases of nitric oxide described herein, including those described with regard to a time period after administration to a subject, are referenced with respect to real time in vitro release testing. The in vivo release of nitric oxide (e.g., the nitric oxide release when the composition is applied to a subject) may vary with the subject to which the composition is applied. In some embodiments, the in vivo release of nitric oxide may vary depending on the particular composition. However, it is believed that differences in the in vitro release will be similarly reflected in the in vivo release of nitric oxide. Accordingly, for clarity, unless specifically stated that the nitric oxide release is when applied to a subject, references to nitric oxide release with regard to embodiments of the compositions of the present invention will be with reference to the in vitro release of nitric oxide. Time point zero or the initial time point of the in vitro release testing may be correlated to the time of administration to a subject with all subsequent real-time points corresponding to a certain time after administration. In some embodiments, when a composition is measured in vitro, formation of the composition (e.g., combination of two or more compositions to form an admixture) may be used as equivalent or comparative in time to administration of the composition to a subject. In some embodiments, nitric oxide release may be determined using a chemiluminescent nitric oxide analyzer.

In some embodiments, the composition may release a total amount of NO of at least about 50 or 100 nmol of NO/mg of the composition at about 1, 2, 3, 4, 5, 6, 7, 8, 9, or 10 minutes after an initial time point (e.g., after formation of the composition and/or administration to a subject) as measured by in vitro release. In some embodiments, the composition may release a total amount of NO of at least about 300, 400, or 500 nmol of NO/mg of the composition at about 1, 2, 3, 4, 5, 6, 7, 8, 9, or 10 minutes after an initial time point as measured by in vitro release. In some embodiments, the composition may release a total amount of NO of about 50 or 100 to about 1000 nmol of NO/mg of the composition at about 1, 3, 5, 10, 20, 30, 40, or 50 minute(s) or 1, 2, 3, 4, 5, 6, 7, or 8 hour(s) after an initial time point as measured by in vitro release. In some embodiments, the composition may release, on average, a total amount of NO of about 50, 100, 150, 200, 250, 300, 350, 400, 450, 500, 550, 600, 650, 700, 750, 800, 850, 900, 950, 1000, or more nmol of NO/mg of the composition at about 1, 3, 5, 10, 20, 30, 40, or 50 minute(s) or 1, 2, 3, 4, 5, 6, 7, or 8 hour(s) after an initial time point as measured by in vitro release.

In some embodiments, the composition may release a total amount of NO of at least about 100, 150, or 200 nmol of NO/mg of the composition at about 5, 6, 7, 8, 9, 10, 11, 12, 13, 14, or 15 minutes after an initial time point as measured by in vitro release. In some embodiments, the composition may release a total amount of NO of about 100 to about 500 nmol of NO/mg of the composition at about 5, 6, 7, 8, 9, 10, 11, 12, 13, 14, or 15 minutes after an initial time point as measured by in vitro release. In some embodiments, the composition may release a total amount of NO of about 150 to about 400 nmol of NO/mg of the composition at about 5, 6, 7, 8, 9, 10, 11, 12, 13, 14, or 15 minutes after an initial time point as measured by in vitro release.

In some embodiments, the composition may release, on average, a total amount of NO of about 50 to about 300 or about 300 to about 500 nmol of NO/mg of the composition at about 30 minutes as measured by in vitro release. In some embodiments, the composition may release, on average, a total amount of NO of about 200 to about 600 nmol of NO/mg of the composition at about 1 hour as measured by in vitro release. In some embodiments, the composition may release, on average, a total amount of NO of about 200 to about 800 nmol of NO/mg of the composition at about 4 hours as measured by in vitro release. In some embodiments, the composition may release, on average, a total amount of NO of about 200 to about 1000 nmol of NO/mg of the composition at about 8 hours as measured by in vitro release.

In some embodiments, a composition of the present invention maintains a real time concentration of NO of at least about 0.2, 0.3, 0.4, 0.5, 0.6, 0.7, 0.8, or 1 µmol of NO/mg of the composition for at least about 4, 5, 6, 7, 8, 9, or 10 hours as measured by in vitro release. In some embodiments, the composition maintains a real time concentration of NO of at least about 50 µmol of NO/mg of the composition at about 1 to about 5 minutes after the initial time point (e.g., after formation of the composition and/or administration to a subject) as measured by in vitro release. In some embodiments, the composition maintains a real time concentration of NO in a range of about 50 to about 1500 µmol of NO/mg of the composition at about 1 to about 5 minutes after the initial time point as measured by in vitro release.

In some embodiments, a composition of the present invention provides a maximum concentration (Cmax) of NO released of greater than 400, 800, 1000, or 1500 µmol of NO/mg of the composition based on a total NO release determined at 8, 10, 12, or 24 hours measured by in vitro release. In some embodiments, the composition may provide a Cmax of NO released of about 400, 500, 600, 700, 800, 900, 1000, 1100, 1200, 1300, 1400, 1500, 1600, 1700, 1800, 1900, 2000, 2100, 2200, 2300, 2400, 2500, 3000, 3500 µmol of NO/mg or more based on a total NO release determined at 8, 10, 12, or 24 hours measured by in vitro release. In some embodiments, the Cmax occurs within about 10, 9, 8, 7, 6, 5, 4, 3, 2, or 1 minute(s) or 45 or 30 seconds of the initial time point. In some embodiments, the Cmax occurs at about 30 seconds to about 2, 3, 4 or 5 minutes after an initial time point and the Cmax may be at least about 400, 800, 1000, or 1500 µmol of NO/mg of the composition based on a total NO release determined at 8, 10, 12, or 24 hours and measured by in vitro release.

In some embodiments, a composition of the present invention has a half life of nitric oxide release of at least about 1 or 2 minutes based on a total NO release determined at 8, 10, 12, or 24 hours and measured by in vitro release. A half life of nitric oxide release is achieved by determining the time at which half the amount of the total NO released from the composition after a period of time is released. In some embodiments, a composition of the present invention has a half life of nitric oxide release of about 1, 2, 3, 4, 5, 6, 7, 8, 9, 10, 15, 20, 2, 30, 35, 40, 45, 50, 55, or 60 minutes based on a total NO release determined at 8, 10, 12, or 24 hours and measured by in vitro release. In some embodiments, a composition of the present invention has a half life of nitric oxide release of about 2 minutes to about 10 minutes or about 30 minutes to about 1 hour based on a total NO release determined at 8, 10, 12, or 24 hours and measured by in vitro release.

A composition of the present invention may be a topical composition (e.g., a topical antimicrobial composition). In some embodiments, a composition of the present invention may be a film-forming composition, such as, for example, a film-forming gel. In some embodiments, a composition of the present invention may be a gel prior to administration to the skin and/or nail of a subject e.g., during storage) and/or during administration to the skin and/or nail of a subject, and the composition may convert and/or transform to a film during administration to the skin and/or nail of a subject and/or after being applied to the skin and/or nail of a subject. In some embodiments, the primary formulation of a composition of the present invention is a gel and the secondary formulation is a film, which may provide longer contact time with the nail and/or skin of a subject and/or may provide for a longer therapeutic delivery of the composition and/or API. In some embodiments, a film formed by a composition of the present invention may create a barrier that may cause API release into the skin and/or nail of a subject, which may provide for greater or improved penetration of the composition and/or API into the skin and/or nail of the subject. The film may be an occlusive layer that may direct API release into the skin and/or nail of the subject. In some embodiments, a composition of the present invention may be applied to the nail and/or skin of a subject and/or may be suitable and/or configured for application to the nail and/or skin of a subject. In some embodiments, the composition may be suitable and/or configured to treat and/or prevent a viral, bacterial, protozoan, and/or fungal infection of the nail and skin of the subject, such as, for example, the composition may treat and/or prevent onychomycosis and *Tinea*

*pedis*. A system and/or kit of the present invention may comprise a composition of the present invention.

In some embodiments, a composition of the present invention may comprise a first part and/or phase comprising a first composition and a second part and/or phase comprising a second composition. In some embodiments, a composition of the present invention may be an admixture. "Admixture" as used herein refers to a composition of the present invention that is a combination of at least two different compositions. An admixture of the present invention may comprise at least two parts and/or phases that may correspond to the at least two different compositions. In some embodiments, the at least two different compositions may be miscible upon combination. In some embodiments, the term admixture refers to the at least two different compositions being maintained substantially isolated and/or separated from one another until the proximate time of use or application. In some embodiments, the term admixture refers to the at least two different compositions being maintained substantially isolated and/or separated from one another until dispensing, such as with pharmacist dispensed products. In some embodiments, one or more compositions that may be present in an admixture of the present invention may be maintained substantially isolated and/or separated from one or more other compositions that may be present in an admixture. The term admixture is not intended to refer to a composition that is created at the time of manufacture of the composition or product, such as by the combining of ingredients to create the composition.

The combining of two or more different compositions, such as, e.g., 2, 3, 4, 5, 6, 7, or more compositions, to form an admixture may be achieved by mixing, blending, contacting, applying to a same area or region, emulsifying, and/or the like the two or more different compositions. The combining of two or more different compositions may be carried out to induce a chemical reaction. A composition present in and/or used to form an admixture of the present invention may be different than another composition present in and/or used to form the admixture in the amount or concentration of one or more components, the type (e.g., chemical composition) of one or more components, and/or the presence and/or absence of one or more components.

An admixture of the present invention may comprise at least one composition that modulates a property of another composition and/or a component present in the admixture. The property modulated may be compared to the property of the composition and/or component in the absence of the admixture. For example, the admixture may comprise at least one composition (e.g., a first composition) that modulates the pH of another composition (e.g., a second composition) and/or the release of an active pharmaceutical ingredient (API) in another composition (e.g., a second composition). As used herein, release of the API refers to release of the API itself and/or release of one or more active agents from the API. For example, in embodiments where the API is a nitric oxide-releasing API, references to API release may refer to release of nitric oxide from the API. The pH of the admixture may be compared to the pH of the second composition when it is not in admixture with the first composition or vice versa. The release of the API from the admixture may be compared to the release of the API in the absence of the admixture e.g., the release of the individual API component and/or the release of the API from the second composition when the second composition is not in admixture with the first composition).

"Modulate," "modulating," "modulation," and grammatical variations thereof as used herein refer to an increase or reduction in a value or parameter. Modulate and grammatical variations thereof in reference to the pH of a second composition of the present invention and/or the release of an API in a second composition of the present invention refer to an increase or reduction compared to the pH of the second composition and/or the release of the API in the second composition in the absence of a first composition of the present invention. As used herein, the terms "increase," "increases," "increased," "increasing" and similar terms indicate an elevation in a value or parameter of at least about 5%, 10%, 25%, 50%, 75%, 100%, 150%, 200%, 300%, 400%, 500% or more, and, when used in reference to the pH and/or release of an API, refer to an elevation when compared to the pH and/or release in the absence of a first composition of the present invention. As used herein, the terms "reduce," "reduces," "reduced," "reduction" and similar terms refer to a decrease in a value or parameter of at least about 5%, 10%, 25%, 35%, 50%, 75%, 80%, 85%, 90%, 95%, 97% or more, and, when used in reference to the pH and/or release of an API, refer to a decrease when compared to the pH and/or release in the absence of a first composition of the present invention.

In some embodiments, an admixture may comprise at least two compositions (i.e., a first composition and a second composition). The first composition may modulate the pH of the second composition and/or the release of an API present in the second composition or vice versa. Admixtures comprising two compositions are described herein for purposes of illustration, but it is understood that the admixture may comprise more than two different compositions, such as, but not limited to, 2, 3, 4, 5, 6, 7, or more compositions. One or more of the compositions present in the admixture may modulate a property of another composition in the admixture. The property modulated may be the same property or a different property. In some embodiments, two or more different compositions in an admixture may together modulate a property of another composition in the admixture.

An admixture of the present invention may be formed by direct and/or indirect exposure of at least one component in a first composition to at least one component in a second composition. For example, an admixture may be formed by mixing and/or combining the first composition and second composition prior to, during, and/or after topical application to a subject. The admixture may comprise a single phase even though it may be prepared from at least two different compositions. A further example of direct exposure of a first composition and second composition to form an admixture may occur by applying one or more layers of the second composition onto a subject and then applying one or more layers of the first composition onto a subject or vice versa. Indirect exposure may occur by applying a second composition onto a subject and then applying a first composition onto a subject through a substrate, such as, but not limited to, a cloth, bandage, gauze, and the like, or vice versa, to form an admixture.

An admixture of the present invention may provide a particular release pattern for an API present in the admixture. The API release pattern may be determined by comparing the amount or concentration of API released over a period of time and/or the rate of release of an API from the admixture over a period of time. In some embodiments, the at least two different compositions present in the admixture are selected to provide a particular API release pattern. The API release pattern may be desirable for a particular infection, injury, disease, disorder, or treatment indication. In some embodiments, an admixture and/or two compositions of the present invention may provide and/or may be configured to provide a particular release pattern of an API present in the admixture. In some embodiments, an admixture and/or two compositions of the present invention may provide and/or may be configured to treat and/or prevent a viral, bacterial, protozoan, and/or fungal (e.g., onychomycosis and/or *Tinea pedis*) infection.

In some embodiments, the at least two different compositions present in the admixture may be selected to provide the admixture with a pH of less than about pH 11, such as, but not limited to, about 11, 10, 9, 8, 7, 6, 5, 4, 3, or less. In some embodiments, the at least two different compositions present in the admixture may be selected to provide the admixture with a pH of greater than about pH 3, such as, but not limited to, about 3, 4, 5, 6, 7, 8, 9, 10, 11, or more. In certain embodiments, the admixture pH may be between about pH 3 to about pH 11, such as, but not limited to, about pH 4 to about pH 9, about pH 7 to about pH 9, about pH 4 to about pH 8, pH 7 to about pH 10, about pH 4 to about pH 10, or about pH 5 to about pH 7. In some embodiments, at least one of the compositions present in the admixture may maintain the pH of the admixture in a particular pH range. The pH of the admixture may vary over time and this may cause the release rate of the API from the admixture to vary over time. For admixtures where the pH changes over time, the pH of the admixture may be measured within about 30 minutes after combination, in some embodiments, within about 10 minutes after combination, and in some embodiments, 2 minutes after combination. In some embodiments, the pH of the admixture may be measured at about 5 minutes, 30 minutes, 1 hour, and/or 24 hours after combination.

A composition of the present invention (e.g., an admixture) may provide for immediate release of the API from the composition and/or sustained release of the API from the composition. As used herein, immediate release refers to the release of 50% or more of the API within 4 hours of mixing and sustained release refers to the release of less than 50% of the API within 4 hours of mixing. In some embodiments, an admixture of the present invention may increase the amount of API released and/or the potency of an API present in at least one composition in the admixture by maintaining the pH of the admixture in a particular pH range compared to the release and/or potency of the API in the composition in the absence of the admixture. In some embodiments, the pH of the composition (e.g., admixture) is maintained below pH 9.

The API present in the composition may be released substantially continuously from the composition over a period of time. "Substantially continuously," and grammatical variants thereof as used herein refer to a release of an API from the composition for all or part of the time such that on average the release of the API confers an overall beneficial effect on the subject. Thus, there may be one or more short, intermittent and/or regular time periods in which the API is not being released, but the overall beneficial effect of the API on the subject remains. In some embodiments, the composition may provide an API release pattern that is substantially continuous over a period of time and may provide a therapeutically effective amount of the API over the period of time. In some embodiments, the amount of API released and/or the API release rate may vary over a period of time. In certain embodiments, the composition may comprise two or more (e.g., 2, 3, 4, 5 or more) release rates for the API.

The composition may provide an API release pattern that is substantially constant over a period of time. "Substantially constant" as used herein refers to a measureable value, such as the amount of API or the API release rate, on average, varying less than about 20%, 15%, 10%, 5%, 1% or less over a period of time. In some embodiments, the API release rate may be substantially constant for a period of time and vary over another consecutive or nonconsecutive period of time and vice versa.

In some embodiments, the composition may provide an API release pattern having a rapid release portion and a substantially constant release portion. The rapid release portion may comprise the amount of API released from administration (i.e., t=0) to 2 hours after administration or any range therein, such as, but not limited to, about 0 to about 1 hour or about 0 to about 30 minutes after administration. The substantially constant release portion may comprise the amount of API released from immediately after the rapid release portion to the final amount of API is released. An API may be released from a composition of the present invention for any period of time. In some embodiments, an API may be released from the composition for at least about 4 hours, 6 hours, 12 hours, 24 hours. 2 days, 3, days, 4 days, 5, days, 6 days, 7 days, or more, or any range and/or individual value therein. The API released from the composition may be released in an amount that overall provides a beneficial effect on the subject and/or provides a therapeutically effective amount of the API over a given period of time.

In some embodiments, a greater amount or concentration of the API may be released during the rapid release portion compared to the substantially constant release portion or vice versa. In some embodiments, the amount of API released from the composition during the rapid release portion may be about 10%, 20%, 30%, 40%, 50%, 60%, 70%, 80%, 90%, 100%, 150%, 200%, 300%, 400%, 500%, or more, or any range and/or individual value therein, of the amount of API released during the substantially constant release portion. In other embodiments, the amount of API released from the composition during the substantially constant release portion may be about 10%, 20%, 30%, 40%, 50%, 60%, 70%, 80%, 90%, 100%, 150%, 200%, 300%, 400%, 500%, or more, or any range and/or individual value therein, of the amount of API released during the rapid release portion.

In some embodiments, at least 50% or more (e.g., 60%, 70%, 80%, 90%, 95%, or more) of an API may be released from a composition of the present invention in less than about 2 hours, 1.75 hours, 1.5 hours, 1.25 hours, 1 hour, 45 minutes, or 30 minutes or any range and/or individual value therein. In some embodiments, the Cmax of an API released from a composition of the present invention may be achieved in less than about 2 hours, 1.75 hours, 1.5 hours, 1.25 hours, 1 hour, 45 minutes, 30 minutes, 25 minutes, 20 minutes, 15 minutes, 10 minutes, 5 minutes, or 2 minutes or any range and/or individual value therein. In some embodiments, a composition of the present invention may administer and/or deliver the API in a concentration or amount sufficient to penetrate a given skin and/or nail thickness, (e.g., a thickness of about 4 mm or less) to which the composition is applied. In some embodiments, a composition of the present invention may administer and/or deliver an API through a nail of a subject to the respective nail bed. In some embodiments, a composition of the present invention may release and/or deliver an API in an amount that achieves a minimum inhibitory concentration for a respective fungus to treat and/or prevent a fungal infection. In some embodiments, a composition of the present invention may release and/or deliver an API at concentration that provides a 3 log microbial kill in a given period of time for a respective fungus, such as, for example, *T. rubrum*. In some embodiments, the 3 log microbial kill may be in 120 minutes (i.e., MBC120), 3 hours or more, such as, for example, 4, 5, 6, 7, 8, 9, 10, 11, 12, 13, 14, 15, 16, 17, 18, 19, 20, 21, 22, 23, 24 hours or more.

In some embodiments, a first composition in an admixture may modulate the pH of a second composition in the admixture such that when the admixture is formed and/or applied to the skin of a subject, the pH of the admixture is less than about 11, in further embodiments, less than about 10, in still further embodiments, less than about 9, and in yet further embodiments, between about 5 and about 8. In some embodiments, a first composition in an admixture may be configured to maintain and/or stabilize the pH of the admixture in a desired pH range, such as, but not limited to, a pH range of about 3 to about 11, about 3 to about 9, about 4 to about 7, or about 5 to about 8.

An admixture of the present invention may be suitable for topical administration. The admixture may comprise a single phase even though it may be prepared or formed from two or more different compositions. The admixture may be buffered. In some embodiments, the admixture may comprise a first composition and a second composition. In some embodiments, the first composition may be a hydrogel. "Hydrogel," as used herein, refers to a hydrophilic gel comprising a gel matrix and water. In some embodiments, the second composition may be an anhydrous gel. The hydrogel and anhydrous gel when combined may form an admixture having a single phase that is optionally buffered. The second composition may comprise a nitric oxide-releasing active pharmaceutical ingredient (NO-releasing API). In some embodiments, the hydrogel and anhydrous gel when combined may be a film-forming composition (e.g., a film-forming gel).

In some embodiments, a composition, system, kit, and/or admixture of the present invention comprises, consists essentially of, or consists of a first composition of the present invention and a second composition of the present invention. The first composition and the second composition may be compatible with each other such that they may be mixed and/or combined together to provide an admixture of the present invention.

In some embodiments, a hydrogel and/or admixture of the present invention may comprise a thickening agent, water, a co-solvent, and/or buffering agent. The hydrogel and/or admixture may further comprise a preservative. In some embodiments, the hydrogel and/or admixture may further comprise other excipients, such as, e.g., humectants, anti-tacking agents, opacifiers, and/or acidifying agents. In some embodiments, a composition of the present invention (e.g., a hydrogel and/or admixture) does not include a chelating agent.

One or more (e.g., 1, 2, 3, 4, or more) thickening agent(s) may be present in a hydrogel and/or admixture of the present invention. In some embodiments, a hydrogel and/or admixture may comprise at least two different thickening agents. Example thickening agents include, but are not limited to, a carboxypolymethylene; a polyacrylic polymer and/or copolymer such as polyacrylic acid, a polyacrylate polymer, a cross-linked polyacrylate polymer, a cross-linked polyacrylic acid polymer and/or copolymer, and mixtures thereof; a cellulose ether such as hydroxyalkyl cellulose polymers such as hydroxypropyl methyl cellulose (HPMC), hydroxypropyl cellulose, hydroxyethyl cellulose, methyl cellulose, carboxymethyl cellulose and its salts (e.g., sodium carboxymethyl cellulose), and mixtures thereof; a methacrylate; a polyvinylpyrollidone; a cross-linked polyvinyl pyrrolidone; a copolymer of methyl vinyl ether and maleic anhydride; a polyvinylpyrrolidone-vinyl acetate copolymer; polyvinylalcohol; polyethylene oxide; polyethylene glycol; polyvinylalkyl ether-maleic acid copolymer; a carboxy vinyl polymer; a polysaccharide; a gum such as sodium alginate, carrageenan, xantham gum, gum acacia, arabic gun, guar gum, pullulan, agar, chitin, chitosan, pectin, karaya gum, zein, hordein, gliadin, locust bean gum, tragacantha, and mixtures thereof; a protein such as collagen, whey protein isolate, casein, milk protein, soy protein, gelatin, and mixtures thereof; a starch such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan, gluten, and mixtures thereof; bentonite; calcium stearate; ceratonia; colloidal silicon dioxide; dextrin; hypromellose; polycarbophil; kaolin; saponite; sorbitan esters; sucrose; sesame oil; tragacanth; potassium alginate; povidone; sodium starch glycolate; phospholipids; and any combination thereof. In some embodiments, the thickening agent may be a film forming agent (e.g., a film forming polymer), such as, but not limited to, ammonium alginate, chitosan, chlorpheniramine maleate, copovidone, dibutyl phthalate, dibutyl sebacate, diethyl phthalate, dimethyl phthalate, ethyl lactate, ethylcellulose, gelatin, hydroxyethyl cellulose, hydroxypropyl cellulose, hypromellose, hypromellose acetate succinate, maleic acid, maltodextrin, polyethylene glycol, polyethylene oxide, polymethacrylates, poly(methylvinyl ether/maleic anhydride), copolymers of methyl vinyl ether and maleic acid, and/or polyvinyl acetate phthalate.

In some embodiments, a hydrogel and/or admixture of the present invention may comprise a copolymer of methyl vinyl ether and maleic acid, such as, but not limited to, those commercially available from Ashland, Inc. of Covington, Ky. under the trade name Gantrez™. Example Gantrez™ polymers that may be present in a hydrogel and/or admixture of the present invention include, but are not limited to, Gantrez™ S polymers such as, for example, Gantrez™ S-97, Gantrez™ S-95, and/or Gantrez™ S-97 BF.

In some embodiments, a hydrogel and/or admixture of the present invention may comprise a carboxypolymethylene, a crosslinked polyacrylate polymer, and/or a cross-linked polyacrylic acid copolymer, such as, but not limited to, those commercially available from Lubrizol Corporation of Wickliffe, Ohio under the trade name Carbopol®. Example Carbopol® polymers that may be present in a hydrogel and/or admixture of the present invention include, but are not limited to, Carbopol® 974P NF polymer, such as Type A, Type B and/or Type C Homopolymers; Carbopol® 2020 ETD, Carbopol® Ultrez 10, 20, 21 NF polymer; Carbopol® 971P NF polymer; Carbopol® 980 Homopolymer Type C polymer, Carhop® 980 NF polymer, Carbopol® 980P polymer, Carbopol® ETD 2020 NF polymer, Carbopol® 71 G NF polymer, Carbopol® 981P NF polymer, Carbopol® 970P NF polymer, Carbopol® 981P NF polymer, Carbopol® 5984P NF polymer, Carbopol® 934P NF polymer, Carbopol® 940P NF polymer, Carbopol® 941P NF polymer, Carbopol® 13242 NF polymer, Carbopol® AA-1 USP NT polymer, Carbopol® TR1 NF polymer, Carbopol® TR2 NF polymer, Lubrizol Aqua CC polymer and SF-2 polymer, and any combination thereof.

In some embodiments, a thickening agent present in a hydrogel and/or admixture of the present invention may be a polymer comprising acidic groups, such as, but not limited to, carboxylic acid groups. The acidic groups of the polymer may be partially neutralized in a hydrogel and/or admixture of the present invention. In some embodiments, a thickening agent present in a hydrogel and/or admixture of the present invention may be a carboxypolymethylene, a crosslinked polyacrylate polymer, and/or a cross-linked polyacrylic acid copolymer. In some embodiments, a carboxypolymethylene, a crosslinked polyacrylate polymer, and/or a cross-linked polyacrylic acid copolymer present in a hydrogel and/or admixture of the present invention may be partially neutralized. A hydrogel of the present invention may comprise a carboxypolymethylene, a crosslinked polyacrylate polymer, and/or a cross-linked polyacrylic acid copolymer and have a pH of about 3 to about 7, about 3.5 to about 6.5, about 3.5 to about 6, about 3 to about 4, or about 4 to about 6. In certain embodiments, a hydrogel of the present invention may comprise a carboxypolymethylene, a crosslinked polyacrylate polymer, and/or a cross-linked polyacrylic acid copolymer and have a pH of about 3, 3.5, 4, 4.5, 5, 5.5, 6, 6.5, or 7.

One or more thickening agent(s) (e.g., 1, 2, 3, 4, 5 or more), alone or together, may be present in a hydrogel of the present invention at a concentration from about 0.1% to about 30% by weight of the hydrogel or any range and/or individual value therein, such as, but not limited to, about 0.2% to about 20%, about 0.1% to about 25%, about 5% to about 20%, about 0.5% to about 2%, about 0.5% to about 5%, or about 10% to about 20% by weight of the hydrogel. In some embodiments, one or more thickening agent(s) may be present in the hydrogel in an amount of about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, or 25% by weight of the hydrogel or any range and/or individual value therein. In some embodiments, one or more thickening agent(s) may be present in a hydrogel in an amount greater than 5% by weight of the hydrogel. In some embodiments, the total amount of thickening agent(s) present in a hydrogel of the present invention (i.e., the sum of the amount of all thickening agents present in the hydrogel) may be greater than 5% and up to 30% by weight of the hydrogel. In some embodiments, a hydrogel and/or admixture of the present invention comprises a copolymer of methyl vinyl ether and maleic acid, carboxymethylcellulose or a salt thereof, and/or a crosslinked polyacrylic acid polymer.

Water may be present in a hydrogel and/or admixture of the present invention. Water may be a solvent in a hydrogel of the present invention. In some embodiments, water may be present in a hydrogel of the present invention in an amount of about 50% or more by weight of the hydrogel, such as, for example, about 50% to about 75%, about 50% to about 70%, about 50% to about 60%, or about 70% to about 80% by weight of the hydrogel. In some embodiments, water may be present in a hydrogel of the present invention in an amount of about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the hydrogel or any range and/or individual value therein. In some embodiments, water may be present in amount less than 70% by weight of the hydrogel.

One or more (e.g., 1, 2, 3, 4, or more) co-solvent(s) may be present in a hydrogel and/or admixture of the present invention. In some embodiments, a hydrogel and/or admixture may comprise at least two different co-solvents. Example co-solvents include, but are not limited to, acetone, an alcohol (e.g., methyl alcohol, benzyl alcohol, ethanol, isopropyl alcohol, butyl alcohol, and/or phenoxyethanol), dimethyl isosorbide, cyclomethicone, propylene glycol, hexylene glycol, glycerol, isopropanol, ethylene glycol, polyethylene glycol, ethoxydiglycol, isopropyl palmitate, butylene glycol, pyrrolidone, dimethyl sulfoxide (DMSO), ethyl acetate, an ether (e.g., diethylene glycol monoethyl ether), and any combination thereof. In some embodiments, the co-solvent may be an alcohol. As one of skill in the art will understand, the co-solvent(s) in the hydrogel and/or admixture may be miscible with the solvent(s) in the hydrogel and/or admixture.

One or more co-solvent(s) (e.g., 1, 2, 3, 4, 5 or more), alone or together, may be present in a hydrogel of the present invention at a concentration from about 0.1% to about 20% by weight of the hydrogel or any range and/or individual value therein, such as, but not limited to, about 0.1% to about 15%, about 0.1% to about 10%, about 1% to about 10%, about 5% to about 10%, about 0.5% to about 3.5%, or about 2.5% to about 10% by weight of the hydrogel. In some embodiments, one or more co-solvent(s) may be present in the hydrogel in an amount of about 0.10%, 0.2%, 0.3%, 0.4%, 0.5%, 0.6%, 0.7% 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, or 15% by weight of the hydrogel or any range and/or individual value therein. In some embodiments, the total amount of co-solvent(s) (e.g., alcohol(s)) present in a hydrogel of the present invention (i.e., the sum of the amount of all co-solvents present in the hydrogel) may be 20% or less by weight of the hydrogel, and in some embodiments, may be less than 15% or 10% by weight of the hydrogel. In some embodiments, the admixture and/or hydrogel comprises an alcohol.

A hydrogel of the present invention may be unbuffered or buffered. In some embodiments, a hydrogel of the present invention may be unbuffered. In other embodiments, a hydrogel of the present invention may be buffered. Example buffering agents that may be present in hydrogel and/or admixture of the present invention include, but are not limited to, acetic acid, an acetate (e.g., sodium acetate, etc.), hydrochloric acid, a citrate (e.g., sodium citrate, calcium citrate, etc.), a citro-phosphate, citric acid, lactic acid, tartaric acid, malic acid, glycine/HCl, saline (e.g., phosphate buffered saline (PBS), Tris-buffered saline (TBS), Tris-HCl, NaCl, Tweet buffered saline (TNT), Triton X-100 (PBT) and mixtures thereof), cacodylate, barbital, tris, boric acid, a borate (e.g, sodium boradate), succinic acid, a succinate (e.g., sodium succinate), a phosphate (e.g., potassium phosphate monobasic, monobasic sodium phosphate, etc.), a carbonate (e.g., calcium carbonate, etc.), a bicarbonate (e.g., sodium bicarbonate), and any combination thereof.

One or more buffering agent(s) (e.g., 1, 2, 3, 4, 5 or more), alone or together, may be present in a hydrogel of the present invention in an amount of about 0.01% to about 20% by weight of the hydrogel or any range and/or individual value therein, such as, but not limited to, about 0.1% to about 15%, about 10% to about 20%, about 5% to about 15%, or about 1% to about 15% by weight of the hydrogel. In some embodiments, a buffering agent is present in a hydrogel of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% by weight of the hydrogel or any range and/or individual value therein. In some embodiments, one or more buffering agent(s) may be present in a hydrogel in an amount greater than 2% by weight of the hydrogel. In some embodiments, the total amount of buffering agent(s) present in a hydrogel of the present invention (i.e., the sum of the amount of all buffering agents present in the hydrogel) may be greater than 2% and up to 20% by weight of the hydrogel.

In some embodiments, a buffering agent may present in a hydrogel of the present invention in an amount sufficient for the first composition to have a pH of about 3 to about 8 or any range and/or individual value therein, such as, but not limited to, about 3 to about 6, about 3 to about 5, about 3 to about 4, about 4 to about 7, about 5 to about 7, or about 6 to about 7. In some embodiments, a buffering agent may be present in a hydrogel of the present invention in an amount sufficient for the hydrogel to have a pH of about 3, 3.5, 4, 4.5, 5, 5.5, 6, 6.5, 7, 7.5, or 8, or any range and/or individual value therein. In some embodiments, the pH of the hydrogel is about 3.5 to about 4.5.

In some embodiments, a buffering agent may be present in a hydrogel and/or admixture of the present invention in an amount sufficient to provide a desired pH for the admixture comprising the hydrogel and a second composition of the present invention (e.g., an anhydrous gel). For example, an admixture of the present invention may comprise the second composition and a hydrogel comprising a buffering agent, wherein the buffering agent is present in an amount sufficient to provide the admixture with a pH of about 3 to about 11, such as, but not limited to, about 3 to about 8, about 7 to about 11, about 8 to about 10, about 3 to about 5, about 4 to about 7, about 5 to about 7, or about 6 to about 7. In some embodiments, a buffering agent may be present in a hydrogel of the present invention in an amount sufficient for the admixture to have a pH of about 3, 3.5, 4, 4.5, 5, 5.5, 6, 6.5, 7, 7.5, 8, 8.5, 9, 9.5, 10, 10.5, or 11, or any range and/or individual value therein. In some embodiments, the buffering agent may be present in a hydrogel of the present invention in an amount sufficient to provide a desired pH upon administration of an admixture of the present invention comprising the hydrogel and a second composition of the present invention to the skin of a subject.

A hydrogel and/or admixture of the present invention may comprise one or more (e.g., 2, 3, 4, or more) preservative(s). Example preservatives that may be present in a hydrogel and/or admixture of the present invention include, but are not limited to, sorbic acid, benzoic acid, methyl-paraben, propyl-paraben, methylchloroisothiazolinone, metholisothiazolinone, diazolidinyl urea, chlorobutanol, triclosan, benzethonium chloride, p-hydroxybenzoate, chlorhexidine, digluconate, hexadecyltrimethyl ammonium bromide, alcohols, benzalkonium chloride, boric acid, bronopol, butylparaben, butylene calcium acetate, calcium chloride, calcium lactate, carbon dioxide, cationic, and bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, isopropyl alcohol, lactic acid, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, sodium acetate, sodium benzoate, sodium borate, sodium lactate, sodium sulfite, sodium propionate, sodium metabisulfite, xylitol, sulphur dioxide, carbon dioxide, and any combination thereof.

A preservative may be present in a hydrogel of the present invention in an amount of about 0.01% to about 1% by weight of the hydrogel or any range and/or individual value therein, such as, but not limited to, about 0.01% to about 0.1%, about 0.05% to about 1%, or about 0.1% to about 1% by weight of the hydrogel. In some embodiments, a preservative may be present in a hydrogel of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% by weight of the hydrogel or any range and/or individual value therein.

A hydrogel and/or admixture of the present invention may comprise one or more (e.g., 2, 3, 4, or more) moisturizer(s). Example moisturizers that may be present in a hydrogel and/or admixture of the present invention include, but are not limited to, almond oil, aluminum stearate, canola oil, castor oil, ceratonia extract, cetostearyl alcohol, cetyl alcohol, cetyl esters wax, cholesterol, coconut oil, cottonseed oil, cyclomethicone, dibutyl sebacate, dimethicone, ethylene glycol palmitostearate, glycerin, glycerin monostearate, glyceryl monooleate, glyceryl monostearate, isopropyl myristate, isopropyl palmitate, lanolin, lecithin, light mineral oil, medium-chain triglycerides, mineral oil, mineral oil and lanolin alcohols, myristyl alcohol, octyldodecanol, oleyl alcohol, petrolatum, petrolatum and lanolin alcohols, safflower glycerides, safflower oil, soybean oil, stearyl alcohol, sunflower oil, tricaprylin, triolein, xylitol, zinc acetate, cyclomethicone, and any combination thereof.

A moisturizer may be present in a hydrogel of the present invention in an amount of about 0.01% to about 10% by weight of the hydrogel or any range and/or individual value therein, such as, but not limited to, about 0.01% to about 0.1%, about 0.05% to about 1%, about 1% to about 10%, about 2% to about 8%, about 5% to about 8%, or about 0.1% to about 1% by weight of the hydrogel. In some embodiments, a moisturizer may be present in a hydrogel of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% by weight of the hydrogel or any range and/or individual value therein.

A composition (e.g., hydrogel, second composition, and/or admixture) of the present invention may further comprise one or more excipients. Excipients for use in pharmaceutical compositions are well-known in the art and examples may be found in the Handbook of Pharmaceutical Excipients (Rowe, R. C. et al., APhA Publications; 5th ed., 2005). Classes of excipients may include, but are not limited to, a humectant, a pH modifier, a water repelling agent, an anti-foaming agent, a surfactant, a solubilizer, an emulsifying agent, a wetting agent, a penetration enhancer, opacifier (e.g., titanium dioxide) and/or an antioxidant.

An excipient may be present in a composition of the present invention at any suitable concentration. In some embodiments, an excipient may be present in a composition of the present invention at a concentration from about 0.1% to about 20% by weight of the composition or any range and/or individual value therein, such as, but not limited to, from about 1% to about 15%, about 0.1% to about 10%, or about 5% to about 10% by weight of the composition. In some embodiments, a excipient may be present in a composition of the present invention in an amount of about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% by weight of the composition or any range and/or individual value therein.

In some embodiments, a hydrogel of the present invention comprises, consists essentially of, or consists of a thickening agent present in an amount of about 0.1% to about 25% or 30% by weight of the hydrogel, water present in an amount of about 50% to about 99% by weight of the hydrogel, and a co-solvent present in an amount of about 0.1% to about 15% by weight of the hydrogel. The hydrogel may be buffered to have a pH in a range of about 3 to about 8, about 3 to about 6, or about 3 to about 5. In some embodiments, a hydrogel of the present invention comprises, consists essentially of, or consists of a thickening agent present in an amount of greater than 5% and up to about 25% or 30% by weight of the hydrogel, a co-solvent present in an amount of about 0.1% to about 5% or 10% by weight of the hydrogel, and water present in an amount of about 50% to less than 70% by weight of the hydrogel. The hydrogel may comprise at least two different thickening agents and/or at least two different co-solvents. In some embodiments, the hydrogel may comprise a buffering agent present in an amount of about 0.01% to about 20% by weight of the hydrogel. The hydrogel may further comprise a buffering agent present in an amount of about 0.1% to about 20% by weight of the hydrogel, and, in some embodiments, in an amount of greater than 2% and up to about 20% by weight of the hydrogel. The hydrogel may further comprise a preservative in an amount of about 0.1% to about 1% by weight of the hydrogel and/or a moisturizer present in an amount of about 0.1% to about 10% by weight of the hydrogel.

In some embodiments, a hydrogel of the present invention comprises, consists essentially of, or consists of a thickening agent present in an amount of about 0.1% to about 25% or 30% by weight of the hydrogel, water present in an amount of about 50% to about 70% by weight of the hydrogel, a buffering agent present in an amount of about 1% to about 20% by weight of the hydrogel, and a co-solvent present in an amount of about 1% to about 15% by weight of the hydrogel. The hydrogel may be buffered to have a pH in a range of, or about 3 to about 5 or may have a pH of about 4. The hydrogel may comprise at least two different thickening agents and the total amount of the thickening agent agents present in the hydrogel may be less than 25% or 30% by weight of the hydrogel.

As those skilled in the art will recognize in light of the present disclosure, the properties of a hydrogel of the present invention may confer and/or provide the same and/or similar properties to a composition of the present invention. For example, in some embodiments, a hydrogel of the present invention may comprise a preservative that is present in an amount sufficient to provide antimicrobial activity to an admixture in which the hydrogel is present. Thus, in some embodiments, a hydrogel, composition, and/or admixture of the present invention may be antimicrobial.

A composition and/or hydrogel of the present invention may have a viscosity in a range of about 5,000 cP to about 25,000 cP or any range and/or individual value therein, such as, but not limited to, about 5,000 cP to about 20,000 cP or about 7,000 cP to about 15,000 cP. In certain embodiments, a composition and/or hydrogel of the present invention may have a viscosity of about 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, or 25,000 cP or any range and/or individual value therein.

In some embodiments, a composition of the present invention may comprise a hydrogel of the present invention that has a viscosity that allows for mixing and/or combination with a second composition. For example, a hydrogel of the present invention may have a viscosity suitable and/or sufficient for mixing and/or combination with a second composition of the present invention in a person's hand and/or on a subject's skin. A hydrogel with too low of a viscosity may run off the skin of a subject prior to mixing and/or combination. A hydrogel with too high a viscosity may be difficult to mix with a second composition of the present invention and/or difficult to spread and/or apply the admixture on the skin of a subject. In some embodiments, a second composition of the present invention may have a viscosity in a range of about 30,000 cP to about 100,000 cP or any range and/or individual value therein, such as, but not limited to, about 30,000 cP to about 75,000 cP or about 75,000 cP to about 100,000 cP. In some embodiments, a second composition of the present invention may have a viscosity of about 50,000, 55,000, 60,000, 65,000, 70,000, 75,000, 80,000, 85,000, 90,000, 95,000, or 100,000 cP or any range and/or individual value therein.

A composition of the present invention may comprise an active pharmaceutical ingredient (API). Any suitable API or combinations of APIs may be included in a composition of the present invention. Examples of APIs include, but are not limited to, antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofilm agents, and any combination thereof. Example APIs include, but are not limited to, those described in International Application Publication No. WO 2013/006608, which is incorporated herein by reference in its entirety.

In some embodiments, a hydrogel of the present invention may not comprise an API. In certain embodiments, a hydrogel of the present invention does not contain a nitric oxide (NO) releasing API. In some embodiments, a hydrogel of the present invention may comprise at least one API, but the hydrogel may not comprise an NO-releasing API.

In some embodiments, a hydrogel of the present invention may comprise an API. In some embodiments, a hydrogel of the present invention comprises an API and a second composition of the present invention comprises a second API (e.g., a moisture sensitive API). In some embodiments, the API in the hydrogel and the second API in the second composition may not be chemically compatible and/or stable in the composition of the present invention. For example, the API in the hydrogel and the second API in the second composition may not be chemically compatible and/or stable when stored together in a composition of the present invention.

A hydrogel of the present invention may be suitable for use and/or combination with one or more, such as, but not limited to, 2, 3, 4, or more, compositions that may be the same and/or different. In some embodiments, a hydrogel of the present invention may be suitable for use and/or combination with one or more pharmaceutical compositions. A hydrogel of the present invention may be used as a drug delivery system and/or a drug release system. For example, a hydrogel of the present invention may be configured to modulate the release of an API in a second composition upon contact of the hydrogel and the second composition. Alternatively or in addition, a hydrogel of the present invention may be configured to modulate the pH of a second composition upon contact of the hydrogel of the present invention and the second composition. In some embodiments, a hydrogel of the present invention may be configured to modulate the pH of a second composition comprising a nitric oxide (NO) releasing API and/or the release of nitric oxide from an NO releasing API in a second composition.

"Contact," as used herein in reference to a first composition of the present invention (e.g, a hydrogel of the present invention) and a second composition of the present invention (e.g., an anhydrous composition of the present invention), refers to direct and/or indirect exposure of at least one component in the first composition to the second composition. Contact of the first composition and second composition may be accomplished by any means, such as, but not limited to, by mixing, stirring, blending, dispersing, milling, homogenizing, combining, applying to same area or region, and the like, and in some embodiments may optionally form an admixture of the present invention. For example, a hydrogel may come into direct contact with a second composition, such as, but not limited to, by mixing and/or combining the hydrogel and second composition to form an admixture of the present invention prior to, during, and/or after topical application to a subject. Direct contact of a hydrogel and second composition may occur by applying one or more layers of the second composition onto a subject and then applying one or more layers of the hydrogel onto a subject or vice versa to form an admixture of the present invention. Indirect contact may occur by applying a second composition onto a subject and then applying a hydrogel onto a subject through a substrate, such as, but not limited to, a cloth, bandage, gauze, and the like, or vice versa to optionally form an admixture of the present invention.

According to some embodiments of the present invention, upon contact of a hydrogel of the present invention and a second composition of the present invention, the hydrogel may be configured to modulate the release of an API present in the second composition, such as, but not limited to, an NO releasing API. In some embodiments, water and/or proton(s) present in a hydrogel of the present invention may contact a second composition to modulate the release of an API present in the second composition, such as, but not limited to, an NO releasing API. Alternatively or in addition, in some embodiments, contact of a hydrogel of the present invention with a second composition may modulate the pH of the second composition, thereby modulating the release of an API present in the second composition, such as, but not limited to, an NO releasing API. In some embodiments, a hydrogel of the present invention is configured to supply water and/or a proton(s) to a second composition of the present invention and/or configured to modulate the pH of a second composition of the present invention.

While not wishing to be bound to any particular theory, it is believed that a composition of the present invention comprising a hydrogel of the present invention and a NO-releasing API may provide a proton donating system that may provide for a high release of nitric oxide from the composition and/or a continuous release of nitric oxide from the composition. The proton donating system, while not wishing to be bound to any particular theory, may be an acid that may be formed by an admixture of the present invention (e.g., a composition comprising a hydrogel of the present invention and a second composition of the present invention) and/or a hydrogel of the present invention. A composition of the present invention may provide and/or allow for a proton to be in close proximity to an NO-donor in an NO-releasing API to thereby allow for the release of nitric oxide. A composition of the present invention may provide and/or allow for a proton to be in proximity of an NO-donor for an extended period of time to provide a continuous release of NO for about 1 or more hours, such as, but not limited to, 2, 3, 4, 5, 6, 7, 8, 9, 10, 11, 12, or more hours. In some embodiments, a composition of the present invention provides a release of NO of at least about 0.3, 0.5, or 1 μmol of NO per mg of the composition for at least about 4, 6, or 8 hours as measured in vitro.

The proton donating system may be provided by a hydrogel of the present invention. For example, a proton donating system may be provided by a hydrogel of the present invention comprising a thickening agent, water, a co-solvent, a buffering agent, a preservative, and/or a moisturizer.

In some embodiments, a hydrogel of the present invention modulates the pH of a second composition such that when the hydrogel and second composition are contacted and/or applied to the skin of a subject, the pH of the second composition and/or admixture may be less that about 11, in some embodiments, less than about 10, in certain embodiments, less than about 8.5, in further embodiments, less than about 7, and in still further embodiments, between about 6 and about 8.

In some embodiments, the pH of an admixture of the present invention changes upon application of the admixture to the skin of a subject. In some embodiments, the pH of an admixture of the present invention is decreased by the buffering capacity of the skin upon application of the admixture to the skin of a subject. In some embodiments, the pH of an admixture of the present invention after application of the admixture to the skin of a subject is less than the pH of the second composition applied to the skin without the hydrogel. In embodiments where the release kinetics of the API in a second composition varies with pH, the buffering capacity of the skin may be utilized to modulate release while improving stability of the admixture after combination and before application. Thus, for example, the pH of a second composition that includes a nitric oxide-releasing macromolecule may be greater than 10 before mixing, 9 after mixing and 8 after application to the skin. With each decrease in pH, the release of nitric oxide from the macromolecule may be increased. Accordingly, taking advantage of the changing pH and buffering capacity of the skin may allow for increased working time (e.g., mixing and application time) for a combined composition of the present invention.

In some embodiments, a composition of the present invention may comprise a second composition and the second composition may be an anhydrous composition. "Anhydrous," as used herein, means that there is no direct addition of water to the second composition when it is being prepared. However, those skilled in the art will recognize that water may be physically and/or chemically absorbed by the second composition and/or by one or more ingredients in the second composition at any time during the preparation, storage, and/or use of the second composition (i.e., indirect addition of water to the second composition). In some embodiments, the term "anhydrous" means that the second composition has a water content of less than 5% by weight of the second composition or any range and/or individual value therein. A second composition may have a water content of less than 5%, 4.5%, 4%, 3.5%, 3%, 2.5%, 2%, 1.5%, 1%, or 0.5%, or any range therein, by weight of the second composition. Water content may be measured by methods known to those of skill in the art, such as, but not limited to, Karl Fischer titration. In some embodiments, upon contact with a second composition of the present invention, a hydrogel of the present invention adds water to the second composition and/or the second composition absorbs water from the hydrogel of the present invention.

A second composition of the present invention may comprise, consist essentially of, or consist of a viscosity increasing agent, an emollient, a humectant, a solvent, a co-solvent, and/or an API. In some embodiments, the second composition is an anhydrous composition.

One or more viscosity agents (e.g., 1, 2, 3, 4, or more) may be present in a second composition and/or admixture of the present invention. In some embodiments, the second composition and/or admixture may comprise at least two different viscosity agents. Example viscosity increasing agents that may be present in a second composition and/or admixture of the present invention include, but are not limited to, co-polymers of carboxymethylcellulose and acrylic acid, N-vinylpyrrolidone, polyalkylene glycols (e.g., poly(ethylene glycol)), polyalkylene oxides (e.g., polyethylene oxide), polyvinyl alcohols, polyvinylpyrrolidone, polysiloxanes, poly(vinyl acetates), cellulose, derivatized celluloses, hydroxypropylcellulose, alginates, copolymers thereof, metallic stearates (e.g., aluminum stearate, magnesium stearate, zinc stearate, etc), hydrophobic and/or hydrophilic fumed silica, silicone elastomers, silicone elastomer blends, and/or synthetic, emulsifying waxes, and any combination thereof. In some embodiments, a second composition of the present invention may comprise a hydroxypropylcellulose, such as, but not limited to, hydroxypropylcellulose under the tradename Klucel® (e.g., Klucel® MF Pharm grade). In some embodiments, a second of the composition of the present invention may comprise a silicone elastomer blend, such as, for example, a silicone elastomer blend under the tradename Dow Corning® ST-Elastomer 10.

A viscosity increasing agent may be present in a second composition of the present invention in an amount of about 0.1% to about 10% by weight of the second composition or any range and/or individual value therein, such as, but not limited to, about 0.5% to about 10%, about 0.1% to about 2%, about 0.1% to about 5%, about 1% to about 10%, or about 1% to about 5% by weight of the second composition. In some embodiments, a viscosity increasing agent may be present in the second composition in an amount of about 0.1%, 0.25%, 0.5%, 0.75%, 1%, 2%, 3%, 4%, 5%, 6%, 7%, 8%, 9%, or 10% by weight of the second composition or any range and/or individual value therein. In some embodiments, one or more viscosity increasing agent(s) may be present in a second composition of the present invention in an amount of about 0.5% to about 5% by weight of the second composition. In some embodiments, the total amount of viscosity increasing agent(s) present in a second composition of the present invention (i.e., the sum of the amount of all viscosity increasing agents present in the second composition) may be less than 10% by weight of the second composition. In some embodiments, the second composition may comprise at least two different viscosity increasing agents.

One or more emollients (e.g., 1, 2, 3, 4, or more) may present in a second composition and/or admixture of the present invention. Example emollients that may be provided in a second composition and/or admixture, include, but not limited to, silicones, such as, for example, cyclomethicone, dimethicone, simethicone, C26-28 alkyl dimethicone, C26-28 alkyl methicone, polyphenylsisquioxane, trimethylsiloxysilicate and crosspolymers of cyclopentasiloxane and dimethicone/vinyltrimethylsiloxysilicate, almond oil, aluminum stearate, canola oil, castor oil, ceratonia extract, cetostearyl alcohol, cetyl alcohol, cetyl esters wax, cholesterol, coconut oil, cottonseed oil, cyclomethicone, dibutyl, sebacate, dimethicone, ethylene glycol palmitostearate, glycerin, glycerin monostearate, glyceryl monooleate, glyceryl monostearate, isopropyl myristate, isopropyl palmitate, lanolin, lecithin, light mineral oil, medium-chain triglycerides, mineral oil, mineral oil and lanolin alcohols, myristyl alcohol, octyldodecanol, oleyl alcohol, petrolatum, petrolatum and lanolin alcohols, safflower glycerides, safflower oil, soybean oil, stearyl alcohol, sunflower oil, tricaprylin, triolein, xylitol, zinc acetate, and any combination thereof. In some embodiments, an emollient present in a second composition and/or admixture of the present invention may be cyclomethicone.

An emollient may be present in a second composition of the present invention in an amount of about 1% to about 30% by weight of the second composition or any range and/or individual value therein, such as, but not limited to, about 1% to about 5%, about 5% to about 10%, about 16% to about 30%, or about 20% to about 30% by weight of the second composition. In some embodiments, an emollient may be present in the second composition in an amount of about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% by weight of the second composition or any range and/or individual value therein. In some embodiments, one or more emollient(s) may be present in a second composition of the present invention in an amount greater than 15% by weight of the second composition. In some embodiments, the total amount of emollient(s) present in a second composition of the present invention (i.e., the sum of the amount of all emollients present in the second composition) may be greater than 15% and up to 30% by weight of the second composition.

One or more humectants (e.g., 1, 2, 3, 4, or more) may be present in a second composition and/or admixture of the present invention. Example humectants that may be present in a second composition and/or admixture of the present invention include, but are not limited to, glycols, such as, e.g., diethylene glycol monoethyl ether; glycerols; sugar polyols, such as, e.g., sorbitol, xylitol and maltitol; polyols such as, e.g., polydextroses; quillaia, urea, and blends thereof. In some embodiments, a humectant in a second composition and/or admixture may comprise a C1-C10 monoalkylene glycol, such as, for example, hexylene glycol.

A humectant may be present in the second composition in an amount of about 1% to about 30% by weight of the second composition or any range and/or individual value therein, such as, but not limited to, about 2% to about 15%, about 5% to about 15%, about 10% to about 25%, or about 10% to about 30% by weight of the second composition. In some embodiments, a humectant may be present in the second composition in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight of the second composition or any range and/or individual value therein. In some embodiments, one or more humectant(s) may be present in a second composition of the present invention in an amount of about 5% to about 30% by weight of the second composition. In some embodiments, the total amount of humectant(s) present in a second composition of the present invention (i.e., the sum of the amount of all humectants present in the second composition) may be about 5% to about 30% by weight of the second composition.

A second composition and/or admixture of the present invention may comprise a solvent. Example solvents that may be present in a second composition and/or admixture of the present invention include, but are not limited to, acetone, an alcohol, such as, e.g., methyl alcohol, benzyl alcohol, ethanol, isopropyl alcohol, butyl alcohol, and/or phenoxyethanol; dimethyl isosorbide, propylene glycol, hexylene glycol, glycerol, isopropanol, ethylene glycol polyethylene glycol, ethoxydiglycol, isopropyl palmitate, butylene glycol, pyrrolidone, dimethyl sulfoxide (DMSO), ethyl acetate, an ether (e.g., diethylene glycol monoethyl ether), and any combination thereof. In some embodiments, the solvent in a second composition and/or admixture may be a C1-C4 alcohol, such as, for example, ethanol and/or isopropyl alcohol.

A solvent may be present in a second composition of the present invention in an amount of about 1% to about 20% by weight of the second composition or any range and/or individual value therein, such as, but not limited to, about 2% to about 15%, about 5% to about 20%, about 10% to about 15%, or about 10% to about 20% by weight of the second composition. In some embodiments, a solvent may be present in the second composition in an amount of about 1%, 2%, 3%, 4%, 5%, 6%, 7%, 8%, 9%, 10%, 11%, 12%, 13%, 14%, 15%, 16%, 17%, 18%, 19%, or 20% by weight of the second composition or any range and/or individual value therein. In some embodiments, a solvent (e.g., an alcohol) may be present in a second composition of the present invention in an amount of about 1% to about 20% by weight of the second composition. In some embodiments, the solvent (e.g., an alcohol) may be present in a second composition of the present invention in an amount less than 20% by weight of the second composition. In some embodiments, the solvent may be a C1-C4 alcohol (e.g., ethanol and/or isopropyl alcohol), and the total amount of the C1-C4 alcohol (e.g., ethanol and/or isopropyl alcohol) present in a second composition of the present invention (i.e., the sum of the amount of C1-C4 alcohols present in the second composition) may be less than 20% by weight of the second composition.

One or more co-solvents (e.g., 1, 2, 3, 4, or more) may be present in the second composition and/or admixture of the present invention. Example co-solvents that may be present in a second composition and/or admixture of the present invention include, but are not limited to, acetone, an alcohol, such as, e.g., methyl alcohol, benzyl alcohol, ethanol, isopropyl alcohol, butyl alcohol, and/or phenoxyethanol; dimethyl isosorbide, propylene glycol hexylene glycol, glycerol, isopropanol, ethylene glycol, polyethylene glycol, ethoxydiglycol, isopropyl palmitate, butylene glycol, pyrrolidone, dimethyl sulfoxide (DMSO), ethyl acetate, an ether (e.g., diethylene glycol monoethyl ether), and any combination thereof. In some embodiments, the co-solvent in a second composition may be an ether, such as, for example, diethylene glycol monoethyl ether. In some embodiments, the co-solvent present in the second composition and/or admixture may comprise diethylene glycol monoethyl ether, such as, e.g., those commercially available from Gattefossee of Saint-Priest (Lyon, France) under the trade name Transcutol®.

A co-solvent may be present in a second composition of the present invention in an amount of about 1% to about 50% by weight of the second composition or any range and/or individual value therein, such as, but not limited to, about 2% to about 15%, about 25% to about 35%, about 10% to about 40%, or about 20% to about 40% by weight of the second composition. In some embodiments, a co-solvent may be present in the second composition in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 41%, 42%, 43%, 44%, 45%, 46%, 47%, 48%, 49%, or 50% by weight of the second composition or any range and/or individual value therein. In some embodiments, a co-solvent (e.g., an ether) may be present in a second composition of the present invention in an amount of about 1% to about 50% by weight of the second composition. In some embodiments, a co-solvent (e.g., an ether) may be present in a second composition of the present invention in an amount of less than 50% by weight of the second composition. In some embodiments, the total amount of co-solvent(s) present in a second composition of the present invention (i.e., the sum of the amount of co-solvents present in the second composition) may be less than 50% by weight of the second composition.

In some embodiments, a second composition of the present invention may comprise a C1-C4 alcohol (e.g., methanol, ethanol, isopropyl alcohol, and/or butyl alcohol) as the solvent and an ether (e.g., diethylene glycol monoethyl ether) as the co-solvent, and the C1-C4 alcohol may be present in the second composition in an amount less than 20% by weight of the second composition and the ether may be present in the second composition in an amount less than 50% by weight of the second composition. In some embodiments, the solvent is ethanol and/or isopropyl alcohol, and the total amount of ethanol and/or isopropyl alcohol present in a second composition of the present invention (i.e., the sum of the amount of ethanol and/or isopropyl alcohol present in the second composition) may be less than 20% by weight of the second composition.

In some embodiments, the total amount of solvent(s) and co-solvent(s) present in a second composition of the present invention (i.e., the sum of the amount of solvents and co-solvents present in the second composition) may be less than 50% by weight of the second composition, such as, for example, less than about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, or 10% by weight of the second composition or any range and/or individual value therein. In some embodiments, the total amount of solvent(s) and co-solvent (s) present in a second composition of the present invention may be about 10% to about 50% by weight of the second composition or any range and/or individual value therein, such as, but not limited to, about 30% to about 49%, about 10% to about 20%, about 10% to about 30%, or about 30% to about 40% by weight of the second composition.

In some embodiments, a second composition of the present invention comprises an API, such as, e.g., a moisture sensitive API. The second composition may stably store a moisture sensitive API. In some embodiments, the moisture sensitive API may comprise an NO-releasing API, such as, but not limited to a diazeniumdiolate modified macromolecule. In some embodiments, the NO-releasing API may be Nitricil™ NVN1 and/or Nitricil™ NVN4, which are NO-releasing diazeniumdiolate-functionalized co-condensed silica from Novan, Inc. of Durham, N.C.

"Nitric oxide releasing active pharmaceutical ingredient" and "NO releasing API," as used herein, refer to a compound or other composition that provides nitric oxide to the skin of a subject, but is not gaseous nitric oxide. In some embodiments, the NO releasing API includes a nitric oxide-releasing compound, hereinafter referred to as a "NO-releasing compound." An NO-releasing compound includes at least one NO donor, which is a functional group that may release nitric oxide under certain conditions. In some embodiments, the at least one NO donor of an NO-releasing compound releases NO when in contact with a composition of the present invention. In certain embodiments, a composition of the present invention modulates the amount of NO released from an NO-releasing compound and/or the rate of NO released from an NO-releasing compound. In some embodiments, a composition of the present invention increases the amount of NO released from an NO-releasing compound and/or the rate of NO released from an NO-releasing compound.

Any suitable NO-releasing compound may be used. In some embodiments, the NO-releasing compound includes a small molecule compound that includes an NO donor group. "Small molecule compound" as used herein is defined as a compound having a molecular weight of less than 500 daltons, and includes organic and/or inorganic small molecule compounds. In some embodiments, the NO-releasing compound includes a macromolecule that includes an NO donor group. A "macromolecule" is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 µm and may comprise the aggregation of two or more macromolecules, whereby the macromolecular structure is further modified with an NO donor group.

In some embodiments, the NO-releasing compound includes a diazeniumdiolate functional group as an NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light Examples of other NO donor groups include nitrosamine, hydroxyl nitrosamine, hydroxyl amine and hydroxyurea. Any suitable combination of NO donors and/or NO-releasing compounds may also be used in a second composition as described herein. Additionally, the NO donor may be incorporated into or onto the small molecule or macromolecule through covalent and/or non-covalent interactions.

An NO-releasing macromolecule may be in the form of an NO-releasing particle, such as those described in U.S. Application Publication No. 2009/0214618, the disclosure of which is incorporated by reference herein in its entirety. Other non-limiting examples of NO-releasing compounds include NO-releasing zeolites as described in United States Patent Publication Nos. 2006/0269620 or 2010/0331968, NO-releasing metal organic frameworks (MOFs) as described in United States Patent Application Publication Nos. 2010/0239512 or 2011/0052650; NO-releasing multi-donor compounds as described in International Application No. PCT/US2012/052350 entitled "Tunable Nitric Oxide-Releasing Macromolecules Having Multiple Nitric Oxide Donor Structures"; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, the disclosure of which is incorporated herein by reference in its entirety.

As an example, in some embodiments of the present invention, a nitric oxide-releasing active pharmaceutical ingredient may include NO-loaded precipitated silica. The NO-loaded precipitated silica may be formed from nitric oxide donor modified silane monomers into a co-condensed siloxane network. In some embodiments, the nitric oxide donor may be an N-diazeniumdiolate. In some embodiments, the nitric oxide-releasing active pharmaceutical ingredient may comprise, consist essentially of, or consist of a co-condensed siloxane network comprising a diazeniumdiolate (e.g., a N-diazeniumdiolate).

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors. In some embodiments of the present invention, the nitric oxide-releasing active pharmaceutical ingredient may comprise, consist essentially of, or consist of a co-condensed silica network synthesized from the condensation of a silane mixture comprising an alkoxysilane and at least one aminoalkoxysilane having an amine substituted by a diazeniumdiolate (e.g., a N-diazeniumdiolate).

The co-condensed siloxane network may be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula $Si(OR)_4$, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: $R''-(NH-R')_n-Si(OR)_3$, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl)phenethyltrimethoxysilane (AEMP3); [3-(methylamino)propyl]trimethoxysilane (MAPS); N-butylaminopropyltrimethoxysilane(n-BAP3); t-butylaminopropyltrimethoxysilane(t-BAP3); N-ethylaminoisobutyltrimethoxysilane(EAiB3); N-phenylamino-propyltrimethoxysilane (PAP3); and N-cyclohexylaminopropyltrimethoxysilane (cHAP3).

In some embodiments, the aminoalkoxysilane has the formula: NH [R'—Si(OR)3]2, wherein R is alkyl and is alkylene. In some embodiments, the aminoalkoxysilane may be selected from bis(3-triethoxysilylpropyl)amine, bis-[3-(trimethoxysilyl)propyl]amine and bis-[(3-trimethoxysilyl)propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: R"—N(NONO—X+)—R'—Si(OR)3, wherein R is alkyl, R' is alkylene or aralkylene, R" is alkyl or alkylamine, and X+ is a cation selected from the group consisting of Na+, K+ and Li+.

The composition of the siloxane network, (e.g., amount or the chemical composition of the aminoalkoxysilane) and the nitric oxide charging conditions (e.g., the solvent and base) may be varied to optimize the amount and duration of nitric oxide release. Thus, in some embodiments, the composition of the silica particles may be modified to regulate the half-life of NO release from silica particles.

In another embodiment, the amino group of aminoalkoxysilane is substituted with a diazeniumdiolate, and the aminoalkoxysilane having a formula of R"—N(NONO—X+)—R'—Si(OR)3, wherein: R is alkyl, R' is alkylene or aralkylene, R" is alkyl or alkylamine, and X+ is a cation selected from the group consisting of Na+ and K+.

In certain embodiments, the NO-releasing API may comprise a co-condensed silica network comprising diazeniumdiolated aminoethylaminopropyl trimethoxy silane (AEAP3) and tetra methyl orthosilicate (TMOS) and/or a co-condensed silica network comprising diazeniumdiolated aminoethylaminopropyl trimethoxy silane (AEAP3) and tetraethyl orthosilicate (TEOS). In some embodiments, the NO-releasing API may comprise a co-condensed silica network comprising diazeniumdiolated methylaminopropyl trimethoxysilane (MAPS) and tetra methyl orthosilicate (TMOS) and/or a co-condensed silica network comprising diazeniumdiolated methylaminopropyl trimethoxysilane (MAPS) and tetraethyl orthosilicate (TEOS).

In some embodiments, the particle size of a NO-releasing API may be in a range of about 20 nm to about 20 µm or any range therein, such as, but not limited to, about 100 nm to about 20 µm or about 1 µm to about 20 µm. The particle size may be tailored to minimize or prevent toxicity and/or penetration through the epidermis (or compromised dermis) and into the blood vessels. In particular embodiments, the particle size is distributed around a mean particle size of less than 20 µm, or any range therein, and the size may allow the particle to enter a follicle. In some embodiments, a NO-releasing API may have a particle size that is distributed around a mean particle size of about 20, 19, 18, 17, 16, 15, 14, 13, 12, 11, 10, 9, 8, 7, 5, 4, 3, 2, or 1 µm. In further embodiments, a NO-releasing API may have a particle size that is distributed around a mean particle size of less than 10 µm, or any range therein, such as, but not limited to about 2 µm to about 10 µm or about 4 µm to about 8 µm. In other embodiments, the particle size may be distributed around a mean particle size of greater than 20 µm, or any range therein, and the size may prevent the particle from entering the follicle. In still further embodiments, a mixture of particles with mean particle sizes distributed around two or more mean particle sizes may be provided. A NO-releasing API may be micronized (e.g., ball and/or jet milled). Methods for providing a desired particle size and/or micronization include, but are not limited to, those described in U.S. Patent Application Publication No. 2013/0310533, which is incorporated herein by reference in its entirety.

A nitric oxide-releasing active pharmaceutical ingredient diazeniumdiolate-functionalized co-condensed silica) may be present in a composition of the present invention in an amount of about 0.1% to about 50% by weight of the composition, and/or any range and/or individual value therein, such as, for example, about 0.1% to about 35%, about 20% to about 30%, about 2% to about 15%, about 10% to about 40%, about 5% to about 35%, or about 1% to about 10% by weight of the composition. In some embodiments, a nitric oxide-releasing active pharmaceutical ingredient may be present in a composition of the present invention in an amount of about 0.1%, 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% by weight of the composition. In some embodiments, a nitric oxide-releasing active pharmaceutical ingredient (e.g., diazeniumdiolate-functionalized co-condensed silica) may be present in a second composition of the present invention in an amount of about 0.1% to about 50% by weight of the second composition and/or any range and/or individual value therein.

A composition of the present invention (e.g., a second composition of the present invention) may comprise a nitric oxide-releasing active pharmaceutical ingredient and may store and/or release nitric oxide in an amount of about 0.05% to about 20% by weight of the composition, such as, but not limited to, about 0.15% to about 2%, about 0.15% to about 1%, about 0.3% to about 1.2%, about 0.15% to about 6%, about 1% to about 10%, about 3% to about 6%, about 2% to about 20%, about 5% to about 15%, about 10% to about 20%, or about 1% to about 5% by weight of the composition. In some embodiments, a composition of the present invention may comprise a NO-releasing compound and may store and/or release NO in an amount of about 0.15%, 0.3%, 0.6%, 0.9%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, or 20% by weight of the composition. The amount of nitric oxide released may be determined using real time in vitro release testing. In some embodiments, nitric oxide release may be determined using a chemiluminescent nitric oxide analyzer.

In some embodiments, a composition of the present invention may comprise a NO-releasing compound that may store and/or release about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, or 7 µmol of NO per mg of the NO-releasing compound. The amount of nitric oxide released may be determined using real time in vitro release testing.

In some embodiments, a hydrogel of the present invention may increase the amount of NC) released from a composition (e.g., a second composition comprising a NO-releasing API) compared to the amount of NO released from the composition in the absence of the hydrogel over the same period of time. In certain embodiments, a hydrogel of the present invention may increase the amount of NO released from a composition of the present invention comprising the hydrogel and a NO-releasing API by at least about 10%, 20%, 30%, 40%, 50%, 60%, 70%, 80%, 90, 100%, 150%, 200%, or more, or any range and/or individual value therein compared to the amount of NO released in the absence of a hydrogel of the present invention over the same period of time. Therefore, a composition of the present invention (e.g., a composition comprising a hydrogel of the present invention and a second composition comprising a NO-releasing API) may release about 1.5 to about 100 times more NO than the amount of NO released in the absence of a hydrogel of the present invention (e.g., the second composition alone) over the same period of time or any range and/or individual value therein, such as, but not limited to between about 2 and 10 times more NO or between about 5 and about 50 times more NO.

A second composition of the present invention may comprise, consist essentially of, or consist of a viscosity increasing agent present in an amount of about 0.1% to about 10% by weight of the second composition, an emollient present in an amount of about 1% to about 30% by weight of the second composition, a humectant present in an amount of about 1% to about 30% by weight of the second composition, a solvent present in an amount of about 1% to about 20% by weight of the second composition, a co-solvent present in an amount of about 1% to about 50% by weight of the second composition, and/or a moisture sensitive API (e.g., a NO-releasing API) in an amount of about 0.1% to about 50% by weight of the second composition. In some embodiments, the second composition may comprise at least two different viscosity increasing agents and the total amount of the viscosity increasing agents present in the second composition may be less than 10% by weight of the second composition. In some embodiments, the second composition may comprise, consist essentially of, or consist of a viscosity increasing agent present in an amount of less than about 10% by weight of the second composition, the emollient present in an amount of greater than 15% and up to about 30% by weight of the second composition, the humectant present in an amount of about 1% to about 30% by weight of the second composition, the solvent (e.g., a C1-C4 alcohol) present in an amount of less than 20% by weight of the second composition, the co-solvent present in an amount of less than 50% by weight of the second composition, and/or a moisture sensitive API (e.g., a NO-releasing API) in an amount of about 0.1% to about 50% by weight of the second composition. In some embodiments, the total amount of the solvent(s) and co-solvent(s) present in the second composition is less than 50% by weight of the second composition.

A second composition of the present invention may comprise, consist essentially of, or consist of a viscosity increasing agent present in an amount of about 0.1% to about 5% by weight of the second composition, an emollient present in an amount of about 5% to about 30% by weight of the second composition, a humectant present in an amount of about 5% to about 30% by weight of the second composition, a solvent (e.g., an alcohol) present in an amount of about 1% to about 20% by weight of the second composition, a co-solvent present in an amount of about 15% to about 50% by weight of the second composition, and/or a moisture sensitive API (e.g., a NO-releasing API) in an amount of about 0.1% to about 40% by weight of the second composition. In some embodiments, the second composition may comprise at least two different viscosity increasing agents and the total amount of the viscosity increasing agents present in the second composition may be less than 5% by weight of the second composition.

A composition of the present invention may comprise a first composition (e.g., a hydrogel) of the present invention and a second composition of the present invention. As those of skill in the art will recognize, the amount or concentration of individual components in a composition of the present invention may vary depending on the amount of the first composition and second composition present in the composition (e.g., the ratio of the first composition and second composition present in the composition). In some embodiments, the ratio of a first composition of the present invention to a second composition of the present invention in a composition of the present invention may be about 10:1 or less, such as, e.g., about 9:1 or less, about 8:1 or less, about 7:1 or less, about 6:1 or less, about 5:1 or less, about 4:1 or less, about 3:1 or less, about 2:1 or less, about 1:1 or less, about 0.5:1 or less, or about 0.2:1 or less. In some embodiments, the ratio may be about 3:1. In further embodiments, the ratio may be about 1:1.

A composition of the present invention e.g., a first composition of the present invention and a second composition of the present invention) may be buffered to a pH of about 3 to about 11, such as, but not limited to, about 3 to about 9.5 or about 3 to about 8. In some embodiments, an admixture of the present invention may have a pH of 9.5 or greater. In some embodiments, the composition may comprise at least one API, such as, but not limited to, a nitric oxide-releasing active pharmaceutical ingredient. In some embodiments, a composition of the present invention may comprise a second composition comprising a nitric oxide-releasing active pharmaceutical ingredient. In some embodiments, the second composition may be anhydrous.

In some embodiments, an admixture of the present invention may comprise, consist essentially of, or consist of a first composition and a second composition, the first composition comprising a thickening agent present in an amount of about 0.1% to about 25% by weight of the first composition, water present in an amount of about 50% to about 99% by weight of the first composition, a cosolvent present in an amount of about 0.1% to about 15% by weight of the first composition, a buffering agent present in an amount of about 0.01% to about 20% by weight of the first composition, a preservative in an amount of about 0.1% to about 1% by weight of the first composition, and/or a moisturizer present in an amount of about 0.1% to about 10% by weight of the first composition; and the second composition comprising a viscosity increasing agent present in an amount of about 0.1% to about 10% by weight of the second composition, an emollient present in an amount of about 1% to about 30% by weight of the second composition, a humectant present in an amount of about 1% to about 30% by weight of the second composition, a solvent present in an amount of about 1% to about 20% by weight of the second composition, a co-solvent present in an amount of about 1% to about 50% by weight of the second composition, and/or a moisture sensitive API (e.g., a NO-releasing API) in an amount of about 0.1% to about 50% by weight of the second composition. The first composition may be a hydrogel and/or the second composition may be an anhydrous composition. In some embodiments, the admixture may be a film-forming composition (e.g., a film-forming gel). In some embodiments, the total amount of the thickening agent present in the first composition may be greater than 5% and up to about 25% by weight of the first composition, the total amount of the co-solvent may be about 0.1% to about 5% by weight of the first composition, water may be present in an amount of about 50% to less than 70% by weight of the first composition, and/or the buffering agent may be present in an amount of greater than 2% and up to about 20% by weight of the hydrogel. In some embodiments, the total amount of the viscosity increasing agent present in the second composition may be less than about 10% by weight of the second composition, the emollient may be present in an amount of greater than 15% and up to about 30% by weight of the second composition, the solvent (e.g., a C1-C4 alcohol) may be present in an amount of less than 20% by weight of the second composition, and/or the co-solvent may be present in an amount of less than 50% by weight of the second composition, optionally with the total amount of the solvent(s) and co-solvent(s) present in the second composition is less than 50% by weight of the second composition. The admixture may have a pH of less than about 11, such as, but not limited to, less than about 9.5, less than about 7, or less than about 6. In some embodiments, the admixture may be cosmetically elegant.

An admixture of the present invention may provide a structure suitable for suspending an API, such as, but not limited to, a particulate API and/or an insoluble API. In some embodiments, an admixture of the present invention may encapsulate an API, such as, but not limited to, a particulate API and/or an insoluble API. For example, an admixture of the present invention may encapsulate an API in at least one viscosity increasing agent and/or thickening agent and/or may provide a structure suitable for encapsulating an API. An admixture of the present invention may prevent and/or reduce agglomeration of an API in the admixture. While not wishing to be bound to any particular theory, a hydrogel of the present invention may provide means for suspending and/or encapsulating an API and/or for preventing and/or reducing agglomeration of an API in the admixture. For example, a hydrogel of the present invention may provide a structure (e.g., a gel matrix) suitable for suspending and/or encapsulating an API in an admixture of the present invention and/or for preventing and/or reducing agglomeration of an API in an admixture of the present invention.

An admixture of the present invention may not be gritty and/or may have a reduced grittiness compared to the API in the absence of a composition of the present invention. The admixture may not be tacky (i.e., sticky) and/or may have a reduced tackiness (i.e., stickiness) compared to the API in the absence of a composition of the present invention. The admixture may have a reduced and/or increased stiffness (i.e., hardness) and/or may have an increased homogeneity compared to the API in the absence of a composition of the present invention. In some embodiments, an admixture of the present invention may comprise an API and may be a cosmetically elegant, homogeneous composition. While not wishing to be bound to any particular theory, a hydrogel of the present invention may provide means for providing a cosmetically elegant, homogeneous composition. For example, a hydrogel of the present invention may provide a structure (e.g., a gel matrix) suitable for providing a cosmetically elegant, homogeneous composition.

According to embodiments of the present invention, the preparation of two separate parts for a composition of the present invention may provide an improved composition. A composition of the present invention comprising at least two parts may allow for an API (e.g., an API that is difficult to formulate) to be prepared in one part and later combined with the second part to prepare a cosmetically elegant composition and/or a composition comprising a more stable API compared to the same API prepared in a composition formed with one part and/or in the absence of a composition of the present invention. The API may be more stable in that the API could have a greater activity compared to its activity in the absence of a composition of the present invention and/or the API may be stored for a longer period of time compared to its storage in the absence of a composition of the present invention. In some embodiments, a composition of the present invention comprising an API (e.g., an API that is difficult to formulate) may provide a more cosmetically elegant composition compared to the API in a composition in the absence of a composition of the present invention. For example, a composition of the present invention comprising a particulate API and/or an insoluble API may provide a less gritty composition and thereby a more cosmetically elegant composition.

In some embodiments, two or more different compositions of the present invention (e.g., first and second compositions of the present invention) may be separately stored. Any suitable packaging for a composition of the present the invention may be used. In some embodiments, each composition may be separately stored in a tube, jar, sachet, dual chamber container (e.g., a dual pump container, dual dispensing container, a dual pouch sachet, and/or a trilayer sachet). In some embodiments, a composition of the present invention may be refrigerated until use to reduce the likelihood of premature release of the nitric oxide.

In some embodiments, a composition of the present invention may be provided in sealed, single dose container (e.g., a vial, sachet, etc.) that may be oxygen and/or moisture impermeable to prevent moisture from reaching the composition and/or API. The single dose container may be opened at the time of application and the composition(s) may be applied to skin and/or a nail of a subject. In some embodiments, a hydrogel of the present invention and a second composition of the present invention may be separately stored in a container (e.g., a single dose container) and, upon opening the container (e.g., upon opening a sachet), both compartments storing the hydrogel and second composition are opened and can dispense and/or are configured for dispensing of each composition. The hydrogel and second composition may be dispensed from the single dose container concurrently and/or may be dispensed side by side. In some embodiments, a single action on the container (e.g., sachet) may dispense the compositions. In some embodiments, the hydrogel and second composition after dispensing may be mixed (e.g., manually by a subject) to form an admixture and/or some mixing may occur during dispensing (e.g., some contact and/or mixing may occur if the compositions are dispensed such that they contact each other). In some embodiments, a hydrogel of the present invention and a second composition of the present invention may be separately stored in two different compartments of a container (e.g., a sachet or tube) including a barrier between the compartments storing the hydrogel and second composition and the barrier is broken to combine the hydrogel and/or second composition prior to opening the container and/or dispensing the compositions.

According to some embodiments of the present invention, a kit may be provided. In some embodiments, a kit of the present invention may comprise a first composition of the present invention (e.g., a hydrogel) and a second composition of the present invention. The second composition may be an anhydrous composition. In some embodiments, a kit of the present invention may comprise means for forming an admixture with the first composition and second composition, such as, but not limited to, by mixing, combining, contacting, and the like the compositions prior to and/or during application to a subject. In some embodiments, the kit may be configured to admix the two compositions upon dispensing and/or application to a subject. In some embodiments, a kit may be configured to provide an admixture with increased performance and/or activity of the API compared to the performance and/or activity of the API in the absence of one or more of the compositions in the admixture.

A kit of the present invention may separately store a first composition of the present invention and a second composition of the present invention. In some embodiments, a kit of the present invention may contact and/or may allow for contact to occur between the first composition and second composition, such as, but not limited to, by mixing the compositions, prior to application to a subject.

A kit of the present invention may provide a ratio of the first composition to the second composition, which may be applied to a subject, of about 10:1 or less, such as, for example, about 9:1 or less, about 8:1 or less, about 7:1 or less, about 6:1 or less, about 5:1 or less, about 4:1 or less, about 3:1 or less, about 2:1 or less or about 1:1. In some embodiments, the ratio may be about 3:1. In some embodiments, the ratio may be about 1:1. In certain embodiments, a kit and/or system of the present invention comprises means for dispensing and/or delivering the first and second compositions in the appropriate amounts to achieve the desired ratio (e.g., dual dispensing pump, trilayer sachet, etc.). In some embodiments, the ratio of the first composition and second composition in the admixture may be adjusted and/or modified to achieve a desired API release pattern. In some embodiments, a kit and/or system of the present invention comprises a dual dispensing device, such as, for example, a dual dispensing pump, sachet, and/or the like, that separately stores a first composition of the present invention and second composition of the present invention and that in use (e.g., dispensing and/or administration) may provide a given ratio of the first composition to the second composition.

Providing a first composition and a second composition that are combined upon and/or during application to the skin of a subject may allow for a longer shelf life of a composition, kit, and/or system of the present invention than if the compositions were stored mixed together in the kit and/or system. For example, the formulation and loading of API in a second composition of the present invention may provide a stable product with a long shelf life. Thus, for example, pH and water content of the second composition may be adjusted to reduce or minimize release of a water-activated API so as to provide a composition that is stable at room temperature. A first composition of the present invention may then be combined with the second composition to adjust the combined pH and provide a proton and/or water to activate the API. The second composition may be combined with the first composition in differing ratios to provide a desired release, pH and/or dose in the combined composition. Such an approach may allow for a single manufacturing process to be utilized for production of a more complex and costly second composition and then particular products defined by the composition and/or quantity of the first composition with which the second composition is mixed.

As used herein, the term "shelf life" refers to the length of time a product (e.g., a composition and/or kit of the present invention) maintains the ability to release a therapeutically effective amount of a therapeutic agent, such as, but not limited to, nitric oxide, in an unopened package stored under recommended storage conditions. The shelf life may, for example, be evidenced by the "use by" or "best if used by" date for the product, the manufacturer's expiration date of the product and/or the actual product characteristics after the specified period of time. Accordingly, the term "shelf life" as used herein should be construed as including both an "actual" shelf life of the product and a "predicted" shelf life of the product unless stated otherwise. As one skilled in the art will recognize, the rate of release of nitric oxide in a composition under packaged and/or stored conditions may be different (i.e., faster or slower) than the rate of release of nitric oxide when the composition is in use (e.g., when the composition comprising the NO-releasing API is in admixture with another composition). In certain embodiments, the rate of release of nitric oxide from a composition of the present invention may be more rapid when the composition is in use compared to the rate of release of nitric oxide when a composition comprising the API was packaged and/or stored.

In some embodiments, shelf life may be determined by extrapolation of data at accelerated temperatures, such as, for example, by using the Arrhenius equation. In some embodiments, shelf life may be determined using linear regression analysis, such as, for example, when the kinetics of API degradation is not temperature dependent. In some embodiments, shelf life may be evaluated and/or determined by measuring the API (e.g., NO-releasing API), such as, for example, using high pressure liquid chromatography.

In some embodiments, the shelf life of the product is the time that the product maintains the ability to release at least 50% of the initial amount of nitric oxide that the product may release when packaged. In some embodiments, the shelf life of the product is the time that the product maintains the ability to release about 60%, at least 70%, at least 80%, at least 90%, at least 95%, or at least 98% of the initial amount of nitric oxide that the product may release when packaged. In some embodiments, the shelf life of the product is the time that the product maintains the ability to release a therapeutically effective amount of nitric oxide over a desired period of time. In some embodiments, the recommended storage conditions are room temperature. In some embodiments, the recommended storage conditions are refrigerated storage conditions. In particular embodiments, the refrigerated storage conditions are between 1° C.-12° C., or any range and/or individual value therein. In some embodiments, a packaged product may have a shelf life of at least about 1, 2, 3, 4, 5, 6, 7, 8, 9, 10, 11, 12, 13, 14, 15, 16, 17, 18, 19, 20, 21, 22, 23, or 24 months or more, or any range and/or individual value therein.

Some embodiments may provide packaged compositions of the present invention that have a useful life of at least about 7 days after opening the package. In some embodiments, the useful life is at least about 30 days, at least about 60 days or at least about 90 days. In still further embodiments, the packaged compositions have a useful life of from at least about 60 days to at least about 730 days. As used herein, the term "useful life" refers to the length of time that the product maintains the ability to release a therapeutically effective amount of nitric oxide from an opened packaged when applied as recommended and when stored under recommended storage conditions. The useful life may, for example, be evidenced by the manufacturer's recommended time to dispose of the product after opening or measurements of the products characteristics after opening.

Accordingly, the term "useful life" as used herein should be construed as including both an "actual" useful life of the product or a "predicted" useful life of the product unless stated otherwise. In some embodiments, the useful life of the product is the time that the product maintains the ability to release at least 50% of the initial amount nitric oxide that the product may release when the package is opened. In further embodiments, the useful life of the product is the time that the product maintains the ability to release at least 70%, at least 80%, at least 90%, at least 9.5%, or at least 98% of the initial amount nitric oxide that the product may release when the package is opened. In some embodiments, the recommended storage conditions after opening are room temperature. In particular embodiments, the recommended storage conditions after opening are refrigerated conditions.

As will be appreciated by those of skill in the art in light of the present disclosure, a hydrogel of the present invention may provide means for adjusting the pH of a pharmaceutical composition as well as means for activating an API of a pharmaceutical composition. In some embodiments, a hydrogel of the present invention may provide means for maintaining and/or stabilizing the pH of a second composition of the present invention when used to form an admixture with the hydrogel. Means for maintaining and/or stabilizing the pH of an admixture may be configured to activate and/or initiate release of an API. In some embodiments, a hydrogel of the present invention may provide means for maintaining and/or stabilizing the pH of an admixture comprising a diazeniumdiolate modified co-condensed polysiloxane macromolecule. In some embodiments, the pH may be maintained and/or stabilized within a pH range of about 5 to about 8. In further embodiments, a hydrogel of the present invention may provide means for releasing nitric oxide from a pharmaceutical composition comprising a diazeniumdiolate modified co-condensed polysiloxane macromolecule. In some embodiments, a hydrogel of the present invention may provide means for reducing the pH of a second composition of the present invention comprising a diazeniumdiolate modified co-condensed polysiloxane macromolecule. In some embodiments, a first composition of the present invention may provide means for releasing nitric oxide from a second composition of present invention comprising a diazeniumdiolate modified co-condensed polysiloxane macromolecule.

According to some embodiments, a method of the present invention may comprise administering a composition (e.g., hydrogel, second composition and/or admixture) of the present invention to the skin and/or nail of a subject. For example, the composition may be administered to a subject's hand, foot, toe, and/or nail. In some embodiments, the composition may be topically administered. A method of the present invention may comprise forming an admixture prior to and/or during the administering step. An admixture may be prepared by mixing, blending, contacting, applying to a same area or region, emulsifying, and the like a hydrogel of the present invention, and a second composition of the present invention, such as, but not limited to an anhydrous composition. In some embodiments, a method of the present invention may administer a composition of the present invention as a monotherapy to treat at least two different conditions, infections and/or diseases. In some embodiments, a method of the present invention may administer a composition of the present invention as a monotherapy to treat onychomycosis and *Tinea pedis*. In some embodiments, a method of the present invention may administer a composition of the present invention in combination with a different therapy (e.g., in combination with an oral therapy such as, e.g., orally administered terbinafine). In some embodiments, a method and/or step of the present invention includes, but is not limited to, a composition, method, and/or step described in International Application Nos. PCT/US2015/040319, PCT/US2016/013246, and/or PCT/US2016/043880, the contents of each of which are incorporated herein by reference in their entirety.

A method of the present invention may comprise topically applying a first composition of the present invention to the skin of a subject in combination and/or admixture with a second composition of the present invention. The second composition may comprise a nitric oxide-releasing active pharmaceutical ingredient (e.g., a NO-releasing macromolecule).

In some embodiments, a composition and/or method of the present invention provides and/or delivers nitric oxide to the skin and/or nail of a subject in a concentration effective to inhibit fungi growth and/or kill fungi, such as, for example, *Trichophyton rubrum*. In some embodiments, a composition and/or method of the present invention provides and/or delivers nitric oxide to a subject's nail bed. In some embodiments, the nitric oxide may diffuse and/or penetrate through the subject's nail to the respective nail bed. In some embodiments, a method of the present invention comprises delivering a therapeutically effective amount of a composition of the present invention to the skin and/or nail of a subject. A composition and/or method of the present invention may provide and/or deliver nitric oxide to a subject's skin and/or nail and may be delivered to the nail bed under the subject's nail.

As used herein, the term "therapeutically effective amount" refers to an amount of a compositional of the present invention that elicits a therapeutically useful response in a subject. Those skilled in the art will appreciate that the therapeutic effects need not be complete or curative, as long as some benefit is provided to the subject. In some embodiments, a therapeutically effective amount of a composition of the present invention may include delivering a therapeutically effective amount of a component of the composition, such as, but not limited to, an active pharmaceutical ingredient (e.g., a nitric oxide-releasing API). Therefore, a therapeutically effective amount of nitric oxide may be delivered and/or administered by a composition of the present invention.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom associated with a viral, bacterial, protozoan, and/or fungal (e.g., onychomycosis and/or *Tinea pedis*) infection is achieved and/or there is a delay in the progression of the infection and/or condition. In some embodiments, the severity of an infection (e.g., a fungal infection caused by *T. rubrum*) may be reduced in a subject compared to the severity of the infection in the absence of a method of the present invention. In certain embodiments, a method of the present invention treats a viral, bacterial, protozoan, and/or fungal (e.g., onychomycosis and/or *Tinea pedis*) infection in a subject, such as, e.g., a fungal infection that has affected the skin and/or nail of the subject. In some embodiments, a method of the present invention may treat a viral, bacterial, protozoan, and/or fungal onychomycosis and/or *Tinea pedis*) infection by eliminating and/or reducing the size and/or appearance of at least one clinical symptom associated with the infection (e.g., a disfiguration, discoloration, and/or benign lesion such as a scaly patch). In some embodiments, a method of the present invention may treat a viral, bacterial, protozoan, and/or fungal (e.g., onychomycosis and/or *Tinea pedis*) infection by eliminating at least one clinical symptom associated with the infection for a given period of time (e.g., 1, 2, 3, 4, 5, or 6 day(s), or 1, 3, 4, or more weeks, or 1, 2, 3, 4, 5, 6, or more months, etc.).

In some embodiments, a composition of the present invention (e.g., an admixture) may be administered in a treatment effective amount. A "treatment effective" amount as used herein is an amount that is sufficient to treat (as defined herein) a subject. Those skilled in the art will appreciate that the therapeutic effects need not be complete or curative, as long as some benefit is provided to the subject. In some embodiments, a treatment effective amount may be achieved by administering a composition of the present invention. In some embodiments, administration of a composition of the present invention does not produce systemic effects from the administration of nitric oxide, such as, for example, in a treatment effective amount.

The terms "prevent," "preventing" and "prevention" (and grammatical variations thereof) refer to avoidance, reduction and/or delay of the onset of a viral, bacterial, protozoan, and/or fungal (e.g., onychomycosis and/or *Tinea pedis*) infection and/or a clinical symptom associated therewith in a subject and/or a reduction in the severity of the onset of the infection and/or clinical symptom relative to what would occur in the absence of a method of the present invention. The prevention can be complete, e.g., the total absence of the infection and/or clinical symptom. The prevention can also be partial, such that the occurrence of the infection and/or clinical symptom in the subject and/or the severity of onset is less than what would occur in the absence of a method of the present invention. In certain embodiments, a method of the present invention prevents a viral, bacterial, protozoan, and/or fungal (e.g., onychomycosis and/or *Tinea pedis*) infection in a subject, such as, e.g., a fungal infection that can affect the skin and/or nail of the subject.

In some embodiments, a composition of the present invention (e.g., an admixture) may be administered in a prevention effective amount. A "prevention effective" amount as used herein is an amount that is sufficient to prevent (as defined herein) a viral, bacterial, protozoan, and/or fungal (e.g., onychomycosis and/or *Tinea pedis*) infection and/or clinical symptom in the subject. Those skilled in the art will appreciate that the level of prevention need not be complete, as long as some benefit is provided to the subject. In some embodiments, a prevention effective amount may be achieved by administering a composition of the present invention. In some embodiments, administration of a composition of the present invention does not produce systemic effects from the administration of nitric oxide, such as, for example, in a prevention effective amount.

The present invention finds use in both veterinary and medical applications. Subjects suitable to be treated with a method embodiment of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

Illustrative avians according to the present invention include chickens, ducks, turkeys, geese, quail, pheasant, ratites (e.g., ostrich) and domesticated birds (e.g., parrots and canaries), and birds in ovo.

A method of the present invention may also be carried out on animal subjects, particularly mammalian subjects such as mice, rats, dogs, cats, livestock and horses for veterinary purposes, and/or for drug screening and drug development purposes.

In some embodiments, the subject is "in need of" or "in need thereof" a method of the present invention, for example, the subject is in an at-risk population (e.g. the subject may be at-risk for or more susceptible to a fungal infection), the subject has findings typically associated with a viral, bacterial, protozoan, and/or fungal infection, is suspected to have a viral, bacterial, protozoan, and/or fungal infection, and/or the subject has a viral, bacterial, protozoan, and/or fungal infection. In some embodiments, a subject in need thereof has a viral, bacterial, protozoan, and/or fungal infection and/or a clinical sign or symptom associated therewith that may be treated with a method of the present invention. The present invention may be particularly suitable for children, adolescents, adults, and/or geriatric subjects.

In some embodiments, a composition of the present invention may be topically administered to a subject. A composition of the present invention may be administered and/or applied topically to any portion of a subject's skin and/or a nail of a subject. For example, a composition may be topically administered to a subject's hand, finger, foot, toe, nail (including the skin surrounding and/or under the nail), etc. In some embodiments, a composition of the present invention may be topically administered to at least a portion of a subject's hand, finger, foot, toe, and/or nail (e.g., fingernail and/or toenail). "Nail" as used herein may refer to any part of a fingernail and/or a toenail of a subject. A nail may be a full or partially intact nail. A nail may be a healthy nail, a diseased nail, and/or a damaged nail. In some embodiments, a method of the present invention may comprise applying a composition of the present invention to a nail and/or to the skin surrounding the nail such as, but not limited to, the cuticle, interdigital skin (i.e., interdigital webbing), and/or the skin of a hand and/or foot of a subject. In some embodiments, a composition of the present invention may be applied to a subject's nail, interdigital skin, and/or to the skin of a subject's hand and/or foot, and may treat and/or prevent a viral, bacterial, protozoan, and/or fungal infection in and/or on the skin and/or nail, such as, e.g., onychomycosis and/or *Tinea pedis*. In some embodiments, a composition of the present invention may be applied to a subject's nail and/or skin surrounding the nail where a pathogen e.g., fungus and/or mold) may live.

In some embodiments, a method and/or composition of the present invention may kill and/or inhibit the growth of one or more pathogens, such as, for example, one or more pathogens that may cause and/or be associated with a viral, bacterial, protozoan, and/or fungal infection.

Example fungal infections include, but are not limited to, onychomycosis, *Tinea pedis, Tinea capitis*, cutaneous candidiasis, *Tinea corporis*, and/or *Tinea cruris*. In some embodiments, a fungal infection may be caused by a dermatophyte, such as, for example, *T. rubrum* and/or *Trichophyton mentagrophytes*. In some embodiments, a composition of the present invention may be a topical monotherapy to treat and/or prevent a fungal infection, such as, for example, onychomycosis and/or *Tinea pedis*. In some embodiments, a method and/or composition of the present invention treats and/or prevents a fungal infection caused by a fungus and/or non-dermatophyte that is resistant to an azole and/or allylamine. In some embodiments, a method and/or composition of the present invention treats and/or prevents a fungal infection that is KOH positive as determined in accordance with a KOH test at baseline (i.e., at the start of treatment) and/or the subject has a negative fungal culture from a target lesion at baseline. In some embodiments, a method and/or composition of the present invention treats and/or prevents a fungal infection that is KOH positive as determined in accordance with a KOH test at baseline (i.e., at the start of treatment) and/or the subject has a positive fungal culture from a target lesion at baseline.

In some embodiments, a method and/or composition of the present invention may be used to treat and/or prevent onychomycosis in a subject and/or may inhibit and/or kill one or more dermatophyte(s), non-dermatophyte mold(s), and/or yeast(s) in and/or on the subject. Onychomycosis in the subject may be caused by and/or associated with one or more of the following dermatophytes, such as, but not limited to, *Arthroderma benhamiae, Epidermophyton floccosum, Microsporum* species (e.g., *Microsporum canis, cookei,* and *gypseum*), and *Trichophyton* species (e.g., *Trichophyton ajelloi, interdigitale, mentagrophytes, rubrum, schoenleinii, tonsurans, verrucosum,* and *violaceum*). In some embodiments, the dermatophyte is a *Trichophyton* species or *Epidermophyton* species. Alternatively or in addition, onychomycosis in the subject may be caused by and/or associated with one or more of the following non-dermatophyte molds, such as, but not limited to, *Acremonium* species (e.g., *Acremonium potronii* and *sclerotigenum*), *Alternaria* species (e.g., *Alternaria alternate*), *Arthrographis kalrae, Aspergillus* species (e.g., *Aspergillus versicolor, flavus, firmigatus nidulans, niger, nomius, sydowii,* and *terreus*), *Auxarthron* species (e.g., *Auxarthron ostraviense* and *umbrinum*), *Botryodiplodia theobromae, Chaetomium* species (e.g., *Chaetomium globosum*), *Cladosporium carrionii, Fusarium* species (e.g., *Fusarium oxysporum* and *solani*), *Geotrichum candidum, Hendersonula toruloidea, Lasiodiplodia theobromas, Nattrassia mangiferae, Neoscytalidium* species, *Nigrospora sphaerica, Onychocola* species (e.g., *Onychocola canadensis, pyrenochaeta,* and *unguis-hominis*), *Paecilomyces* species (e.g., *Paecilomyces variotti* and *Penicillium* species, *Phaeoacremonium parasiticum, Phialophora* species, *Pseudalleschria boydii, Pyrenochaeta unguis-hominis, Rhizopus* species, *Scopulariopsis* species (e.g., *Scopulariopsis brevicaulis* and *brumptii*), *Scytalidium* species (e.g., *Scytalidium dimidiatum* and *hyalimum*), *Thictromyces indigoticus, Tritirachitun* species (e.g., *Tritirachium oryzae*), and *Tinteinotia*. Alternatively or in addition, onychomycosis in the subject may be caused by and/or associated with one or more of the following yeast, such as, but not limited to, *Aureobasidium puliulans* (black yeast-like), *Candida* species (e.g., *Candida albicans, glabrate, guilliermondii, kefyr, krusei, lusitaniae, parapsilosis stellatoidea,* and *tropicalis*), *Cladophialophora boppli* (black yeast-like), *Cryptococcus neoformans, Exophiala oligosperma, Kodarnaea ohmeri, Malassezia* species (e.g., *Malassezia globose, sloglfiae,* and *pachydermatis*), *Rhodotorula* species (e.g., *Rhodotorula rula* and *minuta*), and *Trichosporon* species (e.g., *Trichasporon asahii, beigeleil,* and *mucoides*). In some embodiments, the yeast is a *Candida* species or *Malassezia* species.

In some embodiments, a method and/or composition of the present invention may be used to treat and/or prevent *Tinea pedis* in a subject and/or may inhibit and/or kill one or more dermatophyte(s), non-dermatophyte mold(s), and/or yeast(s) in and/or on the subject. Tinea pedis in the subject may be caused by and/or associated with one or more of the following dermatophytes, such as, but not limited to, *Arthroderma benhamiae, Epidermophyton floccosum, Microsporum canes, Microsporum gypseum, Trichophyton interdigitale, Trichophyton mentagrophytes, Trichophyton rubrum,* and *Trichophyton tonsurans*. Alternatively or in addition, *Tinea pedis* in the subject may be caused by and/or associated with one or more of the following non-dermatophyte molds, such as, but not limited to, *Aureobasidium pullulans, Aspergillus* species, *Fusarium* species, and *Hendersonula toruloidea*. Alternatively or in addition, *Tinea pedis* in the subject may be caused by and/or associated with one or more of the following yeast, such as, but not limited to, *Candida parapsilosis, Rhodotorula mucilaginosa, Phoma* species, *Debaryomyces hansenii,* and *Acremonium* species.

Provided according to some embodiments of the present invention is a method of treating and/or preventing a viral, bacterial, protozoan, and/or fungal infection in a subject. In some embodiments, a method of treating and/or preventing a viral, bacterial, protozoan, and/or fungal (e.g., onychomycosis and/or *Tinea pedis*) infection in a subject may comprise administering a composition of the present invention to the subject. In some embodiments, the method may comprise forming an admixture before and/or during the step of administering the composition. In some embodiments, a composition of the present invention may be administered onto skin and/or a nail of a subject 1 or more times (e.g., 1, 2, 3, 4, or more times) a day; every day; every other day; every 3, 4, 5, or 6 days; or once a week. In some embodiments, the composition may be administered onto skin and/or nail of a subject 1, 2 or 3 times a day for 1, 2, 3, or 4 weeks. In some embodiments, a composition of the present invention may be administered onto skin and/or a nail of a subject at least once daily for a period of 1, 2, 3, 4, 5, 6, 7, 8, 9, 10, 15, 20, 25, 30, 35, 40, 45, 50, or more weeks, or any range and/or individual value therein, to treat and/or prevent a viral, bacterial, protozoan, and/or fungal infection in the subject. In some embodiments, a composition of the present invention may be administered onto skin and/or a nail of a subject at least once daily for a period of less than 50 weeks, e.g., less than 48, 45, 40, 35, 30, 25, 20, 15, 12, 10, 6, 4, 3, or 2 weeks or less, or any range and/or individual value therein, to treat and/or prevent a viral, bacterial, protozoan, and/or fungal infection in the subject.

In some embodiments, a composition and/or method of the present invention may not stain and/or discolor the nail and/or skin of a subject to which it is in contact with and/or applied. In some embodiments, a composition and/or method of the present invention may deliver and/or administer nitric oxide to the nail and/or skin of a subject without staining and/or discoloring the nail and/or skin of the subject. For example, a composition and/or method of the present invention may not stain and/or discolor the subject's nail and/or skin yellow, brown, and/or black. In some embodiments, a composition and/or method of the present invention may stain and/or discolor less than about 10% (e.g., less than about 9%, 8%, 7%, 6%, 5%, 4%, 3%, 2%, 1%, or 0.5%) of the nail and/or skin in contact with the nail coaling composition and/or nail coating. Staining and/or discoloration of the nail and/or skin may be determined by visual comparison of the nail and/or skin prior to and after contact with the nail coating composition and/or nail coating.

A method of the present invention may have increased or improved efficacy in treating and/or preventing a viral, bacterial, protozoan, and/or fungal (e.g., onychomycosis and/or *Tinea pedis*) infection in and/or on the skin and/or nail of a subject by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, or more compared to a treatment in the absence of a method of the present invention (e.g., one that does not apply a composition of the present invention and/or a conventional treatment). In some embodiments, a method of applying a composition of the present invention to a subject's nail, interdigital skin, and/or to the skin of a subject's hand and/or foot may increase and/or improve efficacy in treating and/or preventing a viral, bacterial, protozoan, and/or fungal (e.g., onychomycosis and/or *Tinea pedis*) infection in and/or on the skin and/or nail of a subject by at least about 5%, 10%, 15%, 20%, 25%, 30%, 35%. 40%, 45%, 50%, 55%, 60%, 65%, 70%, 75%, 80%, 85%, 90%, 95%, 100%, 125%, 150%, 175%, 200%, or more compared to a treatment in the absence of a method of the present invention.

In some embodiments, a method of the present invention may decrease the rate of reinfection of a viral, bacterial, protozoan, and/or fungal (e.g., onychomycosis and/or *Tinea pedis*) infection in and/or on the skin and/or nail of a subject by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, or more compared to a treatment in the absence of a method of the present invention.

In some embodiments, a method of the present invention may reduce or decrease the treatment duration in a subject compared to a treatment in the absence of a method of the present invention (e.g., one that does not apply a composition of the present invention). For example, a method of the present invention may reduce or decrease the treatment duration in a subject by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, or more compared to a treatment in the absence of a method of the present invention.

In some embodiments, a method of the present invention may provide a decrease or reduction in at least one clinical symptom associated with a viral, bacterial, protozoan, and/or fungal (e.g., onychomycosis and/or *Tinea pedis*) infection (e.g., a reduction in the size and/or appearance of a benign lesion) in less time than compared to a treatment in the absence of a method of the present invention. In some embodiments, a subject may see a decrease or reduction in at least one clinical symptom associated with a viral, bacterial, protozoan, and/or fungal (e.g., onychomycosis and/or *Tinea pedis*) infection within 1, 2, 3, 4, 5, 6, 7, 8, 9, 10, 11, 12, 13, or more day(s) and/or week(s).

In some embodiments, a method of the present invention may prevent and/or reduce the appearance and/or size of a benign lesion. Example benign lesions include, but are not limited to, lesions caused by *T. rubrum*, such as, for example, scaly patches and red and/or brown lesions (e.g., those associated with jock itch). A method of the present invention may reduce the appearance and/or size of a benign lesion by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the appearance and/or size of a benign lesion prior to administering of a composition of the present invention. The appearance of the benign lesion may be evaluated visually, such as, but not limited to, by the subject and/or a physician. The size of the benign lesion may be determined using methods known to those of skill in the art.

A method of the present invention may reduce the number of benign lesions by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the number of benign lesions prior to administering of a composition of the present invention. The number of benign lesions may be evaluated visually, such as, but not limited to, by the subject and/or a physician. The number of benign lesions may be determined using methods known to those of skill in the art.

A method of the present invention may decrease the rate of recurrence of a viral, bacterial, protozoan, and/or fungal (e.g., onychomycosis and/or *Tinea pedis*) infection in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the rate of recurrence of the viral, bacterial, protozoan, and/or fungal (e.g., onychomycosis and/or *Tinea pedis*) infection in the absence of administering of a composition of the present invention. The rate of recurrence may be determined using methods known to those of skill in the art. For example, after a treatment of a viral, bacterial, protozoan, and/or fungal (e.g., onychomycosis and/or *Tinea pedis*) infection, reinfection may be determined after a given period of time to determine the rate of recurrence.

The present invention is explained in greater detail in the following non-limiting Examples.

EXAMPLES

Example 1

Example hydrogels and gels, Tables 1 and 2, respectively, were prepared Each hydrogel was evaluated individually for cosmetic aesthetics and in combination with a gel to form an admixture.

TABLE 1

Example hydrogel formulations.

| Ingredient | PHO-030 3.5 | PHO-031 4.0 | PHO-032 4.5 | PHO-033 3.5 | PHO-034 4.0 |
|---|---|---|---|---|---|
| Gantrez S-97 (Thickener) | 18.00% | 18.00% | — | 18.00% | 18.00% |
| Sodium Carboxymethyl-cellulose (Thickener) | 1.00% | 2.30% | 1.00% | 1.50% | 7.10% |
| Carbopol 980 (Thickener) | 0.25% | — | — | — | — |
| Carbopol 2020 ETD (Thickener) | — | — | — | 0.50% | — |
| Avicel RC-591 (Thickener) | — | 5.00% | 5.00% | — | 5.00% |
| Benzyl Alcohol (Co-Solvent) | — | — | — | 2.50% | 2.50% |
| Potassium Phosphate Monobasic (Buffering Agent) | 11.50% | 11.50% | 11.50% | 11.50% | 11.50% |
| EDTA (Chelating Agent) | 0.50% | — | — | 0.10% | — |
| Ethanol (Co-Solvent) | 5.00% | 5.00% | 5.00% | 5.00% | 5.00% |
| Cyclomethicone (Moisturizer) | 5.00% | — | 5.00% | 5.00% | — |

TABLE 1-continued

Example hydrogel formulations.

| Ingredient | PHO-030 3.5 | PHO-031 4.0 | PHO-032 4.5 | PHO-033 3.5 | PHO-034 4.0 |
|---|---|---|---|---|---|
| Phenoxyethanol (Co-Solvent) | — | — | — | 1.00% | 1.00% |
| Benzoic Acid (Preservative) | 0.10% | 0.10% | 0.10% | 0.10% | 0.10% |
| Purified Water (Solvent) | 58.65% | 58.10% | 72.40% | 54.80% | 54.60% |
| Total | 100.00% | 100.00% | 100.00% | 100.00% | 100.00% |

TABLE 2

Example gel formulations.

| Ingredient | 32% | 25% | 20% | 16% | 10% | 5% | 3.2% | Placebo |
|---|---|---|---|---|---|---|---|---|
| Elastomer 10 (Thickener) | 2.00% | 2.00% | 2.00% | 2.00% | 2.00% | 2.00% | 2.00% | 2.00% |
| Cyclomethicone (Emollient) | 17.00% | 20.00% | 21.00% | 22.00% | 23.00% | 23.50% | 24.00% | 24.50% |
| Hexylene Glycol (Humectant) | 14.00% | 16.00% | 18.00% | 19.00% | 21.00% | 22.00% | 23.00% | 23.00% |
| Nitricil™ NVN1 (Active Ingredient) | 32.00% | 25.00% | 20.00% | 16.00% | 10.00% | 5.00% | 3.20% | 0.00% |
| Klucel MF (Thickener) | 1.00% | 1.00% | 1.00% | 1.00% | 1.00% | 1.50% | 1.50% | 1.50% |
| Ethanol, Anhy. (Solvent) | 8.00% | 9.00% | 10.00% | 11.00% | 13.00% | 14.00% | 15.00% | 16.00% |
| Transcutol (Co-Solvent) | 26.00% | 27.00% | 28.00% | 29.00% | 30.00% | 32.00% | 31.30% | 33.00% |

Example 2

The penetration of nitric oxide through ex vivo human cadaver finger nails from NO-releasing formulations was evaluated using vertical diffusion cells. The in vitro vertical diffusion cell model is a valuable tool for the study of percutaneous penetration and determination of the pharmacokinetics of topically applied drugs. The model has also been adapted to be used for the ex vivo human cadaver fingernails mounted in specially designed vertical diffusion cells allowing the nail to be maintained at a temperature and hydration that are intended to represent in vivo conditions. The nail adapters were Neoflon, 28 mm wide by 34 mm long, and included o-rings and clamps to prevent leakage. A finite dose of each formulation was applied to the outer surface of the nail and absorption was measured by monitoring the rate of drug appearance in the receiving medium bathing the basal surface of the nail. Four human nail donors were selected in order to ensure donor specific permeation patterns would be identified and normalized.

Study Design
Apparatus: Vertical diffusion cells with nail adapters
Test Formulation 1: Nitricil™ NVN1 Cream, 32% (Table 3)+pH 4.5 hydrogel (Table 4)
Test Formulation 2: Nitricil™ NVN1 Gel, 32% (Table 2)+PHO-031 hydrogel (Table 1)
Test Formulation 3: Nitricil™ NVN1 Gel, 32% (Table 2)+PHO-033 hydrogel (Table 1)
Test Formulation 4: Nitricil™ NVN1 Gel, 32% (Table 2)+PHO-034 hydrogel (Table 1)
No. Fingernail Donors: 4
No. Fingernail Replicates: 6 nails per formulation, randomized for donor, gender, and finger
Fingernail Type: Ex vivo human fingernails
Nail Adapter Dose Area: 0.2 cm²
Diffusion Cell Volume: Approximately 8 mL
Temperature: 37° C.±1.0° C.
Application Amount: 8 µL (adjusted to nominal dosing area), the hydrogel (4 µL) and respective formulation (4 µL) were dosed separately onto the nail and mixed directly on the nail using the tip of the pipet.
Dosing intervals: Nails were dosed daily for 7 days within one hour of original dosing time. The original and subsequent dosing times were recorded in the study records.
Fingernail Cleansing Regimen: Daily
Sampling Intervals: On day 1: 500 µL receiving media was collected at 0 h, 1 h, 4 h, 8 h, 24 h. Each day following the start of the study, 500 µL of receiving media was collected once per day approximately one hour prior to the next dose application.
Sample Aliquot: Collect sample and replace with pre-warmed fresh medium
Receiving Medium: Phosphate buffered saline pH 7.4±0.1 (PBS) with 0.01% w/v sodium azide

TABLE 3

Nitricil™ NVN1 Cream, 32%

| Component | % w/w |
|---|---|
| Nitricil™ NVN1 Drug Substance | 32.00 |
| Petrolatum and polyethylene Crodabase SQ | 26.50 |
| White Petrolatum Super White Petrolatum USP | 26.50 |
| Medium chain triglycerides Miglyol 812 | 8.00 |
| Caprylocaproyl polyoxylglycerides Softigen 767 | 4.00 |
| Mineral oil Drakeol 34 USP | 3.00 |
| To Make Total | 100.0 |

TABLE 4 pH 4.5 hydrogel

| Component | % w/w |
|---|---|
| Purified water | 75.30 |
| Potassium phosphate monobasic | 11.80 |
| Glycerin | 10.00 |
| Sodium carboxymethylcellulose | 2.80 |
| Benzoic acid | 0.10 |
| To Make Total | 100.0 |

Test Procedure

The following test procedure was followed:

1.1 Set the Heater/Circulator to a temperature such that the media within the cells are maintained at 32° C.

1.2 Human, ex vivo, cadaver fingernails without obvious signs of nail disease that have been stored at −20° C. or lower will be used. Prior to dosing, thaw the nails at room temperature, clear of any underlying tissue, and rinse with water to remove any additional materials from the surface.

1.3 Apply nails to each nail adapter and secure in place. A small amount of silicone glue may be used to secure the nails in place. Allow the silicone glue to appropriately solidify prior to filling the cells with receiving medium.

1.4 Verify that the temperature of the media of a few cells is within 37±1° C. prior to filling the cells. Add receiving medium and a stir bar, to each cell such that the cell is full, and allow the cells and receiving medium to equilibrate at 37° C. The cell volumes are determined as described in the Cumulative Penetration Calculation section prior to initiating the study. Assemble the cells using nail adapters and clamps to secure nail adapters in place. Remove any air bubbles that were introduced during assembly of the cells.

1.5 Prior to dosing, each cell will be evaluated for leaks. If any leaks are identified, apply additional silicone glue to seal the leaks. A pre-dose sample will be collected for analysis, and an equal volume will be replaced with pre-warmed fresh media. Dose approximately 8 μL of formulation by pipette to each cell, covering the entire surface area of the nail. Occlude the sampling port to prevent evaporation during the study. The day of administration will be considered day one of the study. The actual dosing time will be recorded in the study records.

1.6 Each day for 7 days after the initial dosing, within one hour of the original dosing time, apply an additional equivalent dose to each cell as described previously. Prior to applying the additional dose, each cell is sampled as described in section 1.7 and cleansed according the following procedures:

For all groups, following receiving medium collection, cleanse the surface of the nails with a cotton tipped swab that has been moistened with water (not dripping wet), then cleanse with a dry cotton tipped swab. Discard the swabs after use.

1.7 At each of the sampling intervals, remove 500 μL receiving media before application of the next dose. After removing the media, add fresh receiving medium into the cell to replace the volume removed during sampling, and ensure the nail adapters and clamps are secure. Remove any air bubbles that were introduced during assembly of the cells.

An aliquot of the receptor fluid will be submitted for HPLC analysis. The remainder of the receptor fluid will be stored at −20° C.

Cumulative Penetration Calculation

The cumulative amount (Q) of active penetrating per surface area of nail is:

$$Q = \left\{ C_n V \sum_{i=1}^{n-1} C_i S \right\} / A$$

Where:

$Q$=Cumulative amount of active penetrated per surface area of nail ($\mu g/cm^2$)

$C_n$=Concentration of active (μg/mL) in the receiving medium determined at nth sampling interval (as determined by the HPLC analysis)

V=Volume of individual vertical diffusion cell $\sum_{i=1}^{n-1} C_i$ = Sum of concentrations of active (μg/mL) determined at sampling intervals 1 through $n - 1$ S=Volume of sampling aliquot (μL)

A=Surface area of nail ($cm^2$)

Penetration may be calculated for each day (C) and/or as a sum of cumulative penetration during the entire study period.

Results

Figure 2:
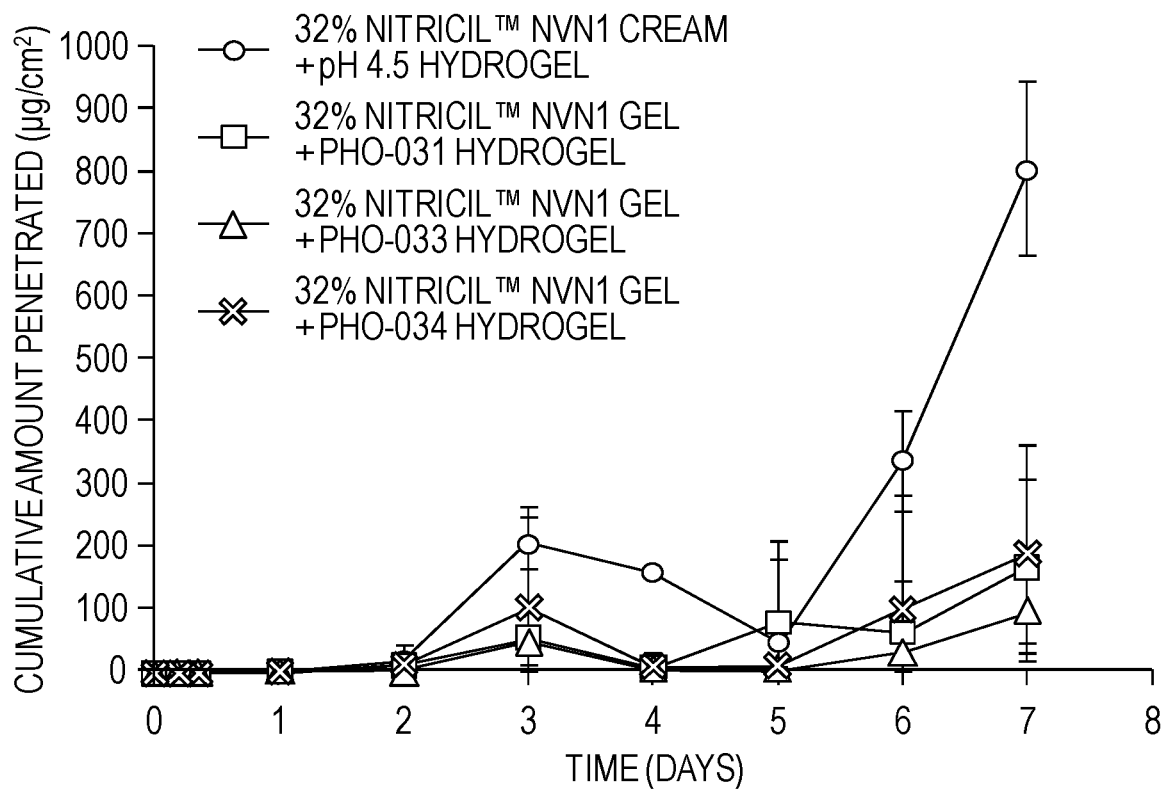
FIG. 2 is a graph showing the mean nitric oxide (NO) permeation (as detected by nitrite in the receptor medium) through human cadaver nails for NO-releasing formulations.

The mean nitric oxide permeation through human cadaver nails, as detected by nitrite in the receiving medium, is presented in Tables 5 and 6 and FIG. 2, and a standard vertical diffusion cell is shown in FIG. 1.

TABLE 5

Mean nitric oxide permeation through human cadaver nails on day 1.

| | Average Cumulative Amount (μg/cm²) (Average ± SD) | | | |
|---|---|---|---|---|
| Formulations | 1 hour | 4 hour | 8 hour | Day 1 |
| Test Formulation 1 | 0.00 ± 0.00 | 0.00 ± 0.00 | 2.41 ± 5.92 | 2.66 ± 5.26 |
| Test Formulation 2 | 0.00 ± 0.00 | 0.00 ± 0.00 | 0.00 ± 0.00 | 0.43 ± 1.05 |
| Test Formulation 3 | 0.00 ± 0.00 | 0.00 ± 0.00 | 0.00 ± 0.00 | 0.69 ± 1.70 |
| Test Formulation 4 | 0.00 ± 0.00 | 0.00 ± 0.00 | 0.00 ± 0.00 | 0.40 ± 0.99 |

TABLE 6

Mean nitric oxide permeation through human cadaver nails on days 2-7.

| Formulations | Average Amount ($\mu g/cm^2$) (Average ± SD) | | | | | |
| --- | --- | --- | --- | --- | --- | --- |
| | Day 2 | Day 3 | Day 4 | Day 5 | Day 6 | Day 7 |
| Test Formulation 1 | 17.54 ± 15.75 | 205.19 ± 154.18 | 159.81 ± 288.24 | 48.91 ± 51.62 | 337.47 ± 629.34 | 803.50 ± 470.76 |
| Test Formulation 2 | 14.21 ± 27.41 | 54.48 ± 42.02 | 7.48 ± 4.79 | 80.16 ± 130.28 | 63.90 ± 79.44 | 168.86 ± 138.88 |
| Test Formulation 3 | 0.46 ± 0.99 | 47.68 ± 52.05 | 4.12 ± 3.69 | 3.19 ± 3.34 | 29.67 ± 53.27 | 97.40 ± 50.91 |
| Test Formulation 4 | 10.96 ± 19.52 | 101.25 ± 162.06 | 12.65 ± 18.76 | 10.00 ± 11.15 | 100.84 ± 184.39 | 188.93 ± 172.43 |

The mean cumulative penetration after 8 days of dosing of each of four formulations indicated that nitrite appearance in the receptor medium was greatest from Nitricil™ NVN1 Cream, 32%+pH 4.5 hydrogel. The mean cumulative amount of 803.50±470.76 µg/cm² was several fold higher than from the remaining three formulations. Among the remaining three formulations, there was no observable difference between their absorption profiles.

For the lead formulation (Nitricil™ NVN1 Cream, 32%+ pH 4.5 hydrogel), quantifiable appearance of nitrite was detected after eight hours. For the remaining three formulations, nitrite was not detected until the 24 hour sample. Interestingly, the concentrations of nitrite in all cells peaked at the three day sampling; the concentrations then decreased until the 5-6 day samples, after which they began to increase again (FIG. 1).

During the HNC analysis, a set of standards was prepared and added to the autosampler tray along with the samples; however, because there were more samples and standards than the autosampler tray could hold, a set of standards and samples were frozen at −20° C. until additional space became available on the autosampler tray. Once space became available, the frozen standards and samples were thawed to room temperature, then added to the autosampler tray to complete the analysis. During review of the data, a clear reduction in peak area was observed for the standards that had been frozen after preparation and before analysis, indicating a potential freeze/thaw impact on samples containing nitrite. The overall impact on the study is unknown, as each sample was frozen immediately after collection during the nail penetration study, and stored at −20° C. until analysis. This phenomenon may have contributed to the penetration profile trend (i.e. increasing and decreasing over the eight days of sampling) observed in all formulations.

Example 3

Figure 3:
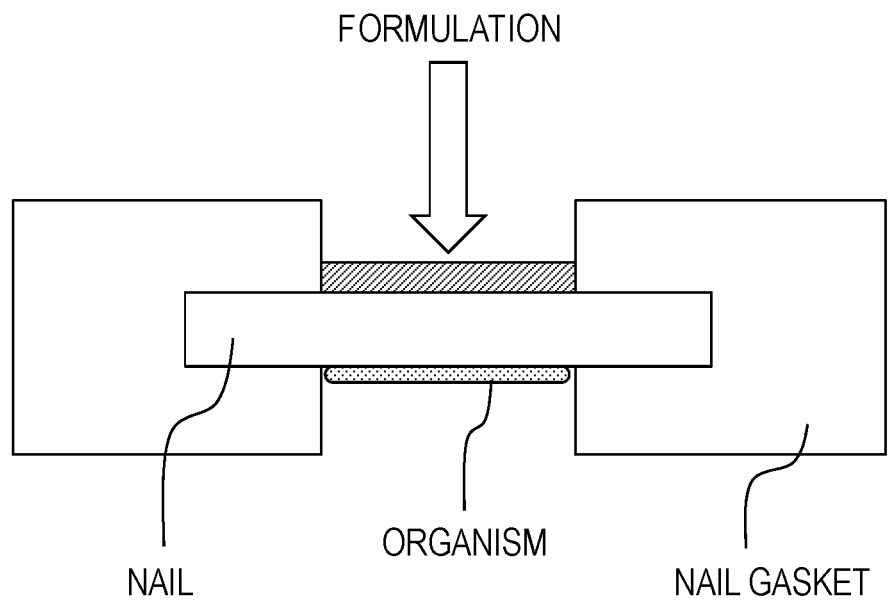
FIG. 3 is an illustration of a ChubTur® cell.

Different strengths of an NO-releasing gel in combination with a hydrogel in a 1:1 ratio were tested for effectiveness against *T. rubrum*. The underside of cadaver donor nails were infected with *T. rubrum* and each nail was subsequently mounted in ChubTur® cells as shown in FIG. 3. A receiver chamber under the nail was filled with sterile Ringer's solution, rubrum was grown at 25° C. for 14 days. After the 14-day incubation, a 50 µL dose of each admixture formulation was applied to the surface of a nail opposite of fungal inoculation (FIG. 3). Each formulation included the pH 4.0 hydrogel (PHO-033; (Table 1) that, prior to application, was premixed in a 1:1 ratio with either 3.2% Nitricil™ NVN1 Gel (Table 2) or 32% Nitricil™ NVN1 Gel (Table 2). The formulations remained on the nail for 24 hrs. After 24 hrs, excess formulation was removed and the nails were washed with deionized water. The nails were then dried with a cotton swab and air exposure (30 mins). Each formulation was then applied for a subsequent 24 hr exposure such that dosing continued for up to 7 days of topical application. However, on Days 1, 3, and 7 a subset of nails were subsequently removed from the ChubTur® cells and fungal viability was assessed using an ATP bioluminescence assay, where the results of ATP signal are inversely proportional to the percent fungal killing of *T. rubrum*.

Figure 4:
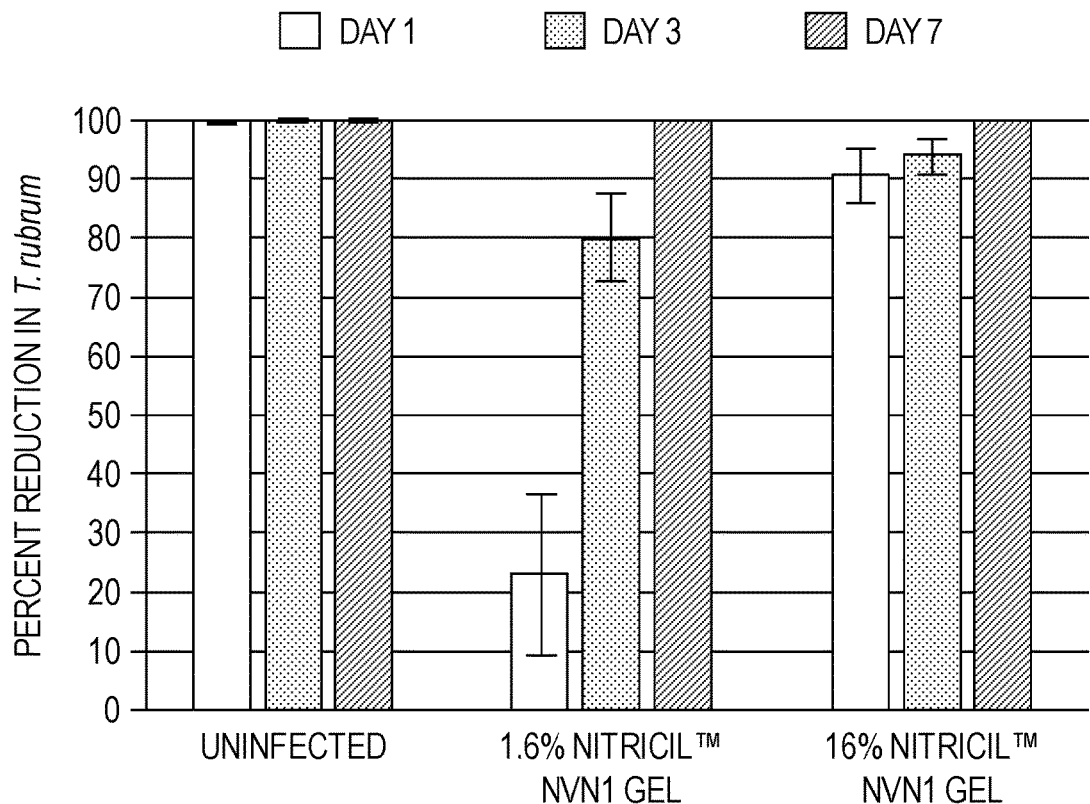
FIG. 4 is a graph showing the percent reduction in *T. rubrum* for NO-releasing formulations.

During the infected nail investigation, the antimicrobial efficacy of the high strength (16%) formulation (containing the 32% NVN1 gel) was significantly greater (p≤0.05) than that of the low strength (1.6%) formulation (containing the 32% NVN1 gel) after a single 1 day application of the test formulations (FIG. 4); however, despite the apparent differences between the antimicrobial efficacies of the low (80.03-98.58% kill of *T. rubrum*) and high strength (93.60-99.61% kill of organism) formulations following daily dosing for 3 and 7 days, there was no statistical difference in the percentage ATP recovery of these multiple dose regimens when compared as a whole population (p>0.05) (FIG. 4). The 3-day dosing regimen was able to completely clear the nail of the organism for the high strength (16%) formulation (p≤0.05), but not the low strength formulation which was statistically different to the t=3 days non-infected control (p>0.05). The 7-day dosing regimen was able to achieve complete kill of the organism with both the high and low strength formulations (p<0.05) (FIG. 4). Taken together these data indicate that following repeated application (at least 7 days) the antimicrobial efficacy observed with topical application of either low or high strength formulation is indistinguishable from one another. Therefore, in the clinical setting it is probable that repeated topical application of the lower strength formulation is likely to achieve significant antimicrobial efficacy.

Example 4

Nitricil™ NVN1, the lead candidate of the platform, was assessed for its spectrum of in vitro activity against a broad range of filamentous fungi and yeast species commonly associated with cutaneous fungal infections. Time-kill assays demonstrated that Nitricil™ NVN1 produced fungicidal activity in as early as 4 hours. Additionally, the penetration of several unique NO-releasing drug product formulations (gel, cream, lacquer) was evaluated following a single topical application to an infected human nail. Nitricil™ NVN1-containing topical formulations demonstrated effective fungal growth inhibition following a single treatment in the in vitro infected nail assay. Repeated topical application in this model demonstrated that lower strength doses of NO could achieve the same efficacy of higher strengths. Together, these results demonstrate that NO-releasing treatments, with rapid penetration of the nail plate and eradication of fungal infection, represent promising novel topical therapies for the treatment of onychomycosis and other superficial fungal infections.

Materials and Methods

Synthesis of Nitricil™ NVN1 Nitric Oxide-Releasing Macromolecules

Figure 5:
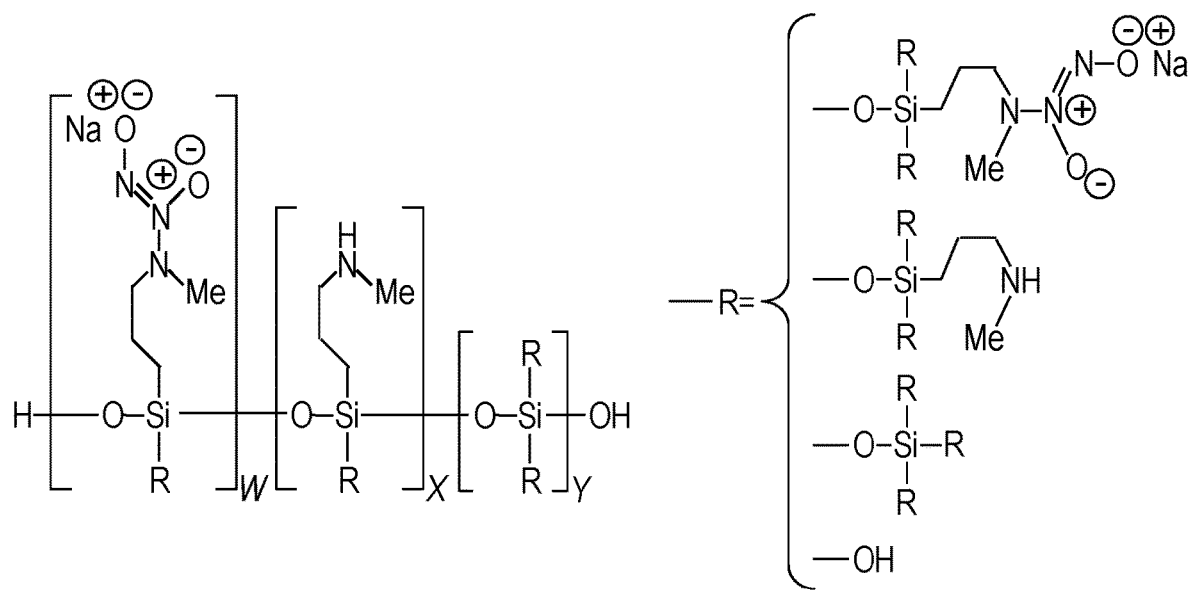
FIG. 5 illustrates the chemical structure of Nitricil™ NVN1 a polysiloxane nitric oxide-releasing macromolecule.

Nitricil™ NVN1 is a copolymer derived from aminoalkoxysilanes and alkylalkoxysilanes terminated with silanonals (FIG. 5). Nitricil™ NVN1 is formed from the co-condensation of N-methylaminopropyltimethoxysilane (MAP3), tetraethoyxysilane (TEOS) and N,N-methylaminopropyldiazeniumdiolate-trimethoxysilane sodium salt (MAP3-NONOate) via a sol-gel process, as described previously (Shin, et. al., J. Am. Chem. Soc. 2007, 129:4612-19), to create a network of siloxane bonds with organic functionality throughout. This process yields 5 µmol NO/mg of Nitricil™ NVN1 drug substance as determined via assessment of NO content under acidic conditions (pH 3) with a Sievers nitric oxide analyzer (Boulder, Colo.). Following jet milling the median particle size distribution (D50) value was 5.04 µm as determined by the Malvern Mastersizer 2000.

Nitricil™ NVN1 Drug Product Formulations

The nitric oxide-releasing active pharmaceutical ingredient can be formulated for topical delivery in a variety of drug product compositions. As the release of nitric oxide from the silica-based backbone is proton-initiated, exposure to moisture directly affects drug stability. To ensure stability Nitricil™ NVN1 is formulated in anhydrous compositions. To determine the most efficacious topical formulation for the delivery of nitric oxide to the nail bed and cutaneous tissues Nitricil™ NVN1 was formulated into a topical gel, ointment, or lacquer. Prior to topical application the stable active phase was mixed in a 1:1 ratio with a hydrogel phase providing the proton source necessary for initiation of nitric oxide release from the drug product. The Nitricil™ NVN1 Gel is a gel consisting of anhydrous ethanol, hexylene glycol, cyclomethicone, hydroxypropyl cellulose, Transcutol, Elastomer 10, and titanium dioxide. The Nitricil™ NVN1 Cream admixture results from the admixture of an Nitricil™ NVN1 petrolatum-based ointment with a benzoic acid-preserved potassium phosphate-based aqueous hydrogel phase. The Nitricil™ NVN1 Lacquer formulation results from the admixture of the ethylcellulose polymer-based Nitricil™ NVN1 Lacquer and a benzoic acid-preserved potassium phosphate-based aqueous hydrogel phase.

Microorganisms—Growth Media and Conditions

Challenge fungal species included both clinical isolates, as well as strains obtained from the American Type Culture Collection and National Collection of Pathogenic Fungi, representing *T. rubrum, T. mentragrophytes, Epidermophyton floccosum*, as well as *Fusarium, Candicia*, and *Malassezia* species.

Time-Kill and Minimum Inhibitory Concentration Determinations

Time-kill evaluations were determined following ASTM Method E2783-11. Briefly, a 0.1 mL aliquot of the fungal challenge prepared in 0.9% Sodium Chloride Irrigation was added to test tubes containing the appropriate concentration of Nitricil™ NVN1 test article dissolved in 10 mL of Tris pH 7.5-7.7 and vortexed. The challenge suspension was exposed to each test article concentration for 4 hours±5 minutes and 24 hours±5 minutes at 25° C.±2° C. After exposure, a 0.1 mL aliquot of the challenge suspension/test article was transferred to a new test tube containing 9.9 mL of neutralizing agent, Butterfield's phosphate buffer solution with product neutralizers (BBP++), and mixed thoroughly via vortex. Additionally, ten-fold dilutions were prepared in BBP++ as described. Duplicate aliquots ($10^{-1}$-$10^{-5}$) were plated on the appropriate agar and plates were incubated at 25° C.±2° C. until sufficient growth was observed, at which time viable counts were determined. The fungicidal effects (99.9% reduction in the original inoculum) were determined from the control population (CFU/mL) and the post-exposure population (CFU/mL) at each timed exposure.

The minimum inhibitory concentration (MIC) of Nitricil™ NVN1 was determined in vitro for 40 strains of fungi to determine the spectrum of antifungal activity. All MIC testing was conducted in accordance with the Clinical and Laboratory Standards Institute (CLSI) guidelines for antimicrobial testing of yeasts (M27-A2) and filamentous fungi (M38-A2), apart from the lipophilic *Malassezia* species, which were incubated in supplemented buffered RPMI-1640 medium. The challenge strains were exposed to a series of doubling dilutions of Nitricil™ NVN1 prepared in RPMI-1640 medium in triplicate. Fungal species were also challenged with ketoconazole, prepared in DMSO, as a comparator. Tubes were inoculated with fungal suspensions to a final concentration of $0.5$-$2.5 \times 10^3$ cells/mL for yeasts and $0.4$-$5.0 \times 10^4$ colony-forming units (CFU)/mL, for filamentous fungi. The MIC was determined following a 1- to 4-day incubation period.

In Vitro Antifungal Activity Under the Human Nail Plate

The growth inhibition of *T. rubrum* under the human nail plate was determined as previously described (Traynor, et. al, Pharm Pharmacol, 2010, 62:730-37). Distal nail clippings obtained from healthy human volunteers were individually infected on the underside of the nail with 5 µL of the *T. rubrum* suspension. The suspension was allowed to dry on the underside of the nail for 30 minutes in a laminar flow cabinet and subsequently was mounted onto the nail gasket within the ChubTur cell. The receiver chamber was then filled with an inert humidity control fluid (sterile Ringer's solution) and incubated at 25° C. for 14 days to establish the fungal nail infection. Following fungal incubation, the cells were closed with 50 µL of the test article admixture formulation, which was applied to the surface of the nail opposite to the *T. rubrum* inoculation. After 24 hours of topical treatment, the nails were cleaned of any residual formulation with a dry cotton swab and gently rinsed with deionized water. The nails were air-dried for 30 minutes prior to the application of the next topical dose to remove any moisture from the nail. After the completion of dosing, the ChubTur cells were removed from incubation and the ChubTur cells were dismantled. The nails were completely cleaned of all residual test article as described above and once clean the nails were subsequently placed in individual wells of a 96-well plate containing the ATP standard (55.0 ng/mL) and analyzed for the presence of ATP from the viable fungi via an ATP luminescence assay (BacTiter-Glo®) as previously described (Traynor, 2010). ATP calibration standards of known concentrations were prepared via sequential dilution of a stock ATP standard (1 mg/mL) in Ringer's solution. The wells of the 96-well plate were analyzed for the presence of ATP and the ATP recovery was compared to ATP standards and untreated infected positive controls. The mean percent ATP recovery form each test article formulation was compared to the infected control and statistical analyses performed using a one-way ANOVA with a post-hoc Tukey's test using a 95% confidence interval. This model was utilized in a preliminary experiment to assess the nail penetration and subsequent fungicidal activity of Nitricil™ NVN1 when formulated into a variety of topical drug products (gel, cream, or lacquer). In the preliminary experiment the fungicidal efficacy of each Nitricil™ NVN1-containing drug product formulation was assessed following a single topical application as this was hypothesized to allow the greatest differentiation amongst the given drug product formulations. 10% efinaconazole solution was included as the positive control in this single application experiment. A second experiment was conducted with the infected nail model to assess the time to complete fungal eradication following repeat dosing with varying strengths of a Nitricil™ NVN1 Admixture. In this experiment, 1.6% and 16.0% Nitricil™ NVN1 Gel Admixture (having a formulation consistent with those described in Example 6) were applied topically to infected nail mounted in ChubTur cells and fungal viability was assessed via ATP luminescence as described following 1, 3, or 7 days of daily topical application and compared to the ATP levels of non-infected and infected control nails incubated for the same durations.

Results

Figure 6:
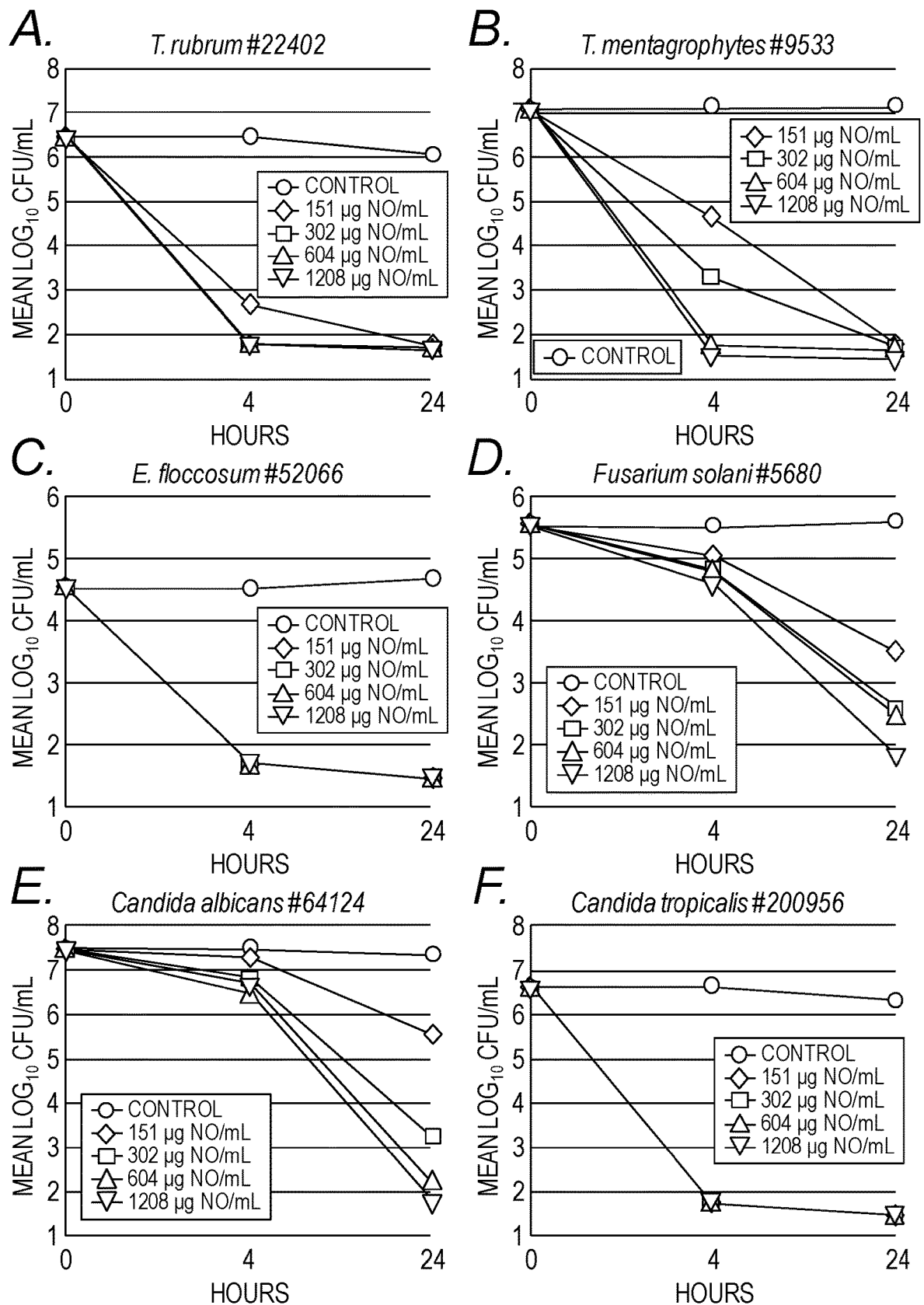
FIG. 6 shows time-kill curves for representative fungal isolates following exposures to Nitricil™ NVN1 from 4 to 24 hrs. Reported values are the mean of two independent assays and are reported as the mean log CFU/mL at the designated timepoint. Untreated Control; open circles and varying concentrations of Nitricil™ NVN1; closed symbols.

The broad-spectrum antifungal activity of Nitricil™ NVN1 was assessed via growth inhibition experiments against 40 different fungal strains per CLSI M27-A2 and M38-A2 methodology (CLSI, 2008) for assessment of yeasts and filamentous fungi respectively utilizing ketoconazole as the antifungal comparator. The MIC values for Nitricil™ NVN1 are summarized in Table 7 and ranged from 0.5 mg/mL to 8.0 mg/mL, equating to 75.5-1208 µg NO/mL, demonstrating a 16-fold range for all fungal species tested. The ketoconazole MIC values for all fungal species ranged by >500-fold under the same assay conditions (<0.063->32.0 ug/mL). The fungicidal activity of Nitricil™ NVN1 against a panel of fungal species was examined utilizing the time-kill assay to assess the rate and extent of fungal reduction following exposure to Nitricil™ NVN1 under static growth conditions. The time-kill curves following 24 hours of exposure to Nitricil™ NVN1 are shown in FIG. 6. The dermatophytes *T. mentagrophytes*, *E. floccosum*, and *T. rubrum* were especially susceptible to NITRICIL® NVN1, exhibiting a 99.9% fungal reduction following challenge with 2 mg/mL of NITRICIL® NVN1 (302 µg NO/mL) in as little as 4 hours exhibiting a rapid and robust effect following NO exposure. Following 24 hours of exposure, apart from *Fusarium solani*, fungicidal activity (99.9% fungal reduction) was observed for all tested species challenged with 302 µg NO/mL revealing the lingering antimicrobial effect of NO despite its short half-life.

TABLE 7

Antifungal activity of Nitricil ™ NVN1 (µg NO/ml) and ketoconazole (µg/ml) against a panel of fungal isolates.

| Fungal Strain | Nitricil ™ NVN1 MIC (µg NO/ml) | Ketoconazole MIC (µg/mL) |
|---|---|---|
| *Trichophyton rubrum* | | |
| NCPF #0113 | 75.5 | >32.0 |
| NCPF #0118 | 302 | <0.063 |
| NCPF #0295 | 604 | >32.0 |
| NCPF #5025 | 302 | >32.0 |
| ATCC #MYA-4438 | 302 | >32.0 |
| ATCC #10218 | 75.5 | <0.063 |
| ATCC #22402 | 151 | <0.063 |
| ATCC #28188 | 604 | 0.125 |
| ATCC #44697 | 302 | >32.0 |
| *Trichophyton mentagrophytes* | | |
| NCPF #0224 | 604 | 0.25 |
| NCPF #5024 | 1208 | 0.5 |

TABLE 7-continued

Antifungal activity of Nitricil ™ NVN1 (µg NO/ml) and ketoconazole (µg/ml) against a panel of fungal isolates.

| Fungal Strain | Nitricil ™ NVN1 MIC (µg NO/ml) | Ketoconazole MIC (µg/mL) |
|---|---|---|
| ATCC #9533 | 151 | 1.0 |
| ATCC #18749 | 75.5 | 0.125 |
| ATCC #28939 | 75.5 | 1.0 |
| *Epidermophyton floccosum* | | |
| NCPF #5011 | 1208 | >32.0 |
| NCPF #5012 | 302 | >32.0 |
| ATCC #38826 | 151 | 4.0 |
| ATCC #44685 | 604 | 0.125 |
| ATCC #52061 | 604 | 1.0 |
| ATCC #52063 | 302 | >32.0 |
| ATCC #52066 | 604 | >32.0 |
| *Fusarium* species | | |
| *Fusarium keratoplasticum* ATCC #36031 | 604 | >32.0 |
| *Fusarium oxysporum* ATCC #62705 | 302 | >32.0 |
| *Fusarium solani* ATCC #56480 | 604 | >32.0 |
| *Malassezia furfur* | | |
| NCPF #3349 | 75.5 | >32.0 |
| NCPF #8211 | 151 | 16.0 |
| ATCC #14521 | 151 | >32.0 |
| *Candida albicans* | | |
| ATCC #10231 | 151 | <0.063 |
| ATCC #58716 | 151 | 16.0 |
| ATCC #96901 | 151 | >32.0 |
| BLSI #112613Ca1 | 151 | >32.0 |
| BLSI #112613Ca2 | 151 | >32.0 |
| *Candida* species | | |
| *Candida lusitaniae* ATCC #200950 | 151 | <0.063 |
| *Candida tropicalis* NCPF #8760 | 1208 | 32.0 |

For the topical treatment of superficial fungal infections, the Nitricil™ NVN1 drug substance was formulated into a variety of topical products (gel, cream, or lacquer). Given the rapid fungicidal activity of Nitricil™ NVN1 observed in time-kill assays against the dermatophyte species, we sought to further explore the effectiveness of formulated NO-releasing drug products in an infected nail assay that simulates onychomycosis. The ability of various Nitricil™ NVN1-containing topical formulations to effectively penetrate the nail and exhibit antifungal activity was evaluated in vitro utilizing the infected nail assay (ChubTur test system) developed by MedPharm Ltd as this assay most accurately mimics the conditions of onychomycosis (Traynor, 2010). In this assay, *T. rubrum* was inoculated on the underside of a donor human nail plate and the infection was allowed to establish for 2 weeks. Infected fingernails were then mounted into modified vertical diffusion cells for the assessment of topical dosing. As a surrogate for fungal viability, ATP levels were assessed following topical application of candidate test formulations as ATP levels are inversely proportional to the percent fungal killing. This assay has been utilized previously to compare the effectiveness of Penlac, Loceryl, and a terbinafine spray formulation (Traynor, 2010). In this assay, fungicidal efficacy can only result from penetration of the applied topical solution through the nail to the resident fungal infection established beneath the nail. Initially a single topical application of the various Nitricil™ NVN1-containing formulations was assessed in this model to compare the nail penetration and fungicidal activity of each formulation. For comparison, the antifungal efficacy following a single application of 10% efinaconazole solution was also examined in this assay. Following a single 24-hr topical application there was no significant difference in the ATP recovery (surrogate for fungal viability) from any of the Nitricil™ NVN1-containing topical formulations or 10% efinaconazole solution. All tested formulations, including the positive control, demonstrated a mean percent fungal kill of 82% or higher after a single topical application (Table 8).

TABLE 8

Percentage kill of *T. rubrum* in the ChubTur ® infected nail investigation following a single topical application of various Nitricil ™ NVN1-containing topical formulations.

| Test Formulation | Mean Percentage Kill of *T. rubrum* vs. Infected Control, n = 6 ± SEM |
|---|---|
| 16% Nitricil ™ NVN1 Gel Admixture | 88.67 ± 4.72 |
| 16% Nitricil ™ NVN1 Cream | 91.62 ± 2.09 |
| 16% Nitricil ™ NVN1 Lacquer | 99.02 ± 0.30 |
| Jublia (10% efinaconazole solution) | 82.49 ± 6.71 |

Figure 7:
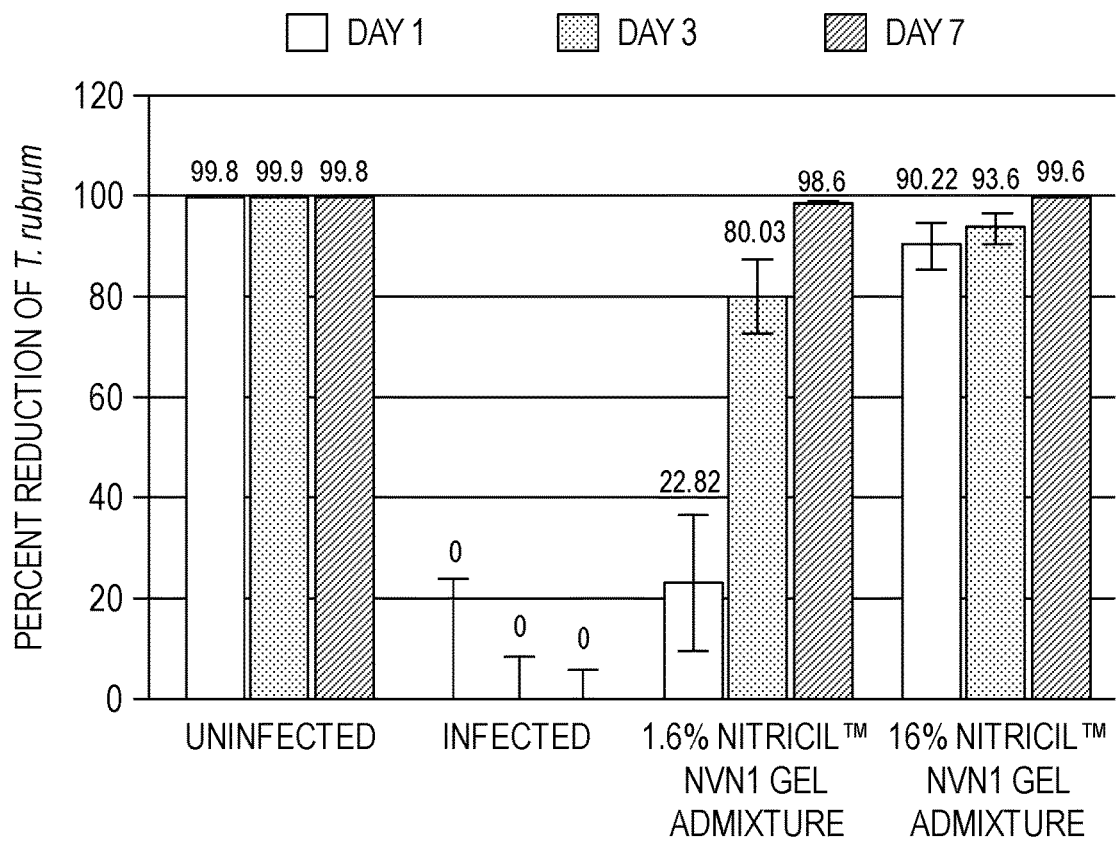
FIG. 7 shows graphs of the mean percent fungal reduction following repeated topical application of Nitricil™ NVN1 Gel in the ChubTur infected nail assay.

Nitricil™ NVN1 Gel Admixture is the drug product admixture formulation that results from the 1:1 mixing of the Nitricil™ NVN1-containing active gel phase and a hydrogel phase, Nitricil™ NVN1 Gel Admixture was selected for further characterization based on its physiochemical properties allowing for the concurrent application to cutaneous soft tissues, as well as the nail plate, for the treatment of onychomycosis and the ability of this formulation to be used for the treatment of large surface areas. This formulation was further optimized during development to reduce the alcohol content of the active phase in an effort to improve the tolerability in the intended patient population. The infected nail assay utilizing the ChubTur cells was performed a second time to determine the efficacy of low (1.6%) and high (16.0%) strength optimized. Nitricil™ NVN1 formulations against *T. rubrum* after repeat daily dosing for up to 7 days. FIG. 7 presents the percent fungal kill observed when *T. rubrum*-infected nails were treated with varying strengths of the Nitricil™ NVN1 Gel Admixture. The mean percentages of ATP recovered from the *T. rubrum* infected nails compared to the infected control after a single dose and 24-hour exposure were 77.15% and 9.78% for the low (1.6%) and the high (16%) Nitricil™ NVN1 Gel Admixture formulation, respectively equating to a 23% and 90% inhibition of fungal growth. Thus, there was a statistically significant ($p \leq 0.05$) difference in the ATP recovery observed following a single topical application with either strength Nitricil™ NVN1 Gel Admixture formulation when compared to the ATP recovery from untreated infected nails. Despite the potent antifungal activity observed with high strength (16.0%) Nitricil™ NVN1 Gel Admixture on Day 1, the ATP recovery was statistically different ($p \leq 0.05$) from the Day 1 non-infected control, indicating that complete fungal kill was not yet achieved. Following 3 days of daily treatment, comparable antifungal efficacy was observed following topical application of low (1.6%) and high (16.0%) strength Nitricil™ NVN1 Gel Admixtures with 80% and 93.6% fungal growth inhibition achieved, respectively (FIG. 7). However, only the high strength (16.0%) Nitricil™ NVN1 Gel Admixture was statistically equivalent ($p > 0.05$) to the Day 3 non-infected control, indicating that this formulation had achieved complete fungal kill under the limitations of this assay. After 7 days of daily dosing, both the low (1.6%) and the high (16.0%) strength Nitricil™ NVN1 Gel Admixtures achieved complete fungal kill as determined by ATP recovery values that were equivalent to the Day 7 non-infected controls ($p > 0.05$) (FIG. 7).

MIC assay results indicated a broad-spectrum of Nitricil™ NVN1 antifungal activity against a wide panel of yeast and filamentous fungi. All Nitricil™ NVN1 MIC values listed in Table 7 fell within a 16-fold range (0.5 mg/mL-8.0 mg/mL NV1000; 75.5-1208 µg NO/mL), demonstrating a narrow susceptibility profile over a diverse panel of fungi responsible for a large percentage of cutaneous infections in man. The ketoconazole results demonstrated a much wider concentration range (<0.063->32 ug/mL) needed to affect the same species of fungi. Additionally, unlike Nitricil™ NVN1, individual strains within a given fungal species showed disparate susceptibility to ketoconazole. Comparison between the two molecules reveal that the concentration of Nitricil™ NVN1 needed to inhibit fungal growth was an order of magnitude higher than the micromolar concentration observed following exposure to ketoconazole. This result is not unexpected as unlike ketoconazole NO is a highly reactive gaseous species exhibiting a short half-life, measured in seconds, in the physiological milieu. While wishing not to be bound to any particular theory, it is believed that the antimicrobial activity of Nitricil™ NVN1 is associated with the release of NO. Nitric oxide in Nitricil™ NVN1 represents 15% of the overall macromolecule on a weight-weight basis. Further, as a gaseous species NO will readily diffuse in all directions following proton-initiated release from the macromolecular backbone and a measurable proportion of the liberated NO is expected to be lost to the atmosphere upon topical application.

As both *Tinea pedis* and onychomycosis have high rates of recurrence, the fungicidal activity of a novel therapy provides perhaps even more meaningful information about the potential for treatment success than the growth inhibitory concentration determined by MIC assay. Therefore, the fungicidal efficacy of Nitricil™ NVN1 was evaluated against six representative dermatophytes and yeasts via time-kills studies using a similar concentration range employed in the MIC experiments.

As shown in FIG. 6 and Table 9, three of the six fungal species were effectively killed (>4-log reduction in CFU/mL) by Nitricil™ NVN1 concentrations of ≤604 µg NO/mL at the earliest 4 hour timepoint. The other three species showed complete kill by 24 hr exposure at Nitricil™ NVN1 concentrations of ≤1208 µg NO/mL. Despite the short half-life of NO, the MIC and kill curve results demonstrate the rapid and broad fungicidal potential of Nitricil™ NVN1.

TABLE 9

Percent fungal killing achieved following 4 hours of exposure to Nitricil ™ NVN1 for representative fungal isolates.

| 4 hrs | 151 µg NO/mL | 302 µg NO/mL | 604 µg NO/mL | 1208 µg NO/mL |
|---|---|---|---|---|
| *T. rubrum* | 99.97% | 99.99% | 99.99% | 99.99% |
| *T. mentagrophytes* | 99.63% | 99.98% | 99.999% | 99.999% |
| *E. floccosum* | 99.70% | 99.70% | 99.70% | 99.70% |
| *F. solani* | 64.21% | 77.35% | 87.83% | 78.30% |
| *C. albicans* | 31.49% | 73.96% | 81.29% | 87.94% |
| *C. tropicalis* | 99.99% | 99.99% | 99.99% | 99.99% |

Successful treatment of onychomycosis is fraught with difficulty due to several factors; the location of the fungal infection within the nail bed, the unique physical and chemical properties of the nail, and the co-existence of *Tinea pedis* which aids in recurrence of fungal infection. Among these factors, difficulty in finding compounds with the pharmacologic/pharmacokinetic profile to allow for adequate nail penetration and achieving therapeutic of drug levels, particularly after topical administration is the most challenging. The newest topical antifungal treatments, efinaconazole 10% solution and tavaborole 5% solution, specifically developed for the treatment of dermatophyte onychomycosis still only achieved complete cure rates of approximately 17% and 9%, respectively in pivotal phase 3 clinical trials (Gupta et al., J Drugs Dermatol. 2014, 13(7): 815-20; Elewski, et al., J Am. Acad. Dermatol. 2015 73(1): 62-9). The results of these studies with Nitricil™ NVN1 demonstrate the benefits of topical treatment with a formulation engineered to release gaseous NO that can be directly applied to the nail plate and surrounding cutaneous tissues. *T. rubrum* and *T. mentagrophytes*, the primary pathogens associated with both onychomycosis and *Tinea pedis*, were particularly susceptible to NO exposure. The results of the preliminary study assessing various Nitricil™ NVN1-containing topical formulations indicated that all topical NO-releasing formulations were equally effective, as no statistically significant differences in fungicidal efficacy based upon topical formulation (gel, cream, or lacquer) were observed. Each test article formulation demonstrated a mean percent fungal kill of at least 82% following a single topical application.

Most topical antifungal drugs that successfully treat cutaneous fungal infections do not effectively penetrate the nail plate and bed, thus limiting the ability to concurrently treat *Tinea pedis* and onychomycosis with a single topical antifungal agent (Hui, et al., J Pharm. Sci. 2007, 96(10):2622-31). The Nitricil™ NVN1 Gel Admixture formulation was selected for further development as it would allow for the concurrent treatment of both the nail and surrounding soft tissue of the foot, which might enhance the overall mycological cure rate observed following topical treatment in the clinical setting. Both the low (1.6%) and the high (16.0%) strength Nitricil™ NVN1 Gel Admixture formulations exhibited fungicidal activity as early as 24 hours following the first topical application. The 16.0% Nitricil™ NVN1 Gel Admixture formulation completely eradicated the fungal infection in the ChubTur model following 3 daily topical applications. Similarly, following a week of daily topical application, complete fungal eradication was also observed with 1.6% Nitricil™ NVN1 Gel Admixture. These findings demonstrate that repeated topical applications, as would occur clinically, can achieve comparable antifungal efficacy following treatment with Nitricil™ NVN1 Gel Admixture.

These results suggest that the unique mechanism of action and molecular characteristics of a topical NO-releasing gel may produce high rates of fungicidal efficacy against a wide range of fungal species. NO's antimicrobial activities include generation of both oxidative and nitrosative species. These species interact with a variety of molecular targets including iron-sulfur thiols, tyrosine residues, membrane lipids, and DNA bases providing numerous fungal targets to act upon. While not wishing to be bound to any particular theory, the ability of NO and its associated gaseous species to rapidly migrate through the nail plate, and through microbial lipid membranes, demonstrates that Nitricil™ NVN1 Gel Admixture may be an effective topical treatment for superficial fungal infections such as onychomycosis. The potential to simultaneously treat both the nail plate and the surrounding cutaneous tissues with a single topical formulation could improve the clinical outcome as compared to the standard of care for both *Tinea pedis* and onychomycosis, which is particularly important as the prevalence of onychomycosis is increasing in the elderly and diabetic populations where more advanced disease occurs with associated morbidities such as wounds, cellulitis, and compromised ambulation.

Example 5

A phase 2, multi-center, double-blind, randomized, vehicle-controlled study is conducted in approximately 220 non immunocompromised adult subjects with interdigital *Tinea pedis*. Subjects will apply the investigational product (IP) (Nitricil™ NVN1 Gel Admixture or Vehicle Gel) to the interdigital areas and all affected and immediate surrounding areas of one or both feet once daily for 2 weeks, followed by a 4-week post-treatment observation period.

Study Type: Interventional
Study Design: Allocation: Randomized
Intervention Model: Parallel Assignment
Masking: Double Blind (Subject, Investigator)
Primary Purpose: Treatment
Primary Outcome Measures:
Fungal culture result [Time Frame: 14 days], Negative fungal culture from target lesion
Secondary Outcome Measures:
Clinical cure [Time Frame: 42 days], Amelioration of signs and symptoms of *Tinea pedis*
Mycological cure [Time Frame: 42 days], No evidence of fungal infection based on skin scraping and culture
Other Outcome Measures:
Incidence of treatment-emergent adverse events [Time Frame: 42 days], Summary of treatment emergent adverse events by treatment group

| Arms | Assigned Interventions |
|---|---|
| Experimental: 2% Nitricil ™ NVN1 Gel Admixture (provided in Example 6) | Drug: 2% Nitricil ™ NVN1 Gel Admixture once daily |
| Experimental: 4% Nitricil ™ NVN1 Gel Admixture (provided in Example 6) | Drug: 4% Nitricil ™ NVN1 Gel Admixture once daily |
| Experimental: 16% Nitricil ™ NVN1 Gel Admixture (provided in Example 6) | Drug: 16% Nitricil ™ NVN1 Gel Admixture once daily |
| Placebo Comparator: Vehicle Gel | Drug: Vehicle Gel once daily |

Eligibility
Ages Eligible for Study: 18 years to 70 Years (Adult, Senior)
Sexes Eligible for Study: All
Accepts Healthy Volunteers: No
Inclusion Criteria: Otherwise healthy male and female subjects with clinical diagnosis of interdigital *T. pedis*. *T. pedis* provisionally confirmed at baseline by a positive KOH wet mount for segmented fungal hyphae on skin scraping from the target site
Exclusion Criteria: Women who are pregnant or nursing or planning on becoming pregnant. Subjects with onychomycosis or moccasin-type *T. pedis*. Subjects using topical or systemic anti-fungal agents.
Enrollment: 222
Results from the Primary Outcome Measures: The results from the primary outcome measures are provided in Tables 10 and 11. In pre-specified populations including the per protocol population, subjects treated with SB208 4% and 16% once daily demonstrated a statistically significant (p<0.05) difference from vehicle on the primary efficacy outcome, a negative fungal culture at Day 14. No subjects discontinued treatment due to adverse events.

Results from the Secondary Outcome Measures: The results from the secondary outcome measures are provided in Tables 12-17.

TABLE 10

Subject Disposition (All Randomized Subjects)

| Disposition | SB208 2% | SB208 4% | SB208 16% | SB208 Total | Vehicle | Total |
|---|---|---|---|---|---|---|
| Subjects Randomized | 56 | 55 | 55 | 166 | 56 | 222 |
| Subjects Included in Intent-to-Treat (Safety) Analysis | 56 (100.0%) | 55 (100.0%) | 55 (100.0%) | 166 (100.0%) | 56 (100.0%) | 222 (100.0%) |
| Subjects Included in Modified Intent-to-Treat Analysis | 35 (62.5%) | 37 (67.3%) | 36 (65.5%) | 108 (65.1%) | 35 (62.5%) | 143 (64.4%) |
| Subjects Included in Per-Protocol Analysis | 29 (51.8%) | 29 (52.7%) | 30 (54.5%) | 88 (53.0%) | 31 (55.4%) | 119 (53.6%) |
| Subjects Completed study | 40 (71.4%) | 45 (81.8%) | 41 (74.5%) | 126 (75.9%) | 42 (75.0%) | 168 (75.7%) |
| Subjects Discontinued | 16 (28.6%) | 10 (18.2%) | 14 (25.5%) | 40 (24.1%) | 14 (25.0%) | 54 (24.3%) |
| Reason for Discontinuation: | | | | | | |
| Negative baseline culture | 15 (26.8%) | 9 (16.4%) | 14 (25.5%) | 38 (22.9%) | 14 (25.0%) | 52 (23.4%) |
| Adverse event | 0 (0.0%) | 0 (0.0%) | 0 (0.0%) | 0 (0.0%) | 0 (0.0%) | 0 (0.0%) |
| Subject decision/withdrawal of consent | 0 (0.0%) | 1 (1.8%) | 0 (0.0%) | 1 (0.6%) | 0 (0.0%) | 1 (0.5%) |
| Significant protocol violation or non-compliance with protocol | 0 (0.0%) | 0 (0.0%) | 0 (0.0%) | 0 (0.0%) | 0 (0.0%) | 0 (0.0%) |
| Non-compliant use of IP | 0 (0.0%) | 0 (0.0%) | 0 (0.0%) | 0 (0.0%) | 0 (0.0%) | 0 (0.0%) |
| Condition worsens and requires alternative or supplemental therapy for treatment of tinea pedis during the study | 0 (0.0%) | 0 (0.0%) | 0 (0.0%) | 0 (0.0%) | 0 (0.0%) | 0 (0.0%) |
| Lost to follow-up | 1 (1.8%) | 0 (0.0%) | 0 (0.0%) | 1 (0.6%) | 0 (0.0%) | 1 (0.5%) |
| Subject's IP code is unblinded | 0 (0.0%) | 0 (0.0%) | 0 (0.0%) | 0 (0.0%) | 0 (0.0%) | 0 (0.0%) |
| Subject became pregnant | 0 (0.0%) | 0 (0.0%) | 0 (0.0%) | 0 (0.0%) | 0 (0.0%) | 0 (0.0%) |
| Investigator discretion | 0 (0.0%) | 0 (0.0%) | 0 (0.0%) | 0 (0.0%) | 0 (0.0%) | 0 (0.0%) |
| Other | 0 (0.0%) | 0 (0.0%) | 0 (0.0%) | 0 (0.0%) | 0 (0.0%) | 0 (0.0%) |

TABLE 11

Primary Efficacy Analysis: Proportion of Subjects with Negative Fungal Culture at Visit 2/Day 14

| Missing Data Handling | Statistics | SB208 2% | SB208 4% | SB208 16% | SB208 Total | Vehicle | p-value of SB208 Total vs. Vehicle[1] |
|---|---|---|---|---|---|---|---|
| | | Modified Intent-to-Treat Population | | | | | |
| Confirmed | N | 31 | 31 | 31 | 93 | 33 | |
| | n (%) Subjects with Negative Fungal Culture | 19 (61.3%) | 25 (80.6%) | 23 (74.2%) | 67 (72.0%) | 15 (45.5%) | 0.004 |
| | p-value of SB208 vs. Vehicle[1] | 0.209 | 0.002 | 0.016 | | | |
| | | Per-Protocol Population | | | | | |
| LOCF | N | 29 | 29 | 30 | 88 | 31 | |
| | n (%) Subjects with Negative Fungal Culture | 17 (58.6%) | 23 (79.3%) | 23 (76.7%) | 63 (71.6%) | 13 (41.9%) | 0.003 |
| | p-value of SB208 vs. Vehicle[1] | 0.204 | 0.002 | 0.008 | | | |

Modified Intent-to-Treat: subjects with a positive fungal culture at Baseline. Confirmed analysis only includes subjects with evaluable culture result at Day 14.

Per-Protocol: Subjects with no significant protocol violations.

LOCF: last observation carried forward.

[1]P-values for treatment comparisons from Cochran-Mantel-Haenszel test for general association adjusting for site.

TABLE 12

Secondary Efficacy Analysis: Proportion of Subjects with Clinical Cure at Visit 3/Day 42

| Missing Data Handling | Statistics | SB208 2% | SB208 4% | SB208 16% | SB208 Total | Vehicle | p-value of SB208 Total vs. Vehicle[1] |
|---|---|---|---|---|---|---|---|
| Modified Intent-to-Treat Population | | | | | | | |
| LOCF | N | 35 | 37 | 36 | 108 | 35 | |
| | n (%) Subjects with Clinical Cure* | 5 (14.3%) | 11 (29.7%) | 9 (25.0%) | 25 (23.1%) | 5 (14.3%) | 0.280 |
| | p-value of SB208 vs. Vehicle[1] | 1.000 | 0.152 | 0.253 | | | |
| Observed | N | 34 | 37 | 36 | 107 | 35 | |
| | n (%) Subjects with Clinical Cure* | 5 (14.7%) | 11 (29.7%) | 9 (25.0%) | 25 (23.4%) | 5 (14.3%) | 0.279 |
| | p-value of SB208 vs. Vehicle[1] | 0.988 | 0.152 | 0.253 | | | |
| Per-Protocol Population | | | | | | | |
| LOCF | N | 29 | 29 | 30 | 88 | 31 | |
| | n (%) Subjects with Clinical Cure* | 5 (17.2%) | 10 (34.5%) | 8 (26.7%) | 23 (26.1%) | 5 (16.1%) | 0.224 |
| | p-value of SB208 vs. Vehicle[1] | 0.887 | 0.120 | 0.234 | | | |
| Observed | N | 29 | 29 | 30 | 88 | 31 | |
| | n (%) Subjects with Clinical Cure* | 5 (17.2%) | 10 (34.5%) | 8 (26.7%) | 23 (26.1%) | 5 (16.1%) | 0.224 |
| | p-value of SB208 vs. Vehicle[1] | 0.887 | 0.120 | 0.234 | | | |

*Clinical cure is defined as a total signs/symptoms severity score of no more than 2 with no individual severity score greater than 1 on the 4-point scale.
[1]P-values for treatment comparisons from Cochran-Mantel-Haenszel test for general association adjusting for site.

TABLE 13

Secondary Efficacy Analysis: Proportion of Subjects with Mycological Cure at Visit 3/Day 42

| Missing Data Handling | Statistics | SB208 2% | SB208 4% | SB208 16% | SB208 Total | Vehicle | p-value of SB208 Total vs. Vehicle[1] |
|---|---|---|---|---|---|---|---|
| Modified Intent-to-Treat Population | | | | | | | |
| LOCF | N | 35 | 37 | 36 | 108 | 35 | |
| | n (%) Subjects with Mycological Cure* | 12 (34.3%) | 18 (48.6%) | 21 (58.3%) | 51 (47.2%) | 11 (31.4%) | 0.079 |
| | p-value of SB208 vs. Vehicle[1] | 0.798 | 0.103 | 0.019 | | | |
| Confirmed | N | 34 | 35 | 34 | 103 | 34 | |
| | n (%) Subjects with Mycological Cure* | 12 (35.3%) | 18 (51.4%) | 20 (58.8%) | 50 (48.5%) | 11 (32.4%) | 0.071 |
| | p-value of SB208 vs. Vehicle[1] | 0.795 | 0.076 | 0.020 | | | |
| Per-Protocol Population | | | | | | | |
| LOCF | N | 29 | 29 | 30 | 88 | 31 | |
| | n (%) Subjects with Mycological Cure* | 8 (27.6%) | 16 (55.2%) | 17 (56.7%) | 41 (46.6%) | 10 (32.3%) | 0.166 |
| | p-value of SB208 vs. Vehicle[1] | 0.673 | 0.054 | 0.074 | | | |
| Confirmed | N | 29 | 28 | 29 | 86 | 31 | |
| | n (%) Subjects with Mycological Cure* | 8 (27.6%) | 16 (57.1%) | 16 (55.2%) | 40 (46.5%) | 10 (32.3%) | 0.166 |
| | p-value of SB208 vs. Vehicle[1] | 0.673 | 0.042 | 0.086 | | | |

*Mycological cure is defined as a negative KOH wet mount and a negative fungal culture.
[1]P-values for treatment comparisons from Cochran-Mantel-Haenszel test for general association adjusting for site.

TABLE 14

Secondary Efficacy Analysis: Proportion of Subjects with Therapeutic Cure at Visit 3/Day 42

| Missing Data Handling | Statistics | SB208 2% | SB208 4% | SB208 16% | SB208 Total | Vehicle | p-value of SB208 Total vs. Vehicle[1] |
|---|---|---|---|---|---|---|---|
| Modified Intent-to-Treat Population | | | | | | | |
| LOCF | N | 35 | 37 | 36 | 108 | 35 | |
| | n (%) Subjects with Therapeutic Cure* | 2 (5.7%) | 7 (18.9%) | 4 (11.1%) | 13 (12.0%) | 3 (8.6%) | 0.606 |
| | p-value of SB208 vs. Vehicle[1] | 0.646 | 0.247 | 0.729 | | | |
| Confirmed | N | 34 | 37 | 36 | 107 | 35 | |
| | n (%) Subjects with Therapeutic Cure* | 2 (5.9%) | 7 (18.9%) | 4 (11.1%) | 13 (12.1%) | 3 (8.6%) | 0.604 |
| | p-value of SB208 vs. Vehicle[1] | 0.660 | 0.247 | 0.729 | | | |

TABLE 14-continued

Secondary Efficacy Analysis: Proportion of Subjects with Therapeutic Cure at Visit 3/Day 42

| Missing Data Handling | Statistics | SB208 2% | SB208 4% | SB208 16% | SB208 Total | Vehicle | p-value of SB208 Total vs. Vehicle[1] |
|---|---|---|---|---|---|---|---|
| | | Per-Protocol Population | | | | | |
| LOCF | N | 29 | 29 | 30 | 88 | 31 | |
| | n (%) Subjects with Therapeutic Cure* | 2 (6.9%) | 7 (24.1%) | 3 (10.0%) | 12 (13.6%) | 3 (9.7%) | 0.547 |
| | p-value of SB208 vs. Vehicle[1] | 0.706 | 0.152 | 0.919 | | | |
| Confirmed | N | 29 | 29 | 30 | 88 | 31 | |
| | n (%) Subjects with Therapeutic Cure* | 2 (6.9%) | 7 (24.1%) | 3 (10.0%) | 12 (13.6%) | 3 (9.7%) | 0.547 |
| | p-value of SB208 vs. Vehicle[1] | 0.706 | 0.152 | 0.919 | | | |

*Therapeutic cure is defined as having both clinical cure and mycological cure.
[1]P-values for treatment comparisons from Cochran-Mantel-Haenszel test for general association adjusting for site.

TABLE 15

Secondary Efficacy Analysis: Proportion of Subjects with Clinical Cure at Visit 2/Day 14

| Missing Data Handling | Statistics | SB208 2% | SB208 4% | SB208 16% | SB208 Total | Vehicle | p-value of SB208 Total vs. Vehicle[1] |
|---|---|---|---|---|---|---|---|
| | | Modified Intent-to-Treat Population | | | | | |
| LOCF | N | 35 | 37 | 36 | 108 | 35 | |
| | n (%) Subjects with Clinical Cure* | 4 (11.4%) | 1 (2.7%) | 4 (11.1%) | 9 (8.3%) | 2 (5.7%) | 0.649 |
| | p-value of SB208 vs. Vehicle[1] | 0.386 | 0.463 | 0.418 | | | |
| Observed | N | 35 | 36 | 36 | 107 | 35 | |
| | n (%) Subjects with Clinical Cure* | 4 (11.4%) | 1 (2.8%) | 4 (11.1%) | 9 (8.4%) | 2 (5.7%) | 0.649 |
| | p-value of SB208 vs. Vehicle[1] | 0.386 | 0.463 | 0.418 | | | |
| | | Per-Protocol Population | | | | | |
| LOCF | N | 29 | 29 | 30 | 88 | 31 | |
| | n (%) Subjects with Clinical Cure* | 3 (10.3%) | 1 (3.4%) | 4 (13.3%) | 8 (9.1%) | 2 (6.5%) | 0.626 |
| | p-value of SB208 vs. Vehicle[1] | 0.564 | 0.555 | 0.292 | | | |
| Observed | N | 29 | 29 | 30 | 88 | 31 | |
| | n (%) Subjects with Clinical Cure* | 3 (10.3%) | 1 (3.4%) | 4 (13.3%) | 8 (9.1%) | 2 (6.5%) | 0.626 |
| | p-value of SB208 vs. Vehicle[1] | 0.564 | 0.555 | 0.292 | | | |

*Clinical cure is defined as a total signs/symptoms severity score of no more than 2 with no individual severity score greater than 1 on the 4-point scale.
[1]P-values for treatment comparisons from Cochran-Mantel-Haenszel test for general association adjusting for site.

TABLE 16

Secondary Efficacy Analysis: Proportion of Subjects with Mycological Cure at Visit 2/Day 14

| Missing Data Handling | Statistics | SB208 2% | SB208 4% | SB208 16% | SB208 Total | Vehicle | p-value of SB208 Total vs. Vehicle[1] |
|---|---|---|---|---|---|---|---|
| | | Modified Intent-to-Treat Population | | | | | |
| LOCF | N | 35 | 37 | 36 | 108 | 35 | |
| | n (%) Subjects with Mycological Cure* | 11 (31.4%) | 16 (43.2%) | 17 (47.2%) | 44 (40.7%) | 8 (22.9%) | 0.038 |
| | p-value of SB208 vs. Vehicle[1] | 0.414 | 0.035 | 0.022 | | | |
| Confirmed | N | 32 | 32 | 32 | 96 | 34 | |
| | n (%) Subjects with Mycological Cure* | 11 (34.4%) | 16 (50.0%) | 17 (53.1%) | 44 (45.8%) | 8 (23.5%) | 0.013 |
| | p-value of SB208 vs. Vehicle[1] | 0.305 | 0.009 | 0.010 | | | |
| | | Per-Protocol Population | | | | | |
| LOCF | N | 29 | 29 | 30 | 88 | 31 | |
| | n (%) Subjects with Mycological Cure* | 10 (34.5%) | 14 (48.3%) | 17 (56.7%) | 41 (46.6%) | 6 (19.4%) | 0.005 |
| | p-value of SB208 vs. Vehicle[1] | 0.194 | 0.007 | 0.003 | | | |
| Confirmed | N | 29 | 29 | 30 | 88 | 31 | |
| | n (%) Subjects with Mycological Cure* | 10 (34.5%) | 14 (48.3%) | 17 (56.7%) | 41 (46.6%) | 6 (19.4%) | 0.005 |
| | p-value of SB208 vs. Vehicle[1] | 0.194 | 0.007 | 0.003 | | | |

*Mycological cure is defined as a negative KOH wet mount and a negative fungal culture.
[1]P-values for treatment comparisons from Cochran-Mantel-Haenszel test for general association adjusting for site.

TABLE 17

Secondary Efficacy Analysis: Proportion of Subjects with Therapeutic Cure at Visit 2/Day 14

| Missing Data Handling | Statistics | SB208 2% | SB208 4% | SB208 16% | SB208 Total | Vehicle | p-value of SB208 Total vs. Vehicle[1] |
|---|---|---|---|---|---|---|---|
| | | Modified Intent-to-Treat Population | | | | | |
| LOCF | N | 35 | 37 | 36 | 108 | 35 | |
| | n (%) Subjects with Therapeutic Cure* | 2 (5.7%) | 1 (2.7%) | 4 (11.1%) | 7 (6.5%) | 1 (2.9%) | 0.439 |
| | p-value of SB208 vs. Vehicle[1] | 0.555 | 0.909 | 0.176 | | | |
| Confirmed | N | 34 | 36 | 36 | 106 | 35 | |
| | n (%) Subjects with Therapeutic Cure* | 2 (5.9%) | 1 (2.8%) | 4 (11.1%) | 7 (6.6%) | 1 (2.9%) | 0.430 |
| | p-value of SB208 vs. Vehicle[1] | 0.528 | 0.909 | 0.176 | | | |
| | | Per-Protocol Population | | | | | |
| LOCF | N | 29 | 29 | 30 | 88 | 31 | |
| | n (%) Subjects with Therapeutic Cure* | 2 (6.9%) | 1 (3.4%) | 4 (13.3%) | 7 (8.0%) | 1 (3.2%) | 0.351 |
| | p-value of SB208 vs. Vehicle[1] | 0.501 | 1.000 | 0.114 | | | |
| Confirmed | N | 29 | 29 | 30 | 88 | 31 | |
| | n (%) Subjects with Therapeutic Cure* | 2 (6.9%) | 1 (3.4%) | 4 (13.3%) | 7 (8.0%) | 1 (3.2%) | 0.351 |
| | p-value of SB208 vs. Vehicle[1] | 0.501 | 1.000 | 0.114 | | | |

*Therapeutic cure is defined as having both clinical cure and mycological cure.
[1]P-values for treatment comparisons from Cochran-Mantel-Haenszel test for general association adjusting for site.

Example 6

Figure 8:
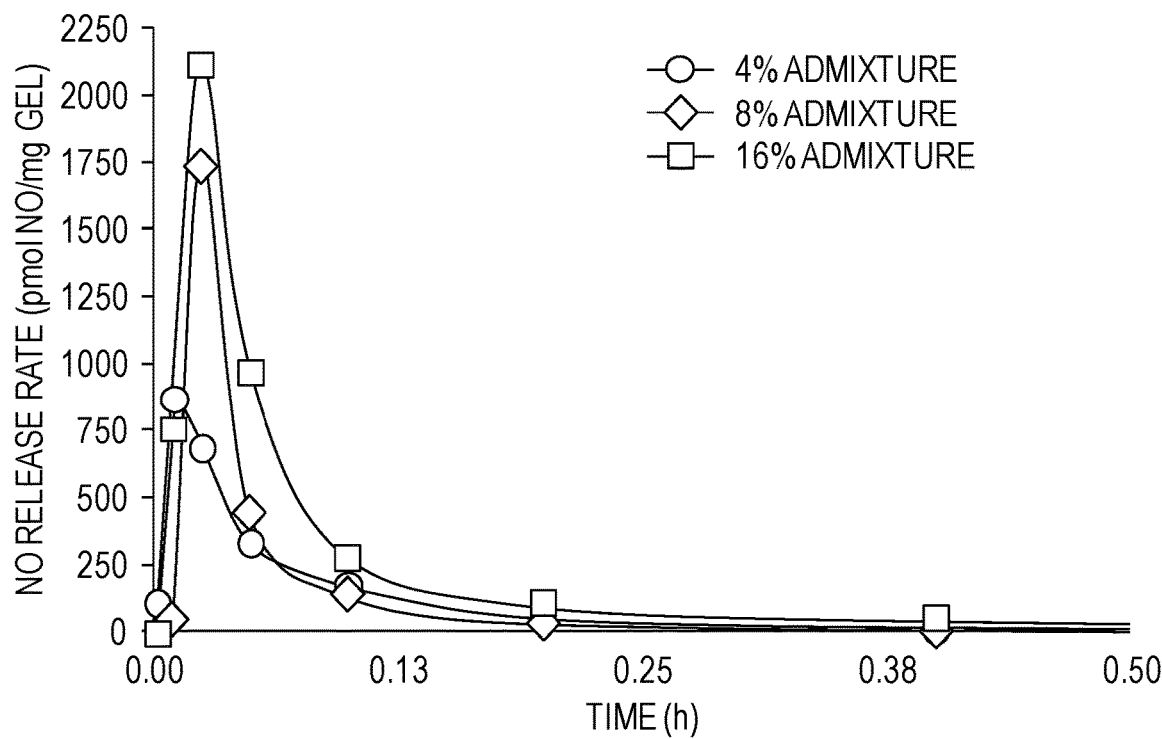
FIG. 8 is a graph of the NO release rate over time for the 4%, 8%, and 16% Nitricil™ NVN1 formulations.
Figure 9:
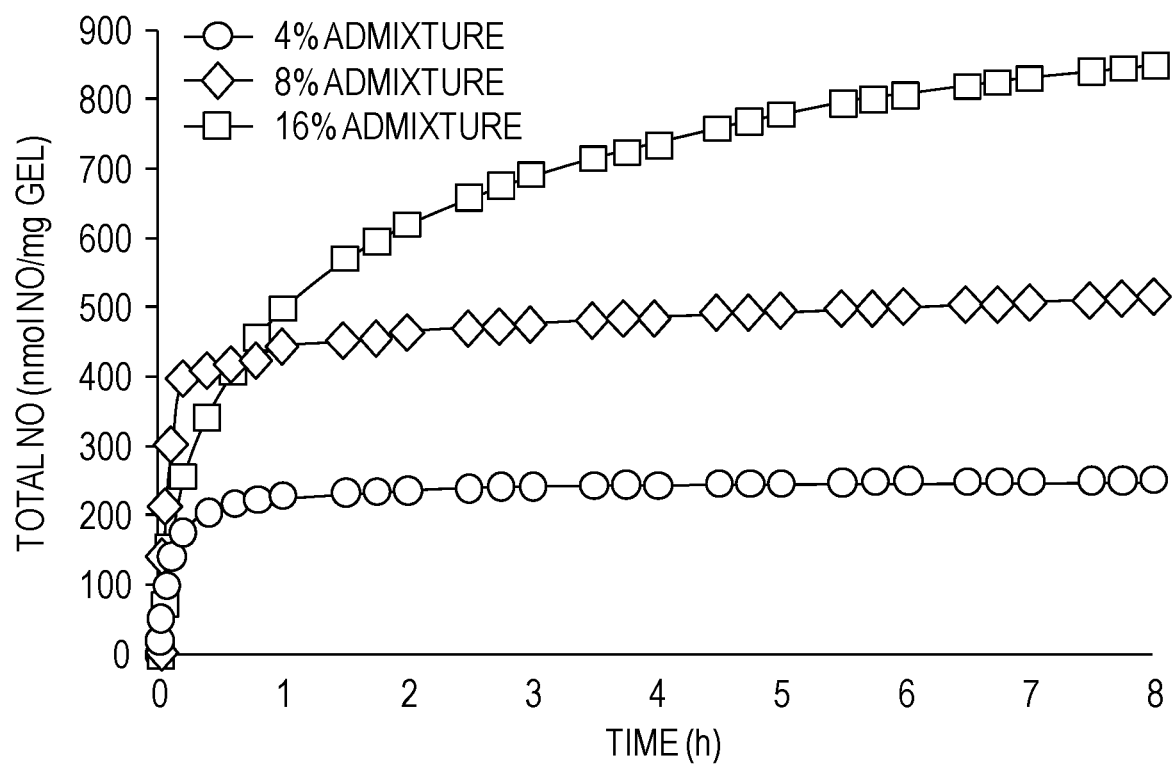
FIG. 9 is a graph of the total NO released over time for the 4%, 8%, and 16% Nitricil™ NVN1 formulations.

In vitro nitric oxide release profiles for 4%, 8%, and 16% Nitricil™ NVN1 Gel Admixture are shown in FIGS. 8 and 9 and are summarized in Table 18 below.

TABLE 18

In Vitro Nitric Oxide Release Summary.

| | Product | | |
|---|---|---|---|
| | 4% Nitricil ™ NVN1 Gel Admixture | 8% Nitricil ™ NVN1 Gel Admixture | 16% Nitricil ™ NVN1 Gel Admixture |
| Components | 8% Nitricil ™ NVN1 Gel + pH 4 Hydrogel | 16% Nitricil ™ NVN1 Gel + pH 4 Hydrogel | 32% Nitricil ™ NVN1 Gel + pH 4 Hydrogel |
| Cmax (pmol NO) | 868 | 1742 | 2114 |
| Total NO (nmol NO/mg Gel) | 253 | 514 | 851 |
| Tmax (min) | 0.6 | 1.8 | 1.8 |

| Time (hr) | [NO] Released (pmol/mg) | Total NO (nmol/mg) | [NO] Released (pmol/mg) | Total NO (nmol/mg) | [NO] Released (pmol/mg) | Total NO (nmol/mg) |
|---|---|---|---|---|---|---|
| 0.00 | 119.69 | 0.67 | 0.67 | 0.01 | 1.47 | 0.01 |
| 0.01 | 867.87 | 20.21 | 59.12 | 0.43 | 761.26 | 0.01 |
| 0.03 | 693.52 | 53.56 | 1742.17 | 141.35 | 2114.28 | 0.17 |
| 0.05 | 336.37 | 99.10 | 448.68 | 214.58 | 973.29 | 75.46 |
| 0.10 | 178.19 | 143.82 | 141.24 | 303.60 | 287.69 | 158.04 |
| 0.20 | 60.04 | 178.63 | 42.70 | 398.91 | 104.72 | 257.67 |
| 0.40 | 22.71 | 206.68 | 21.02 | 408.82 | 55.74 | 343.42 |
| 0.60 | 10.39 | 217.94 | 12.48 | 416.21 | 38.96 | 409.01 |
| 0.80 | 8.08 | 224.58 | 9.20 | 424.31 | 30.29 | 458.72 |
| 1.00 | 5.30 | 228.85 | 10.51 | 446.07 | 24.18 | 500.18 |
| 1.50 | 2.34 | 234.85 | 7.11 | 452.58 | 14.74 | 571.84 |
| 1.75 | 2.02 | 236.84 | 4.60 | 458.18 | 12.38 | 598.47 |
| 2.00 | 1.61 | 238.46 | 4.21 | 467.10 | 11.26 | 619.69 |
| 2.50 | 1.25 | 241.11 | 3.92 | 470.94 | 8.66 | 659.85 |
| 2.75 | 1.08 | 242.18 | 3.77 | 474.32 | 7.77 | 677.57 |
| 3.00 | 1.03 | 243.15 | 3.53 | 480.35 | 7.27 | 692.82 |
| 3.50 | 0.87 | 244.92 | 2.80 | 483.09 | 6.36 | 715.74 |
| 3.75 | 0.84 | 245.69 | 2.63 | 485.65 | 6.14 | 727.21 |
| 4.00 | 0.77 | 246.41 | 2.14 | 490.19 | 5.86 | 738.64 |

TABLE 18-continued

In Vitro Nitric Oxide Release Summary.

| | Product | | | | |
|---|---|---|---|---|---|
| | 4% Nitricil ™ NVN1 Gel Admixture | | 8% Nitricil ™ NVN1 Gel Admixture | | 16% Nitricil ™ NVN1 Gel Admixture |
| 4.50 | 0.71 | 247.74 | 2.38 | 492.26 | 4.99 | 760.36 |
| 4.75 | 0.67 | 248.36 | 1.92 | 494.16 | 4.60 | 770.28 |
| 5.00 | 0.62 | 248.93 | 1.88 | 497.73 | 4.19 | 779.54 |
| 5.50 | 0.54 | 249.98 | 1.94 | 499.49 | 3.90 | 795.94 |
| 5.75 | 0.49 | 250.44 | 1.83 | 501.14 | 3.72 | 803.27 |
| 6.00 | 0.45 | 250.87 | 1.83 | 504.25 | 3.56 | 810.22 |
| 6.50 | 0.41 | 251.66 | 1.50 | 505.69 | 3.15 | 822.38 |
| 6.75 | 0.40 | 252.02 | 1.46 | 507.07 | 2.94 | 827.86 |
| 7.00 | 0.38 | 252.36 | 1.27 | 509.60 | 2.87 | 832.93 |
| 7.50 | 0.36 | 253.01 | 1.39 | 510.80 | 2.76 | 842.22 |
| 7.75 | 0.32 | 253.31 | 1.18 | 511.94 | 2.69 | 846.59 |
| 8.00 | 0.33 | 253.61 | 1.24 | 514.18 | 2.56 | 850.86 |

The composition of the pH 4 Hydrogel is shown in Table 19 below.

TABLE 19

Composition of pH 4 Hydrogel.

| Ingredient | % w/w |
|---|---|
| Purified Water Decon, or equivalent | 55.10 |
| Methylvinyl Ether/Maleic Anhydride Copolymer Gantrez S-97 HSU, Ashland | 18.00 |
| Potassium Phosphate, Monobasic Fisher, or equivalent | 11.50 |
| Ethanol, Anhydrous Decon, or equivalent | 5.00 |
| Cyclomethicone ST-Cyclomethicone-5, Dow Corning | 5.00 |
| Carboxymethylcellulose, Sodium Aqualon CMC 7M8SF PH, Ashland | 2.00 |
| Benzyl Alcohol J.T. Baker, or equivalent | 2.50 |
| Carbomer Interpolymer Type B Carbopol 2020 ETD, Lubrizol | 0.80 |
| Benzoic Acid Spectrum, or equivalent | 0.10 |
| | 100.00 |

The compositions of the 8%, 16%, and 32% Nitricil™ NVN1 Gels are shown in Table 20 below.

TABLE 20

Compositions of 4%, 8%, 16% and 32% Nitricil ™ NVN1 Gels.

| | % w/w | | | |
|---|---|---|---|---|
| Ingredient | 4% | 8% | 16% | 32% |
| Diethylene Glycol Monoethyl Ether Transcutol, P, Gattefossé | 34.00 | 33.00 | 30.00 | 26.00 |
| Hexylene Glycol Amresco | 25.00 | 23.00 | 20.00 | 14.00 |
| Cyclomethicone ST-Cyclomethicone-5, Dow Corning | 18.00 | 18.00 | 18.00 | 17.00 |
| Ethanol, Anhydrous [(1)] Decon, or equivalent | 15.40 | 14.70 | 12.90 | 8.40 |
| Nitricil ™ NVN1 Drug Substance [(1)] Novan, Inc. | 4.00 | 8.00 | 16.00 | 32.00 |
| Cyclopentasiloxane/Dimethicone Crosspolymer ST-Elastomer-10, Dow Corning | 2.00 | 2.00 | 2.00 | 1.75 |
| Hydroxypropyl Cellulose Klucel MF Pharm, Ashland | 1.50 | 1.20 | 1.00 | 0.75 |
| Titanium Dioxide Spectrum, or equivalent | 0.10 | 0.10 | 0.10 | 0.10 |
| | 100.00 | 100.00 | 100.00 | |

[(1)] The dispensed amount of Nitricil ™ NVN1 Drug Substance is based on the potency of MAP3-NONOate of the drug substance and will be adjusted when the content of the respective Nitricil ™ NVN1 Drug Substance batch is <56.8%.
The dispensed amount of Ethanol, Anhydrous will be equally adjusted based on the final calculated adjustment of Nitricil ™ NVN1 Drug Substance to equal 100.0%.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. An admixture comprising:
   a hydrogel comprising:
      a thickening agent present in an amount of about 0.1% to about 25% by weight of the hydrogel,
      water present in an amount of about 50% to about 95% by weight of the hydrogel, and
      a buffering agent present in an amount of about 5% to about 20% by weight of the hydrogel; and
   an anhydrous gel comprising
      a nitric oxide-releasing active pharmaceutical ingredient (API), wherein the nitric oxide-releasing API comprises a diazeniumdiolate-functionalized polysiloxane macromolecule,
      a viscosity increasing agent present in an amount of about 0.1% to about 10% by weight of the anhydrous gel, wherein the viscosity increasing agent comprises a silicone elastomer, a silicone emollient present in an amount of about 10% to about 30% by weight of the anhydrous gel,
a humectant present in an amount of about 10% to about 30% by weight of the anhydrous gel,
a C1-C4 alcohol present in an amount of about 1% to about 20% by weight of the anhydrous gel, and
a glycol ether present in an amount of about 20% to about 40% by weight of the anhydrous gel.

2. The admixture of claim 1, wherein the anhydrous gel comprises at least two different viscosity increasing agents.

3. The admixture of claim 1, wherein the nitric oxide-releasing API is present in the composition in an amount of about 0.1% to about 50% by weight of the composition.

4. The admixture of claim 1, wherein the nitric oxide releasing compound comprises a NO-releasing co-condensed silica particle.

5. The admixture of claim 1, wherein the viscosity increasing agent further comprises cellulose, derivatized cellulose, hydroxypropylcellulose, alginate, metallic stearates, hydrophobic and/or hydrophilic fumed silica, and any combination thereof.

6. The admixture of claim 1, wherein the silicone emollient is selected from cyclomethicone, dimethicone, simethicone, C26-28 alkyl dimethicone, C26-28 alkyl methicone, polyphenylsisquioxane, trimethylsiloxysilicate and crosspolymers of cyclopentasiloxane and dimethicone/vinyltrimethylsiloxysilicate, and any combination thereof.

7. The admixture of claim 1, wherein the humectant is a C1-C10 monoalkylene glycol.

8. A method of treating and/or preventing a viral, bacterial, protozoan, and/or fungal infection in and/or on a subject, the method comprising:
administering the admixture of claim 1 to the subject, thereby treating and/or preventing the viral, bacterial, protozoan, and/or fungal infection in and/or on the subject.

9. A method of treating and/or preventing a viral, bacterial, protozoan, and/or fungal infection in and/or on a subject, the method comprising:
administering the admixture of claim 1 to the subject, wherein the composition delivers a total amount of NO of at least about 50 or 100 nmol of NO/mg of the composition at about 1, 3, 5, 10, 20, 30, 40, 50, or 60 minute(s) after an initial time point as measured by in vitro release, thereby treating and/or preventing the viral, bacterial, protozoan, and/or fungal infection in and/or on the subject.

10. A method of increasing the release of nitric oxide from an anhydrous gel comprising a diazeniumdiolate functional group, the method comprising:
contacting the anhydrous gel with a hydrogel to provide an admixture; and
applying the admixture to the skin of a subject,
wherein the anhydrous gel comprises
a nitric oxide-releasing active pharmaceutical ingredient (API), wherein the nitric oxide-releasing API comprises a diazeniumdiolate-functionalized polysiloxane macromolecule,
a viscosity increasing agent present in an amount of about 0.1% to about 10% by weight of the anhydrous gel, wherein the viscosity increasing agent comprises a silicone elastomer, a silicone elastomer blend, and any combination thereof,
a silicone emollient present in an amount of about 10% to about 30% by weight of the anhydrous gel,
a humectant present in an amount of about 10% to about 30% by weight of the anhydrous gel,
a C1-C4 alcohol present in an amount of about 1% to about 20% by weight of the anhydrous gel, and
a glycol ether present in an amount of about 20% to about 40% by weight of the anhydrous gel; and
wherein the hydrogel comprises
a thickening agent present in an amount of about 0.1% to about 25% by weight of the hydrogel;
water present in an amount of about 50% to about 95% by weight of the hydrogel, and
a buffering agent present in an amount of about 5% to about 20% by weight of the hydrogel.

11. The admixture of claim 1, wherein the hydrogel further comprises a second thickening agent that is selected from the group consisting of a carboxypolymethylene, a polyacrylic polymer and/or copolymer, a cellulose ether, a methacrylate, a polyvinylpyrollidone, a cross-linked polyvinyl pyrrolidone, a copolymer of methyl vinyl ether and maleic anhydride, a polyvinylpyrrolidone-vinyl acetate copolymer, polyvinylalcohol, polyethylene oxide, polyethylene glycol, polyvinylalkyl ether-maleic acid copolymer, a carboxy vinyl polymer, a polysaccharide, a gum, and any combination thereof.

12. The admixture of claim 1, wherein the admixture stores and/or releases nitric oxide in an amount of about 0.15% to about 20% by weight of the anhydrous gel.

13. The admixture of claim 1, wherein the admixture stores and/or releases about 0.1 µmol to about 7 µmol of nitric oxide per mg of the diazeniumdiolate-functionalized polysiloxane macromolecule.

14. The admixture of claim 1, wherein the composition delivers a total amount of NO of at least about 50 or 100 nmol of NO/mg of the composition at about 1, 3, 5, 10, 20, 30, 40, 50, or 60 minute(s) after an initial time point as measured by in vitro release.

15. A kit comprising:
a hydrogel comprising:
a thickening agent present in an amount of about 0.1% to about 25% by weight of the hydrogel,
water present in an amount of about 50% to about 95% by weight of the hydrogel, and
a buffering agent present in an amount of about 5% to about 20% by weight of the hydrogel; and
an anhydrous gel comprising
a nitric oxide-releasing active pharmaceutical ingredient (API), wherein the nitric oxide-releasing API comprises a diazeniumdiolate-functionalized polysiloxane macromolecule,
a viscosity increasing agent present in an amount of about 0.1% to about 10% by weight of the anhydrous gel, wherein the viscosity increasing agent comprises a silicone elastomer, silicone elastomer blend, and any combination thereof,
a silicone emollient present in an amount of about 10% to about 30% by weight of the anhydrous gel,
a humectant present in an amount of about 10% to about 30% by weight of the anhydrous gel,
a C1-C4 alcohol present in an amount of about 1% to about 20% by weight of the anhydrous gel, and
a glycol ether present in an amount of about 20% to about 40% by weight of the anhydrous gel.

16. The admixture of claim 1, wherein the hydrogel has a pH in a range of about 3 to about 5.

* * * * *

UNITED STATES PATENT AND TRADEMARK OFFICE
CERTIFICATE OF CORRECTION

PATENT NO. : 11,166,980 B2
APPLICATION NO. : 16/091167
DATED : November 9, 2021
INVENTOR(S) : Doxey et al.

It is certified that error appears in the above-identified patent and that said Letters Patent is hereby corrected as shown below:

In the Specification

Column 5, Line 55: Please correct "1 µmol" to read -- 1 pmol --

Column 5, Line 59: Please correct "50 µmol" to read -- 50 pmol --

Column 5, Line 65: Please correct "µmol" to read -- pmol --

Column 6, Line 3: Please correct "1500 µmol" to read -- 1500 pmol --

Column 6, Line 9: Please correct "3500 µmol" to read -- 3500 pmol --

Column 6, Line 17: Please correct "1500 µmol" to read -- 1500 pmol --

Column 20, Line 9: Please correct "1 µmol" to read -- 1 pmol --

Column 26, Line 64: Please correct "(MAPS)" to read -- (MAP3) --

Column 27, Line 4: Please correct "alkyl and is" to read -- alkyl and R' is --

Column 27, Line 39: Please correct "(MAPS)" to read -- (MAP3) --

Column 27, Line 42: Please correct "(MAPS)" to read -- (MAP3) --

Column 28, Line 63: Please correct "amount of NC)" to read -- amount of NO --

Column 35, Line 3: Please correct "9.5%" to read -- 95% --

Signed and Sealed this
Twenty-sixth Day of April, 2022

Katherine Kelly Vidal
*Director of the United States Patent and Trademark Office*